(12) United States Patent
Skelton

(10) Patent No.: US 9,907,959 B2
(45) Date of Patent: Mar. 6, 2018

(54) VELOCITY DETECTION FOR POSTURE-RESPONSIVE THERAPY

(75) Inventor: Dennis M. Skelton, Woodinville, WA (US)

(73) Assignee: Medtronic, Inc., Minneapolis, MN (US)

( * ) Notice: Subject to any disclaimer, the term of this patent is extended or adjusted under 35 U.S.C. 154(b) by 1175 days.

(21) Appl. No.: 13/445,506

(22) Filed: Apr. 12, 2012

(65) Prior Publication Data

US 2013/0274830 A1 Oct. 17, 2013

(51) Int. Cl.
*A61N 1/36* (2006.01)

(52) U.S. Cl.
CPC ....... *A61N 1/36128* (2013.01); *A61N 1/3605* (2013.01)

(58) Field of Classification Search
CPC .......................... A61N 1/36542; A61N 1/36535
USPC ........................................................... 607/62
See application file for complete search history.

(56) References Cited

U.S. PATENT DOCUMENTS

| | | |
|---|---|---|
| 4,297,685 A | 10/1981 | Brainard, II |
| 4,365,633 A | 12/1982 | Loughman |
| 4,543,955 A | 10/1985 | Schroeppel |
| 4,550,736 A | 11/1985 | Broughton et al. |
| 4,566,456 A | 1/1986 | Koning et al. |
| 4,771,780 A | 9/1988 | Sholder |
| 4,776,345 A | 10/1988 | Cohen et al. |
| 4,846,180 A | 7/1989 | Buffet |
| 4,846,195 A | 7/1989 | Alt |
| 5,031,618 A | 7/1991 | Mullett |
| 5,040,534 A | 8/1991 | Mann et al. |
| 5,040,536 A | 8/1991 | Riff |

(Continued)

FOREIGN PATENT DOCUMENTS

| | | |
|---|---|---|
| DE | 19831109 | 1/2000 |
| DE | 10024103 | 11/2001 |

(Continued)

OTHER PUBLICATIONS

"Analysis of heart rate dynamics by methods derived from non-linear mathematics: Clinical applicability and prognostic significance," http://herkules.oulu.fi.isbn9514250133/html, 4 pp., 2004.

(Continued)

*Primary Examiner* — Joseph Dietrich
(74) *Attorney, Agent, or Firm* — Shumaker & Sieffert, P.A.

(57) ABSTRACT

The disclosure describes techniques for modifying an electrical stimulation or another type of therapy provided to a patient by a medical device. The therapy modification may be based on a posture and/or activity state of a patient that is detected by an IMD, such as a change in a detected posture state occupied by the patient. Different therapy modifications may be applied for different changes in detected posture state. An IMD may modify therapy based on a transition from one posture state to another posture state. The IMD may determine a posture state of the patient for use in controlling therapy adjustments and/or other aspects of the system. In some examples, when the patient's movement and/or activity velocity exceeds a velocity threshold, a previously-determined stable posture state of the patient may be used to control therapy rather than a current posture state of the patient, which may be transient.

30 Claims, 17 Drawing Sheets

(56) References Cited

U.S. PATENT DOCUMENTS

| | | |
|---|---|---|
| 5,058,584 A | 10/1991 | Bourgeois |
| 5,125,412 A | 6/1992 | Thornton |
| 5,154,180 A | 10/1992 | Blanchet et al. |
| 5,158,078 A | 10/1992 | Bennett et al. |
| 5,167,229 A | 12/1992 | Peckham et al. |
| 5,233,984 A | 8/1993 | Thompson |
| 5,275,159 A | 1/1994 | Griebel |
| 5,312,446 A | 5/1994 | Holschbach et al. |
| 5,335,657 A | 8/1994 | Terry, Jr. et al. |
| 5,337,758 A | 8/1994 | Moore et al. |
| 5,342,409 A | 8/1994 | Mullett |
| 5,354,317 A | 10/1994 | Alt |
| 5,425,750 A | 6/1995 | Moberg |
| 5,476,483 A | 12/1995 | Bornzin et al. |
| 5,487,755 A | 1/1996 | Snell et al. |
| 5,513,645 A | 5/1996 | Jacobson et al. |
| 5,514,162 A | 5/1996 | Bornzin et al. |
| 5,558,640 A | 9/1996 | Pfeiler et al. |
| 5,562,707 A | 10/1996 | Prochazka et al. |
| 5,593,431 A | 1/1997 | Sheldon |
| 5,622,428 A | 4/1997 | Bonnet |
| 5,628,317 A | 5/1997 | Starkebaum et al. |
| 5,643,332 A | 7/1997 | Stein |
| 5,645,053 A | 7/1997 | Remmers et al. |
| 5,674,258 A | 10/1997 | Henschel et al. |
| 5,711,316 A | 1/1998 | Elsberry et al. |
| 5,720,770 A | 2/1998 | Nappholz et al. |
| 5,732,696 A | 3/1998 | Rapoport et al. |
| 5,741,310 A | 4/1998 | Wittkampf |
| 5,782,884 A | 7/1998 | Stotts et al. |
| 5,814,093 A | 9/1998 | Stein |
| 5,832,932 A | 11/1998 | Elsberry et al. |
| 5,833,709 A | 11/1998 | Rise et al. |
| 5,836,989 A | 11/1998 | Shelton |
| 5,851,193 A | 12/1998 | Arikka et al. |
| 5,865,760 A | 2/1999 | Lidman et al. |
| 5,885,471 A | 3/1999 | Ruben et al. |
| 5,893,883 A | 4/1999 | Torgerson et al. |
| 5,895,371 A | 4/1999 | Levitas et al. |
| 5,904,708 A | 5/1999 | Goedeke |
| 5,911,738 A | 6/1999 | Sikorski et al. |
| 5,913,727 A | 6/1999 | Ahdoot |
| 5,919,149 A | 7/1999 | Allum |
| 5,938,690 A | 8/1999 | Law et al. |
| 5,941,906 A | 8/1999 | Barreras, Sr. et al. |
| 5,944,680 A | 8/1999 | Christopherson et al. |
| 5,957,957 A | 9/1999 | Sheldon |
| 6,027,456 A | 2/2000 | Feler et al. |
| 6,044,297 A | 3/2000 | Sheldon et al. |
| 6,083,475 A | 3/2000 | Sikorski et al. |
| 6,045,513 A | 4/2000 | Stone et al. |
| 6,059,576 A | 5/2000 | Brann |
| 6,095,991 A | 8/2000 | Krausman et al. |
| 6,099,479 A | 8/2000 | Christopherson et al. |
| 6,102,874 A | 8/2000 | Stone et al. |
| 6,120,467 A | 9/2000 | Schallhorn |
| 6,128,534 A | 10/2000 | Park et al. |
| 6,134,459 A | 10/2000 | Roberts et al. |
| 6,157,857 A | 12/2000 | Dimpfel |
| 6,165,143 A | 12/2000 | Van Lummel |
| 6,216,537 B1 | 4/2001 | Henschel et al. |
| 6,259,948 B1 | 7/2001 | Florio et al. |
| 6,280,409 B1 | 8/2001 | Stone et al. |
| 6,296,606 B1 | 10/2001 | Goldberg et al. |
| 6,308,098 B1 | 10/2001 | Meyer |
| 6,308,099 B1 | 10/2001 | Fox et al. |
| 6,315,740 B1 | 11/2001 | Singh |
| 6,327,501 B1 | 12/2001 | Levine et al. |
| 6,341,236 B1 | 1/2002 | Osorio et al. |
| 6,351,672 B1 | 2/2002 | Park et al. |
| 6,368,284 B1 | 4/2002 | Bardy |
| 6,381,496 B1 | 4/2002 | Meadows et al. |
| 6,393,325 B1 | 5/2002 | Mann et al. |
| 6,438,408 B1 | 8/2002 | Mulligan et al. |
| 6,440,090 B1 | 8/2002 | Schallhorn |
| 6,449,508 B1 | 9/2002 | Sheldon et al. |
| 6,459,934 B1 | 10/2002 | Kadhiresan |
| 6,466,821 B1 | 10/2002 | Pianca et al. |
| 6,468,234 B1 | 10/2002 | Van der Loos et al. |
| 6,507,757 B1 | 1/2003 | Swain et al. |
| 6,514,218 B2 | 2/2003 | Yamamoto |
| 6,516,749 B1 | 2/2003 | Salasidis |
| 6,539,249 B1 | 3/2003 | Kadhiresan et al. |
| 6,547,755 B1 | 4/2003 | Lippe et al. |
| 6,572,557 B2 | 6/2003 | Tchou et al. |
| 6,574,507 B1 | 6/2003 | Bonnet |
| 6,605,038 B1 | 8/2003 | Teller et al. |
| 6,609,031 B1 | 8/2003 | Law et al. |
| 6,611,783 B2 | 8/2003 | Kelly, Jr. et al. |
| 6,620,151 B2 | 9/2003 | Blischak et al. |
| 6,625,493 B2 | 9/2003 | Kroll et al. |
| 6,635,048 B1 | 10/2003 | Ullestad et al. |
| 6,641,542 B2 | 11/2003 | Cho et al. |
| 6,658,292 B2 | 12/2003 | Kroll et al. |
| 6,659,968 B1 | 12/2003 | McClure |
| 6,662,047 B2 | 12/2003 | Sorensen |
| 6,665,558 B2 | 12/2003 | Kalgren et al. |
| 6,668,188 B2 | 12/2003 | Sun et al. |
| 6,687,538 B1 | 2/2004 | Hrdlicka et al. |
| 6,731,984 B2 | 5/2004 | Cho et al. |
| 6,740,075 B2 | 5/2004 | Lebel et al. |
| 6,748,276 B1 | 6/2004 | Daignault, Jr. et al. |
| 6,752,766 B2 | 6/2004 | Kowallik et al. |
| 6,773,404 B2 | 8/2004 | Poezevera et al. |
| 6,782,315 B2 | 8/2004 | Lu et al. |
| 6,817,979 B2 | 11/2004 | Nihtilä |
| 6,820,025 B2 | 11/2004 | Bachmann et al. |
| 6,829,507 B1 | 12/2004 | Lidman et al. |
| 6,832,113 B2 | 12/2004 | Belalcazar |
| 6,834,436 B2 | 12/2004 | Townsend |
| 6,853,863 B2 | 2/2005 | Carter et al. |
| 6,878,121 B2 | 4/2005 | Krausman et al. |
| 6,879,352 B1 | 4/2005 | Kim |
| 6,884,596 B2 | 4/2005 | Civelli et al. |
| 6,890,306 B2 | 5/2005 | Poezevera |
| 6,895,341 B2 | 5/2005 | Barrey et al. |
| 6,922,587 B2 | 7/2005 | Weinberg |
| 6,923,784 B2 | 8/2005 | Stein |
| 6,928,324 B2 | 8/2005 | Park et al. |
| 6,937,899 B2 | 8/2005 | Sheldon et al. |
| 6,937,900 B1 | 8/2005 | Pianca et al. |
| 6,945,934 B2 | 9/2005 | Bardy |
| 6,964,641 B2 | 11/2005 | Cho et al. |
| 6,975,904 B1 | 12/2005 | Sloman |
| 6,997,882 B1 | 2/2006 | Parker et al. |
| 6,999,817 B2 | 2/2006 | Park et al. |
| 7,016,730 B2 | 3/2006 | Temes |
| 7,031,772 B2 | 4/2006 | Condie |
| 7,043,305 B2 | 5/2006 | KenKnight et al. |
| 7,054,687 B1 | 5/2006 | Andersen |
| 7,066,910 B2 | 6/2006 | Bauhahn et al. |
| 7,082,333 B1 | 7/2006 | Bauhahn |
| 7,092,759 B2 | 8/2006 | Nehls et al. |
| 7,095,424 B2 | 8/2006 | Satoh et al. |
| 7,110,820 B2 | 9/2006 | Tcheng et al. |
| 7,117,036 B2 | 10/2006 | Florio |
| 7,123,967 B2 | 10/2006 | Weinberg |
| 7,130,681 B2 | 10/2006 | Gebhardt et al. |
| 7,130,689 B1 | 10/2006 | Turcott |
| 7,141,026 B2 | 11/2006 | Aminian et al. |
| 7,142,921 B2 | 11/2006 | Mattes et al. |
| 7,149,579 B1 | 12/2006 | Koh et al. |
| 7,149,584 B1 | 12/2006 | Koh et al. |
| 7,151,961 B1 | 12/2006 | Whitehurst et al. |
| 7,155,279 B2 | 12/2006 | Whitehurst et al. |
| 7,160,252 B2 | 1/2007 | Cho et al. |
| 7,162,304 B1 | 1/2007 | Bradley |
| 7,167,743 B2 | 1/2007 | Heruth et al. |
| 7,167,751 B1 | 1/2007 | Whitehurst et al. |
| 7,181,281 B1 | 2/2007 | Kroll |
| 7,189,204 B2 | 3/2007 | Ni et al. |
| 7,207,947 B2 | 4/2007 | Koh et al. |
| 7,210,240 B2 | 5/2007 | Townsend et al. |
| 7,212,862 B2 | 5/2007 | Park et al. |

(56) References Cited

U.S. PATENT DOCUMENTS

| | | |
|---|---|---|
| 7,214,197 B2 | 5/2007 | Prass |
| 7,218,968 B2 | 5/2007 | Condie et al. |
| 7,221,979 B2 | 5/2007 | Zhou et al. |
| 7,231,254 B2 | 6/2007 | DiLorenzo |
| 7,242,983 B2 | 7/2007 | Frei et al. |
| 7,252,640 B2 | 8/2007 | Ni et al. |
| 7,266,412 B2 | 9/2007 | Stypulkowski |
| 7,308,311 B2 | 12/2007 | Sorensen et al. |
| 7,313,440 B2 | 12/2007 | Miesel |
| 7,317,948 B1 | 1/2008 | King et al. |
| 7,330,760 B2 | 2/2008 | Heruth et al. |
| 7,366,569 B2 | 4/2008 | Belalcazar |
| 7,366,572 B2 | 4/2008 | Heruth et al. |
| 7,387,610 B2 | 6/2008 | Stahmann |
| 7,389,147 B2 | 6/2008 | Wahlstrand et al. |
| 7,395,113 B2 | 7/2008 | Heruth |
| 7,403,820 B2 | 7/2008 | DiLorenzo |
| 7,406,351 B2 | 7/2008 | Wesselink |
| 7,415,308 B2 | 8/2008 | Gerber et al. |
| 7,447,545 B2 | 11/2008 | Heruth et al. |
| 7,471,290 B2 | 12/2008 | Wang et al. |
| 7,471,980 B2 | 12/2008 | Koshiol |
| 7,489,970 B2 | 2/2009 | Lee et al. |
| 7,491,181 B2 | 2/2009 | Heruth et al. |
| 7,505,815 B2 | 3/2009 | Lee et al. |
| 7,519,431 B2 | 4/2009 | Goetz et al. |
| 7,542,803 B2 | 6/2009 | Heruth et al. |
| 7,548,786 B2 | 6/2009 | Lee et al. |
| 7,559,901 B2 | 7/2009 | Maile |
| 7,572,225 B2 | 8/2009 | Stahmann |
| 7,577,479 B2 | 8/2009 | Hartley et al. |
| 7,580,752 B2 | 8/2009 | Gerber et al. |
| 7,584,808 B2 | 9/2009 | Dolgin et al. |
| 7,590,453 B2 | 9/2009 | Heruth |
| 7,590,455 B2 | 9/2009 | Heruth et al. |
| 7,590,481 B2 | 9/2009 | Lu et al. |
| 7,591,265 B2 | 9/2009 | Lee et al. |
| 7,603,170 B2 | 10/2009 | Hatlestad et al. |
| 7,623,919 B2 | 11/2009 | Goetz et al. |
| 7,634,379 B2 | 12/2009 | Noble |
| 7,664,546 B2 | 2/2010 | Hartley et al. |
| 7,672,806 B2 | 3/2010 | Tronconi |
| 7,706,889 B2 | 4/2010 | Gerber et al. |
| 7,717,848 B2 | 5/2010 | Heruth et al. |
| 7,747,330 B2 | 6/2010 | Nolan et al. |
| 7,764,996 B2 | 7/2010 | Zhang et al. |
| 7,769,464 B2 | 8/2010 | Gerber et al. |
| 7,775,993 B2 | 8/2010 | Heruth et al. |
| 7,792,583 B2 | 9/2010 | Heruth et al. |
| 7,801,619 B2 | 9/2010 | Gerber et al. |
| 7,805,196 B2 | 9/2010 | Heruth et al. |
| 7,806,831 B2 | 10/2010 | Lavie et al. |
| 7,813,802 B2 | 10/2010 | Tcheng et al. |
| 7,819,909 B2 | 10/2010 | Goetz et al. |
| 7,822,481 B2 | 10/2010 | Gerber et al. |
| 7,826,981 B2 | 11/2010 | Goode et al. |
| 7,840,268 B2 | 11/2010 | Blischak et al. |
| 7,848,811 B2 | 12/2010 | Moon et al. |
| 7,853,322 B2 | 12/2010 | Bourget et al. |
| 7,881,798 B2 | 2/2011 | Miesel et al. |
| 7,887,493 B2 | 2/2011 | Stahmann et al. |
| 7,894,908 B2 | 2/2011 | Lee et al. |
| 7,908,013 B2 | 3/2011 | Miesel et al. |
| 7,927,253 B2 | 4/2011 | Vincent et al. |
| 7,957,797 B2 | 6/2011 | Bourget et al. |
| 7,957,809 B2 | 6/2011 | Bourget et al. |
| 7,961,109 B2 | 6/2011 | Jang et al. |
| 8,000,789 B2 | 8/2011 | Denison |
| 8,002,553 B2 | 8/2011 | Hatlestad et al. |
| 8,016,776 B2 | 9/2011 | Bourget et al. |
| 8,021,299 B2 | 9/2011 | Miesel et al. |
| 8,021,119 B2 | 10/2011 | Gerber et al. |
| 8,032,224 B2 | 10/2011 | Miesel et al. |
| 8,033,996 B2 | 10/2011 | Behar |
| 8,055,348 B2 | 11/2011 | Heruth et al. |
| 8,103,351 B2 | 1/2012 | Gerber et al. |
| 8,111,166 B2 | 2/2012 | Flexer et al. |
| 8,121,694 B2 | 2/2012 | Molnar et al. |
| 8,135,473 B2 | 3/2012 | Miesel et al. |
| 8,155,753 B2 | 4/2012 | Wesselink |
| 8,200,341 B2 | 6/2012 | Sanghera |
| 8,204,597 B2 | 6/2012 | Gerber et al. |
| 8,206,325 B1 * | 6/2012 | Najafi .................. A61B 5/1116 600/587 |
| 8,529,448 B2 | 9/2013 | McNair |
| 8,649,862 B2 | 2/2014 | Ludwig et al. |
| 2002/0091308 A1 | 7/2002 | Kipshidze et al. |
| 2002/0107553 A1 | 8/2002 | Hill et al. |
| 2002/0165586 A1 | 11/2002 | Hill et al. |
| 2002/0169485 A1 | 11/2002 | Pless et al. |
| 2004/0049132 A1 | 3/2004 | Barron et al. |
| 2004/0147975 A1 | 7/2004 | Popovic et al. |
| 2004/0257693 A1 | 12/2004 | Ehrlich |
| 2005/0060001 A1 | 3/2005 | Singhal et al. |
| 2005/0113887 A1 | 5/2005 | Bauhahn |
| 2005/0172311 A1 | 8/2005 | Hjelt et al. |
| 2005/0177192 A1 | 8/2005 | Rezai et al. |
| 2005/0209512 A1 | 9/2005 | Heruth et al. |
| 2005/0215847 A1 | 9/2005 | Heruth et al. |
| 2005/0222638 A1 | 10/2005 | Foley et al. |
| 2005/0228455 A1 | 10/2005 | Kramer et al. |
| 2005/0234518 A1 | 10/2005 | Heruth et al. |
| 2006/0190049 A1 | 8/2006 | Gerber et al. |
| 2006/0195051 A1 | 8/2006 | Schnapp et al. |
| 2006/0206167 A1 | 9/2006 | Flaherty et al. |
| 2006/0235289 A1 | 10/2006 | Wesselink et al. |
| 2006/0253043 A1 | 11/2006 | Zhang et al. |
| 2006/0262120 A1 | 11/2006 | Rosenberg |
| 2006/0265025 A1 | 11/2006 | Goetz et al. |
| 2006/0287686 A1 | 12/2006 | Cullen et al. |
| 2007/0032748 A1 | 2/2007 | McNeil et al. |
| 2007/0073355 A1 | 3/2007 | DiLorenzo et al. |
| 2007/0118056 A1 | 5/2007 | Wang et al. |
| 2007/0123758 A1 | 5/2007 | Miesel et al. |
| 2007/0129641 A1 | 6/2007 | Sweeney |
| 2007/0129769 A1 | 6/2007 | Bourget et al. |
| 2007/0250134 A1 | 10/2007 | Miesel et al. |
| 2007/0255154 A1 | 11/2007 | Lu et al. |
| 2007/0276439 A1 | 11/2007 | Miesel et al. |
| 2007/0293917 A1 | 12/2007 | Thompson |
| 2008/0081958 A1 | 4/2008 | Denison et al. |
| 2008/0164979 A1 | 7/2008 | Otto |
| 2008/0188909 A1 | 8/2008 | Bradley |
| 2008/0194998 A1 | 8/2008 | Holmstrom et al. |
| 2008/0281381 A1 | 11/2008 | Gerber et al. |
| 2008/0300470 A1 | 12/2008 | Gerber et al. |
| 2009/0030263 A1 | 1/2009 | Heruth et al. |
| 2009/0036951 A1 | 2/2009 | Heruth et al. |
| 2009/0046056 A1 | 2/2009 | Rosenberg et al. |
| 2009/0076343 A1 | 3/2009 | Kristofer et al. |
| 2009/0082829 A1 | 3/2009 | Panken et al. |
| 2009/0105785 A1 | 4/2009 | Wei et al. |
| 2009/0118599 A1 | 5/2009 | Heruth et al. |
| 2009/0228841 A1 | 9/2009 | Hildreth |
| 2009/0259216 A1 | 10/2009 | Drew et al. |
| 2009/0264789 A1 | 10/2009 | Molnar et al. |
| 2009/0306740 A1 | 12/2009 | Heruth et al. |
| 2010/0010380 A1 | 1/2010 | Panken et al. |
| 2010/0010381 A1 | 1/2010 | Skelton et al. |
| 2010/0010382 A1 | 1/2010 | Panken et al. |
| 2010/0010383 A1 | 1/2010 | Skelton et al. |
| 2010/0010384 A1 | 1/2010 | Panken et al. |
| 2010/0010385 A1 | 1/2010 | Skelton et al. |
| 2010/0010386 A1 | 1/2010 | Skelton et al. |
| 2010/0010387 A1 | 1/2010 | Skelton et al. |
| 2010/0010388 A1 | 1/2010 | Panken et al. |
| 2010/0010389 A1 | 1/2010 | Davis et al. |
| 2010/0010390 A1 | 1/2010 | Skelton et al. |
| 2010/0010391 A1 | 1/2010 | Skelton et al. |
| 2010/0010392 A1 | 1/2010 | Skelton et al. |
| 2010/0010432 A1 | 1/2010 | Skelton et al. |
| 2010/0010571 A1 | 1/2010 | Skelton et al. |
| 2010/0010572 A1 | 1/2010 | Skelton et al. |
| 2010/0010573 A1 | 1/2010 | Skelton et al. |

(56) References Cited

U.S. PATENT DOCUMENTS

| | | |
|---|---|---|
| 2010/0010574 A1 | 1/2010 | Skelton et al. |
| 2010/0010575 A1 | 1/2010 | Skelton et al. |
| 2010/0010576 A1 | 1/2010 | Skelton et al. |
| 2010/0010577 A1 | 1/2010 | Skelton et al. |
| 2010/0010578 A1 | 1/2010 | Skelton et al. |
| 2010/0010579 A1 | 1/2010 | Skelton et al. |
| 2010/0010580 A1 | 1/2010 | Skelton et al. |
| 2010/0010583 A1 | 1/2010 | Panken et al. |
| 2010/0010584 A1 | 1/2010 | Skelton et al. |
| 2010/0010585 A1 | 1/2010 | Davis et al. |
| 2010/0010586 A1 | 1/2010 | Skelton et al. |
| 2010/0010587 A1 | 1/2010 | Skelton et al. |
| 2010/0010588 A1 | 1/2010 | Skelton et al. |
| 2010/0010589 A1 | 1/2010 | Skelton et al. |
| 2010/0010590 A1 | 1/2010 | Skelton et al. |
| 2010/0030286 A1 | 2/2010 | Goetz et al. |
| 2010/0076525 A1 | 3/2010 | Dame et al. |
| 2010/0105210 A1 | 4/2010 | Hedberg et al. |
| 2010/0106210 A1 | 4/2010 | Hedberg et al. |
| 2010/0121415 A1 | 5/2010 | Skelton et al. |
| 2010/0174155 A1 | 7/2010 | Heruth et al. |
| 2010/0280417 A1 | 11/2010 | Skelton et al. |
| 2010/0280440 A1 | 11/2010 | Skelton et al. |
| 2010/0280500 A1 | 11/2010 | Skelton et al. |
| 2010/0280578 A1 | 11/2010 | Skelton et al. |
| 2011/0172562 A1 | 7/2011 | Sahasrabudhe et al. |
| 2011/0172567 A1 | 7/2011 | Panken et al. |
| 2011/0172927 A1 | 7/2011 | Sahasrabudhe et al. |
| 2011/0201969 A1 | 8/2011 | Hatlestad et al. |
| 2011/0270134 A1 | 11/2011 | Skelton |

FOREIGN PATENT DOCUMENTS

| | | |
|---|---|---|
| EP | 0564803 | 10/1993 |
| EP | 0845240 | 6/1998 |
| EP | 0849715 | 6/1998 |
| EP | 0613390 | 10/2000 |
| EP | 1195139 | 4/2002 |
| EP | 1291036 | 3/2003 |
| EP | 1308182 | 5/2003 |
| EP | 1331022 | 7/2003 |
| EP | 1391846 | 2/2004 |
| EP | 1437159 | 7/2004 |
| EP | 1731088 | 12/2006 |
| EP | 1870128 | 12/2007 |
| EP | 1938862 | 7/2008 |
| EP | 2110067 | 10/2009 |
| GB | 2330912 | 5/1999 |
| GB | 2408342 | 5/2005 |
| GB | 2447647 | 9/2008 |
| WO | 94/05371 | 3/1994 |
| WO | 96/29007 | 9/1996 |
| WO | 97/04705 | 2/1997 |
| WO | 97/49455 | 12/1997 |
| WO | 98/00197 | 1/1998 |
| WO | 99/56820 | 11/1999 |
| WO | 01/37930 | 5/2001 |
| WO | 02/28282 | 4/2002 |
| WO | 02/41771 | 5/2002 |
| WO | 02/87433 | 11/2002 |
| WO | 02/96512 | 12/2002 |
| WO | 02/100267 | 12/2002 |
| WO | 03/51356 | 6/2003 |
| WO | 03/65891 | 8/2003 |
| WO | 05/28029 | 3/2005 |
| WO | 05/35050 | 4/2005 |
| WO | 05/79487 | 9/2005 |
| WO | 05/89646 | 9/2005 |
| WO | 05/89647 | 9/2005 |
| WO | 05/89860 | 9/2005 |
| WO | 05/102499 | 11/2005 |
| WO | 05/120348 | 12/2005 |
| WO | 07/09088 | 1/2007 |
| WO | 07/51196 | 5/2007 |
| WO | 07/64682 | 6/2007 |
| WO | 07/64936 | 6/2007 |
| WO | 07/127455 | 11/2007 |
| WO | 08/26970 | 3/2008 |

OTHER PUBLICATIONS

"Design Competition: Runners-Up for the Best Three Designs," EPN, vol. 26, No. 1, 1 pg., 2002.

"IBM and Citizen Watch develop Linux-Based WatchPad," http://wwwlinuxdevices.com/news/NS6580187845.html, 5 pp., 2006.

"MiniMitter® Physiological and Behavioral Monitoring for Humans and Animals," http://www.minimitter.com/Products/Actiwatch, 3 pp., 2006.

"Watch," Wikipedia, 6 pp., http://en.wikipedia.org/wiki/Watch, 2006.

Aminian et al., "Physical Activity Monitoring Based on Accelerometry: Validation and Comparison with Video Observation," Medical & Biological Engineering and Computing, vol. 37, No. 2, pp. 304-308,1999.

Amzica, "Physiology of Sleep and Wakefulness as it Relates to the Physiology of Epilepsy," Journal of Clinical Neurophysiology, American Clinical Neurophysiology Society, 19(6)1, pp. 488-503, 2002.

Ang et al., "Physical model of a MEMS accelerometer for low-g motion tracking applications," 2004 IEEE International Conference on Robotics and Automation, vol. 2, pp. 1345-1351, 2004.

Buchser et al., "Improved Physical Activity in Patients Treated for Chronic Pain by Spinal Cord Stimulation," Neuromodulation, vol. 8, Issue 1, pp. 40-48, Mar. 2005.

Crago et al., "An Elbow Extension Neuroprosthesis for Individuals with Tetraplegia," IEEE Transactions on Rehabilitation Engineering, vol. 6, No. 1, pp. 1-6, Mar. 1998.

Dejnabadi et al., "Estimation and Visualization of Sagittal Kinematics of Lower Limbs Orientation Using Body-Fixed Sensors," IEEE Transactions on Biomedical Engineering, vol. 53, No. 7, pp. 1385-1393, Jul. 2006.

Dinner, "Effect of Sleep on Epilepsy," Journal of Clinical Neurophysiology, American Clinical Neurophysiology Society, 19(6), pp. 504-513, 2002.

Foerster et al., "Motion Pattern and Posture: Correctly Assessed by Calibrated Accelerometers," Forschungsgrupe Psychophysiologie, Universität Freiburg, Germany, Mar. 2000, 28 pp.

Foldvary-Schaefer, "Sleep Complaints and Epilepsy: The Role of Seizures, Antiepileptic Drugs and Sleep Disorders," Journal of Clinical Neurophysiology, American Clinical Neurophysiology Society, 19(6), pp. 514-521, 2002.

Fourcade et al., "Modeling Phase Transitions in Human Posture," Studies in Perception and Action VII, Sheena Rogers & Judith Effken (eds), Lawrence Erlbaum Associated, Inc., pp. 99-103, 2003.

Giansanti et al., "The development and test of a device for the reconstruction of 3-D position and orientation by means of a kinematic sensor assembly with rate gyroscopes and accelerometers," IEEE Transactions on Biomedical Engineering, v. 52, No. 7, pp. 1271-1277, Jul. 2005.

Goodrich et al., "The Prediction of Pain Using Measures of Sleep Quality," Pain Digest, 8:23-25, 1998.

Heinz et al., "Using Wearable Sensors for Real-time Recognition Tasks in Games of Martial Arts—An Initial Experiment," Institute for Computer Systems and Networks (CSN), UMIT—University of Health Systems, Medical Informatics and Technology Hall in Tyrol, Austria, 2006 5 pp. http://eis.comp.lancs.ac.uk/fileadmin/relate/publication/2006-WearableSensors.pdf.

Hendelman et al., "Validity of Accelerometry for the Assessment of Moderate Intensity Physical Activity in the Field," Medicine & Science in Sports & Exercise, pp. S442-S449, 2000.

Hinckley, K., Pierce, J., Sinclair, M., Horvitz, E., Sensing Techniques for Mobile Interaction, ACM UIST 2000 Symposium on User Interface Software & Technology, CHI Letters 2 (2), pp. 91-100.

Husak, "Model of Tilt Sensor Systems,"ICECS 2002, 9$^{th}$ IEEE International Conference on Electronics, Circuits and Systems, vol. 1, pp. 227-230, 2002.

(56) References Cited

OTHER PUBLICATIONS

Karantonis et al., "Implementation of a Real-Time Human Movement Classifier Using a Triaxial Accelerometer for Ambulatory Monitoring," IEEE Transactions on Information Technology in Biomedicine, vol. 10, No. 1, pp. 156-167, Jan. 2006.

Kassam, "2005 EDP Topic "MK4": Tremor Data-Logger for Parkinson's Disease Patients," http://www.ee.ryerson.ca/~courses/edp2005/MK4.html, 3 pp., 2005.

Kerr et al., "Analysis of the sit-stand-sit movement cycle in normal subjects," Clinical Biomechanics, vol. 12, No. 4, pp. 236-245, 1977.

Kiani et al., "Computerized Analysis of Daily Life Motor Activity for Ambulatory Monitoring," Technology and Health Care 5, pp. 307-318, 1997.

Kitchin et al., "Compensating for the 0 g Offset Drift of the ADXL50 Accelerometer," Analog Devices Application Note AN-380, 2 pp.

Lau, "Strategies for Generating Prolonged Functional Standing Using Intramuscular Stimulation or Intraspinal Microstimulation," IEEE Transactions on Neural Systems and Rehabilitation Engineering, vol. 15 No. 2, pp. 273-285, Jun. 2007.

Leiper et al., "Sensory Feedback for Head Control in Cerebral Palsy," Physical Therapy, vol. 61, No. 4, pp. 512-518, Apr. 1981.

Lorussi, "Wearable, Redundant Fabric-Based Sensor Arrays for Reconstruction of Body Segment Posture," IEEE Sensors Journal, vol. 4, No. 6, pp. 808-817, Dec. 2004.

Mathie et al., "A Pilot Study of Long-Term Monitoring of Human Movements in the Home Using Accelerometer," Journal of Telemedicine and Telecare10:144-151, Jun. 2007.

Mathie et al., "Determining Activity Using a Triaxial Accelerometer," Proceedings of the Second Joint EMBS/BMES Conference, Houston, TX, pp. 2481-2482, Oct. 23-26, 2002.

Mattmann et al., "Recognizing Upper Body Postures Using Textile Strain Sensors," Proceedings Eleventh IEEE International Symposium on Wearable Computers, ISWC, pp. 29-36, 2007.

Mendez et al., "Interactions Between Sleep and Epilepsy," Journal of Clinical Neurophysiology, American Clinical Neurophysiology Society, 18(2), pp. 106-127, 2001.

Paraschiv-Ionescu et al., "Ambulatory System for the Quantitative and Qualitative Analysis of Patients Treated with Spinal Cord Stimulation," Gait and Posture, vol. 20, Issue 2, pp. 113-125, Oct. 2004.

Quwaider, et al., "Body Posture Identification Using Hidden Markov Model with a Wearable Sensor Network," XP-002632420, Abstract, 8 pp.

Slyper et al., "Action Capture with Accelerometers," Eurographics/ACM SIGGRAPH Symposium on Computer Animation, Carnegie Mellon University, 7 pp. 2008.

Smith et al., "How do sleep disturbance and chronic pain interrelate? Insights from the longitudinal and cognitive-behavioral clinical trials literature," Sleep Medicine Reviews, YSMRV 286, pp. 1-14, 2003.

Smith et al., "Presleep cognitions in Patients with Insomnia Secondary to Chronic Pain," Journal of Behavioral Medicine, vol. 24, No. 1, pp. 93-114, 2001.

Emmanuel Munguia Tapia, "Activity Recognition from Accelerometer Data for Videogame Applications," http://alumni.media.mit.edu/~emunguia/html/videogames.htm, 7 pp., Dec. 2, 2003, printed Oct. 1, 2009.

Trolier-Mckinstry et al., "Thin Film Piezoelectrics for MEMS," Journal of Electroceramics, v. 12, No. 1-2, pp. 7-17, Jan./Mar. 2004.

Tuck, "Implementing Auto-Zero Calibration Technique for Accelerometers," Freescale Semiconductor Application Note AN3447, 5 pp., Mar. 2007.

Tuisku, "Motor Activity Measured by Actometry in Neuropsychiatric Disorders," Department of Psychiatry, University of Helsinki, Helsinki, Finland, 115 pp., 2002.

Vega-Gonzalez, "Upper Limb Activity Monitoring," Arch Phys Med Rehabil, vol. 86, pp. 541-548, Mar. 2005.

Velten et al., "A New Three-Axis Accelerometer," Sensor '99—$9^{th}$ Int'l Traide Fair and Conference for Sensors/Transducers & Systems, Nürnberg, Germany, May 18-20, 1999, Sensor '99 Proceedings II, A 5.2, pp. 47-52, 1999.

PCT/US09/49991: International Search Report and Written Opinion dated Oct. 5, 2009, 15 pp.

PCT/US09/49219: International Search Report and Written Opinion dated Oct. 20, 2010, 27 pp.

PCT/US09/49005: International Search Report and Written Opinion dated Nov. 27, 2009, 19 pp.

PCT/US09/48260: International Search Report and Written Opinion dated Sep. 10, 2009, 16 pp.

PCT/US09/48282: International Search Report and Written Opinion dated Sep. 3, 2009, 16 pp.

PCT/US09/49180: International Search Report and Written Opinion, dated Oct. 1, 2009, 14 pp.

PCT/US09/49241: International Search Report and Written Opinion dated Oct. 7, 2009, 14 pp.

PCT/US09/49393: International Search Report and Written Opinion dated May 7, 2010, 15 pp.

PCT/US09/48999: International Search Report and Written Opinion dated Sep. 22, 2009, 14 pp.

PCT/US09/48228: International Search Report and Written Opinion dated Sep. 4, 2009, 16 pp.

PCT/US09/49396: International Search Report and Written Opinion dated Sep. 27, 2010, 19 pp.

PCT/US09/49390: International Search Report and Written Opinion dated May 7, 2010, 14 pp.

PCT/US09/49184: International Search Report and Written Opinion dated Apr. 7, 2009, 16 pp.

PCT/US09/48852: International Search Report and Written Opinion dated Apr. 6, 2010, 17 pp.

PCT/US09/48686: International Search Report and Written Opinion dated Apr. 7, 2010, 16 pp.

PCT/US09/55204: International Search Report and Written Opinion dated Jan. 22, 2010, 18 pp.

PCT/US09/49071: International Search Report and Written Opinion dated Apr. 7, 2010, 17 pp.

PCT/US09/48676: International Search Report and Written Opinion dated Apr. 7, 2010, 16 pp.

PCT/US09/48995: International Search Report and Written Opinion dated Apr. 7, 2010, 16 pp.

\* cited by examiner

VELOCITY DETECTION FOR POSTURE-RESPONSIVE THERAPY

TECHNICAL FIELD

The disclosure relates to medical devices and, more particularly, to programmable medical devices that deliver therapy.

BACKGROUND

A variety of medical devices are used for chronic, e.g., long-term, delivery of therapy to patients suffering from a variety of conditions, such as chronic pain, tremor, Parkinson's disease, epilepsy, urinary or fecal incontinence, sexual dysfunction, obesity, or gastroparesis. As examples, electrical stimulation generators are used for chronic delivery of electrical stimulation therapies such as cardiac pacing, neurostimulation, muscle stimulation, or the like. Pumps or other fluid delivery devices may be used for chronic delivery of therapeutic agents, such as drugs. Typically, such devices provide therapy continuously or periodically according to parameters contained within a program. A program may comprise respective values for each of a plurality of parameters, specified by a clinician.

In some cases, the patient may be allowed to activate and/or modify the therapy delivered by the medical device. For example, a patient can be provided with a patient programming device. The patient programming device communicates with a medical device to allow the patient to activate therapy and/or adjust therapy parameters. For example, an implantable medical device (IMD), such as an implantable neurostimulator, may be accompanied by an external patient programmer that permits the patient to activate and deactivate neurostimulation therapy and/or adjust the intensity of the delivered neurostimulation. The patient programmer may communicate with the IMD via wireless telemetry to control the IMD and/or retrieve information from the IMD.

SUMMARY

In general, the disclosure describes techniques for modifying therapy provided to a patient by a medical device. The techniques are applicable to electrical stimulation therapy or other therapies. In some examples, modification of therapy includes adjustment of one or more therapy parameter values that define one or more characteristics of therapy delivered to a patient. In some examples, the therapy modification is based on activity of a patient that is detected by an IMD, such as a change in a detected posture state occupied by the patient.

Different therapy modifications may be applied for different changes in detected posture state.

Therapy modifications may be applied in association with each new posture state that the patient enters. For instance, when the patient is in a lying posture state, therapy may be delivered according to parameters associated with that lying position. When the patient rises to a sitting or an upright posture state, the therapy delivery may be modified accordingly based on parameter values associated with that newly-assumed position.

In some case, while the patient is moving between one stable posture state and another stable posture state, it may be advantageous to temporarily suspend modification of therapy delivery according to the intermediate transient posture states assumed by the patient. For instance, assume that during a transition from a stable lying posture state to a stable upright posture state, the patient enters several other posture states that are only maintained for a short period of time. Such posture states may include, for instance, bending over or leaning backwards. Although these posture states may be defined posture states associated with therapy parameters, it may not be desirable to control therapy delivery based on detection of these posture states because they are only temporarily entered by the patient during the transition from lying down to standing upright. Instead, it may be more desirable to continue delivering therapy according to the most-recently-detected stable posture state (i.e., the lying posture state in this example). Once the patient reaches a stable upright posture state, therapy modification may be performed in accordance with this newly-assumed stable position.

Suspending therapy modification while the patient is in transition between posture states may prevent modifications that are uncomfortable for the patient or that decrease therapy levels below what is needed to complete the posture state transition in a smooth and successful manner. Moreover, therapy modifications that are based on only a very temporarily-sustained posture state may waste processing resources and drain power unnecessarily.

One example of the foregoing determines when a patient's movement velocity has increased beyond a movement velocity threshold. When this occurs, the system uses the patient's most-recently-detected stable posture state to determine the parameters with which to deliver therapy to the patient. This may be the posture state in which the patient resided just prior to, or at, the time the patient's movement velocity exceeded the velocity threshold.

Stated another way, the system temporarily suspends automatic therapy adjustments based on posture state while the patient's movement velocity is above the velocity threshold. Therapy levels may be maintained at levels that are based on the patient's previous stable posture state (unless manual patient adjustments are made to the therapy levels). This will conserve processing resources and limit power consumption, since the system need not continuously respond to the various temporarily-assumed posture states. After the patient's movement velocity again drops below the predetermined threshold, therapy delivery based on a current posture state (rather than on the most-recent stable posture state, may resume.)

According to some aspects, detection of a patient's current posture state may be suspended during times of relatively high patient velocity. Instead of detecting the patient's current posture state during this period, the patient's most-recent stable posture state is attributed to the patient for use in controlling aspects of the system. For instance, the patient's most-recently-detected stable posture state may be used to control therapy or to control some other aspect of system operation (e.g., sensing of a signal, prompting of a system notification, etc.) So long as the patient has a movement velocity that is above the velocity threshold, the posture state in use within the system for therapy control is a previously-detected stable posture state of the patient.

In one example, techniques described herein may involve a posture state module. The posture state module may be configured to determine a posture state of the patient based on the one or more posture state parameters and a relationship between a velocity of the patient and a velocity threshold. For instance, so long as the patient's movement velocity remains at, or below, a velocity threshold, the posture state module may determine a current posture state of the patient based on currently-sensed values for posture state parameters. However, when the patient's movement velocity rises above a velocity threshold, the posture state in use by the system may be based on a previously-determined posture state (as determined by previously-collected posture state parameters).

One example according to this disclosure includes a system comprising a sensor to sense one or more posture state parameters of a patient and a posture state module configured to determine a posture state of the patient to be used in controlling an aspect of the system. The posture state is determined based on the one or more posture state parameters and a relationship between a velocity of the patient and a velocity threshold. The posture state module may be configured to determine the posture state of the patient based on a previously-determined posture state of the patient if the velocity of the patient exceeds the velocity threshold. This posture state module may further be configured to determine the velocity of the patient based on a DC component of the posture state parameters. The system may further comprise a therapy delivery module configured to deliver therapy to the patient based on the posture state of the patient. The therapy delivery module may be configured to deliver therapy to the patient based on a current posture state of the patient and to temporarily suspend delivering therapy based on the current posture state of the patient during period of time wherein the velocity of the patient exceeds a predetermined velocity threshold. The system may further comprise an implantable medical device comprising the sensor, and/or a programmer configured to receive input to control the medical system.

Another aspect of the disclosure relates to a method, comprising sensing one or more posture state parameters of a patient and determining, via a posture state module, a posture state of the patient for use in controlling an aspect of the system. The determined posture state is determined based on the one or more posture state parameters and a relationship between a velocity of the patient and a velocity threshold. The method may further comprise delivering therapy to the patient based on the posture state of the patient. This therapy may be delivered to the patient based on a previously-determined posture state of the patient during time periods wherein the velocity of the patient exceeds the velocity threshold and otherwise the therapy may be delivered to the patient based on a current posture state of the patient. Determining the velocity of the patient may comprise determining the velocity based on the one or more posture state parameters. The velocity of the patient may be a movement velocity that is based on an angle or a distance. The velocity may be based on an AC component or a DC component of the one or more posture state parameters.

According to another aspect, a system is disclosed that comprises means for sensing one or more posture state parameters of a patient and means for determining, via a posture state module, a posture state of the patient based on the one or more posture state parameters and a relationship between a velocity of the patient and a velocity threshold. A non-transitory storage medium storing instructions executable by a control circuit is also disclosed. The stored instructions cause the control circuit to perform a method comprising sensing one or more posture state parameters of a patient and determining a posture state of the patient based on the one or more posture state parameters and a relationship between a velocity of the patient and a velocity threshold. The control circuit may comprise a processor, sequencer (e.g., microsequencer), or any other circuit capable of executing instructions.

The details of one or more examples of systems, devices, and techniques are set forth in the accompanying drawings and the description below. Other features, objects, and advantages of the disclosure will be apparent from the description and drawings, and from the claims.

DETAILED DESCRIPTION

Figure 1A:
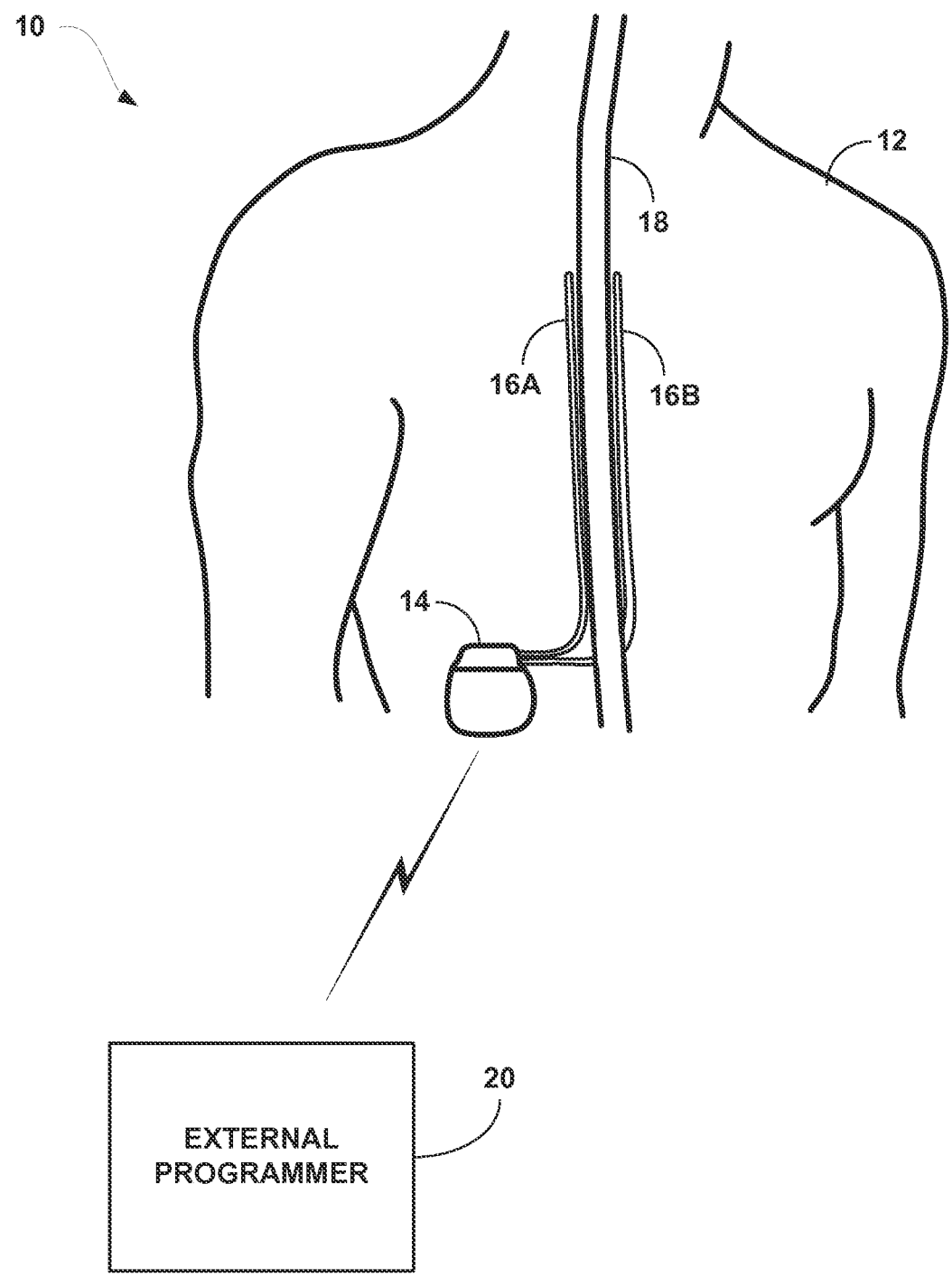
FIG. 1A is a conceptual diagram illustrating an example implantable stimulation system including two implantable stimulation leads.

In some medical devices that deliver electrical stimulation therapy, therapeutic efficacy may change as the patient changes posture states. In general, a posture state may refer to a patient posture or a combination of posture and activity. For example, some posture states, such as upright, may be sub-categorized as upright and active or upright and inactive. Other posture states, such as lying down posture states, may or may not have an activity component. Efficacy may refer, in general, to a combination of complete or partial alleviation of symptoms alone, or in combination with a degree of undesirable side effects.

Changes in posture state may cause changes in efficacy due to changes in distances between electrodes or other therapy delivery elements, e.g., due to temporary migration of leads or catheters caused by forces or stresses associated with different postures, or from changes in compression of patient tissue in different posture states. Also, posture state changes may present changes in symptoms or symptom levels, e.g., pain level. To maintain therapeutic efficacy, it may be desirable to adjust therapy parameters based on different postures and/or activities engaged by the patient. A therapy system may adjust therapy by modifying values for one or more specific therapy parameters, e.g., by specifying adjustments to a specific therapy parameter or by selecting different therapy programs or groups of programs that define different sets of therapy parameter values. A therapy program may define respective values for a set of therapy parameters.

A change in efficacy due to changes in posture state may require the patient to continually manage therapy by manually adjusting certain therapy parameters, such as amplitude, pulse rate, or pulse width, or selecting different therapy programs to achieve more efficacious therapy throughout many different posture states. In some cases, a medical device employs a posture state detector that detects the patient posture state. The medical device adjusts therapy parameters in response to different posture states, which are determined with the posture state detector. Therapy adjustments in response to different posture states may be fully automatic, semi-automatic in the sense that a user may provide approval of proposed changes, or user-directed in the sense that the patient may manually adjust therapy based on the posture state indication.

In general, the disclosure describes techniques for modifying therapy provided to a patient by a medical device. The techniques are applicable to electrical stimulation therapy or other therapies, such as therapeutic agent delivery therapy. Modification of therapy may include adjustment of one or more therapy parameter values that define one or more characteristics of stimulation therapy delivered to a patient. The therapy modification may be based on activity of a patient that is detected by an implantable medical device (IMD), such as a change in a detected posture state occupied by the patient.

In some cases, it may not be advantageous to perform therapy modification for each newly-detected posture state. For instance, when a patient is in transition between a previous stable posture state and a next target posture state, the patient may be assuming multiple posture states that are only temporarily maintained. According to the current disclosure, it may not be desirable to adjust therapy delivery based on these relatively transient posture states that are assumed while the patient is moving between two stable posture states. Instead, the system may continue to use the patient's previous stable posture state to control therapy and/or other aspects of system operation during the time of transition. As a result, therapy adjustments will not be made based on transient positions the patient may assume while undergoing the movement. Rather, therapy may continue to be delivered according to that most-recent stable posture state. This will be described further below.

The posture-based therapy modification techniques described in this disclosure are generally described in terms of application to electrical stimulation therapies for purposes of illustration. However, such techniques may be applied to other types of therapies, such as therapeutic fluid delivery.

Therapy parameter values associated with electrical stimulation may include voltage or current amplitude, electrode configuration, and frequency. In the case of electrical stimulation pulses, therapy parameter values may include voltage or current pulse amplitude, pulse rate, pulse width and electrode configuration. In some cases, stimulation may involve a continuous waveform, and the therapy parameter values may include the waveform shape. Electrode configuration generally refers to a combination of electrodes and electrode polarities used to deliver stimulation.

Stimulation therapy delivered to a patient may be modified for any of a variety of reasons. In some cases, symptoms such as pain intensity change based on the posture state of the patient. For example, a patient may experience a greater degree of pain while walking compared to standing, while standing compared to sitting, or while sitting compared to a lying posture state. In such cases, it may be desirable to adjust one or more therapy parameter values in order to maintain therapeutic efficacy across multiple posture states. If pain is more intense in a given posture state, for example, stimulation amplitude may be increased to provide more effective pain relief. Posture state changes, in addition to presenting changes in symptoms, may cause implanted therapy elements such as leads and electrodes to migrate relative to one another or relative to a target tissue site.

For example, compression, expansion, or other changes to tissue may render therapy more or less intense due to lead or catheter migration. As an illustration, for spinal cord stimulation (SCS), when a patient transitions from an upright posture state to a lying posture state in which the patient is lying on his back, leads may be compressed inward toward the spinal cord, possibly resulting in an acute increase in stimulation intensity.

To maintain therapeutic efficacy, the stimulation therapy delivered to a patient may be posture-responsive in the sense that one or more therapy parameter values may be modified when a patient transitions between different posture states. For example, an implantable electrical stimulation system may be configured to detect a posture state of a patient and automatically modify stimulation therapy based on the detected posture state.

As a result of the posture-responsive therapy delivery, the values of one or more stimulation parameters of a stimulation signal being delivered as part of a therapy may change over time, e.g., according to a patient's posture state sensed by an implantable stimulation system. As an example, a patient may experience more pain while walking compared to standing. In such cases, an IMD may be configured to automatically modify the stimulation therapy to a relatively higher stimulation intensity when it detects that the patient has transitioned from standing to walking, e.g., by delivering therapy having a higher stimulation amplitude value when the patient is walking compared to the stimulation amplitude value when the patient is standing, to address the increased pain experienced by the patient.

As a further example, an IMD may be configured to automatically modify the stimulation therapy to a lower stimulation intensity when the stimulation system detects that the patient has ceased walking and returned to a standing posture state. In this manner, stimulation therapy delivered to a patient via an IMD may be automatically modified to deliver stimulation appropriate to the posture state exhibited by a patient.

As previously discussed, it may be advantageous to temporarily suspend automatic therapy modification based on a currently-detected posture state in some situations because the patient has entered a relatively high-movement state. During this time, the patient may be transitioning between multiple posture states in fairly rapid succession to get from a previously-assumed stable posture state to a next stable posture state. This transition time may be characterized by the fact that the patient's movement velocity has increased beyond a predetermined movement velocity threshold that is higher than the patient's movement velocity when the patient is in a relatively stable posture state.

During a transition time of high velocity, the temporary posture states occupied by the patient may, but need not, be defined posture states. As a specific example, when transitioning from sitting to standing, the patient may temporarily occupy a bending-over posture state that has previously been defined and is associated with parameters for delivering therapy. If this defined posture state is temporarily occupied during the transition time of high velocity, the system may ignore the posture state for therapy delivery purposes because the patient's velocity is too great. Also during this transition time, the patient may occupy a posture state (e.g., leaning to one side) that was not previously defined for use in controlling therapy delivery or any other aspect of the system. Again, the system may ignore this posture state, both because it was never defined to start with, and additionally because it was detected during a time of high patient movement.

In some examples, when the patient's movement velocity has increased beyond a predetermined movement velocity threshold, therapy is delivered to the patient according to patient's most-recently-detected stable posture state. This may be a posture state detected when the patient was last occupying a stable posture state such that the patient's movement velocity was at, or below, the velocity threshold. Because therapy is being delivered according to this previous posture state, therapy adjustments are not made in response to the various posture states through which the patient is transitioning during the period of relatively high movement velocity.

In one embodiment, during times of relatively high movement, not only is posture-responsive therapy adjustment suspended, but posture state detection itself may also be described as suspended. In other words, in such examples, the system will not classify the patient's posture states during the time of high velocity. Instead, the system will continue to classify the patient as being in whichever posture state was detected prior to the time the patient entered the relatively high-movement period for purposes of controlling certain aspects of the system (e.g., therapy delivery). Thus, as discussed above, therapy will continue to be delivered according to this most-recent stable posture state.

In some scenarios, some other aspect of the system besides, or in addition to, therapy delivery may be controlled based on this most-recently-determined stable posture state. For instance, if the system is monitoring some physiological parameter such as resting heart rate or some other parameter that is most advantageously measured while the patient is in a relatively stable position, it may be desirable to suspend these physiological measurements during times of high movement velocity.

A patient's movement velocity may be detected in various ways. According to one example, signals obtained from a sensor such as a three-axis accelerometer may be used to determine a patient's position in three-dimensional space at various time intervals. The patient's movement velocity can then be determined by comparing a change between successively-occupied posture states divided by the time period over which this change in posture state occurred.

A change between postures states may be determined in various ways. For instance, the change may be derived as a distance between posture states. As merely one example, assume an embodiment wherein each posture states may each be represented as a respective vector in three-dimensional space. A metric that describes the distance between these vectors may be determined. Such a distance metric may be calculated, for example, as a Euclidean distance, a city-block distance, a Manhattan distance, or any other distance measurement that can describe the distance between these two vectors. This derived distance metric may then be divided by the time occurring between the patient assuming the two posture states that are represented by the two vectors. The resulting velocity metric is indicative of the patient's movement velocity.

Next, the determined velocity metric may be compared to a corresponding threshold. In examples disclosed herein, the velocity metric used to describe a patient's distance velocity (e.g., Euclidean distance/time) may be directly proportional to the patient's movement velocity. As such, the comparison between the derived velocity metric may be compared to a velocity threshold to determine whether the derived metric exceeds the threshold. If so, it may be determined that the patient's movement velocity exceeds the movement velocity threshold. If the patient's movement velocity exceeds the threshold, appropriate actions may be taken such as suspending therapy modifications based on posture state changes, and in some examples, suspending posture state detection as well. As described herein, this may save computational steps and help to limit power consumption and heating in some cases.

In another example, vectors representing posture states of a patient may be used to derive a metric describing an angular, rather than a distance, velocity. An angular velocity may, in one instance, be derived by determining a metric that describes an angle between two vectors, wherein the vectors each represent respective posture states in the aforementioned manner. Such a metric may be the angle itself, or may instead be some metric describing the angle (e.g., sine, cosine, etc.) This metric that describes an angle may be divided by time to determine an angular velocity metric.

In a manner similar to that described above, the angular velocity metric may be compared to a threshold to determine whether a predetermined relationship exists between the velocity metric and the threshold value (e.g., "great than", or "great than or equal to"). If such a relationship exists, the patient's movement velocity may be considered to be above a threshold velocity such that some action should be taken, such a suspending therapy modification and/or posture state detection.

As mentioned in the foregoing paragraph, instead of basing the angular velocity off an angle itself, a metric may be determined that describes this angle, such as the sine or cosine of the angle. This use of sine or cosine, rather than the angle itself, may eliminate processing-intensive steps associated with deriving the actual angle. In some such cases (e.g., when cosine values are used) the resulting angular velocity metric may have an inverse relationship to the patient's angular velocity. As such, the derived angular velocity metric may be "less than", or "less than or equal to" the associated threshold selected for that metric during the time periods when the patient's movement velocity exceeds the movement velocity threshold. Therefore, the relationship used to compare a metric to the corresponding threshold for that metric may vary, and need not necessarily be "great than" or "greater than or equal to".

In the above-described examples, some indicator of a distance or a size of an angle is divided by a period of time to obtain a velocity metric. It may be appreciated that if the time period by which the division occurs is always the same, the step of dividing by time is not necessary. Thus, another embodiment may simplify the process by merely utilizing the distance or angle metric itself as an indication of velocity. In this type of embodiment, the metric that describes the distance or angle will be compared to a corresponding distance or angular threshold. For instance, a derived cosine of an angle may be compared against a corresponding threshold (e.g., a cosine less than or equal to 0.5) to determine when the patient's movement velocity has exceeded the velocity threshold, and so on. As another example, a derived Euclidean distance metric may be compared to an predetermined distance threshold (e.g., greater than or equal to four inches, etc.) to determine when the patient's movement velocity has exceeded the threshold. Any distance or angular indications such as the example metrics set forth herein may be used as an indication of patient velocity without a need to divide by a time period so long as the time between successive distance or angular indications is always constant.

The foregoing examples relate to a patient's movement velocity that is determined based on changes in a patient's position in three-dimensional space over time. This movement velocity may be determined by comparing snapshots of the patient's position at successive intervals in time. Other types of velocity may reflect patient activity (e.g., a patient accelerating or decelerating) versus a patient's change in position. In some examples, this activity velocity may be used in a manner similar to movement velocity to suspend making therapy adjustments based on the posture state determination or to suspend determining the patient's posture state altogether. This is described further below.

Hence, the disclosure describes a variety of techniques for posture-responsive therapy modification that make use of comparisons between the patient's velocity as may be determined by various metrics and corresponding threshold values. By suspending therapy modifications and, in some cases, posture state determination, during times when the patient's velocity is relatively high, therapy delivery may continue in a manner that is more comfortable for the patient in some instances. Moreover, the system may conserve processing and power resources.

FIG. 1A is a schematic diagram illustrating an implantable stimulation system 10 including a pair of implantable electrode arrays in the form of stimulation leads 16A and 16B. Although the techniques described in this disclosure are generally applicable to a variety of medical devices including external and implantable medical devices (IMDs), application of such techniques to IMDs and, more particularly, implantable electrical stimulators such as neurostimulators will be described for purposes of illustration. More particularly, the disclosure will refer to an implantable SCS system for purposes of illustration, but without limitation as to other types of medical devices.

As shown in FIG. 1A, system 10 includes an IMD 14 and external programmer 20 shown in conjunction with a patient 12, who is ordinarily a human patient. In the example of FIG. 1A, IMD 14 is an implantable electrical stimulator that delivers SCS, e.g., for relief of chronic pain or other symptoms. Again, although FIG. 1A shows an IMD, other examples may include an external stimulator, e.g., with percutaneously implanted leads. Stimulation energy is delivered from IMD 14 to spinal cord 18 of patient 12 via one or more electrodes of implantable leads 16A and 16B (collectively "leads 16"). In some applications, such as spinal cord stimulation (SCS) to treat chronic pain, the adjacent implantable leads 16 may have longitudinal axes that are substantially parallel to one another.

Although FIG. 1A is directed to SCS therapy, system 10 may alternatively be directed to any other condition that may benefit from stimulation therapy. For example, system 10 may be used to treat tremor, Parkinson's disease, epilepsy, urinary or fecal incontinence, sexual dysfunction, obesity, gastroparesis, migraine headaches, or psychiatric disorders (e.g., depression, mania, obsessive compulsive disorder, anxiety disorders, and the like). In this manner, system 10 may be configured to provide therapy taking the form of deep brain stimulation (DBS), pelvic floor stimulation, gastric stimulation, or any other stimulation therapy.

Each of leads 16 may include electrodes (not shown in FIG. 1A), and the parameters for a program that controls delivery of stimulation therapy by IMD 14 may include information identifying which electrodes have been selected for delivery of stimulation according to a stimulation program, the polarities of the selected electrodes, i.e., the electrode configuration for the program, and voltage or current amplitude, pulse rate, and pulse width of stimulation delivered by the electrodes. Delivery of stimulation pulses will be described for purposes of illustration. However, stimulation may be delivered in other forms, such as continuous waveforms. Programs that control delivery of other therapies by IMD 26 may include other parameters, e.g., such as dosage amount, rate, or the like for drug delivery.

In the example of FIG. 1A, leads 16 carry one or more electrodes that are placed adjacent to the target tissue of the spinal cord. One or more electrodes may be disposed at a distal tip of a lead 16 and/or at other positions at intermediate points along the lead. Electrodes of leads 16 transfer electrical stimulation generated by IMD 14 to tissue of patient 12. The electrodes may be electrode pads on a paddle lead, circular (e.g., ring) electrodes surrounding the body of leads 16, conformable electrodes, cuff electrodes, segmented electrodes, or any other type of electrodes capable of forming unipolar, bipolar or multipolar electrode configurations for therapy. In general, ring electrodes arranged at different axial positions at the distal ends of leads 16 will be described for purposes of illustration.

Leads 16 may be implanted within patient 12 and directly or indirectly (e.g., via a lead extension) coupled to IMD 14. Alternatively, as mentioned above, leads 16 may be implanted and coupled to an external stimulator, e.g., through a percutaneous port. In some cases, an external stimulator is a trial or screening stimulation that used on a temporary basis to evaluate potential efficacy to aid in consideration of chronic implantation for a patient. In additional examples, IMD 14 may be a leadless stimulator with one or more arrays of electrodes arranged on a housing of the stimulator rather than leads that extend from the housing.

IMD 14 delivers electrical stimulation therapy to patient 12 via selected combinations of electrodes carried by one or both of leads 16. The target tissue for the electrical stimulation therapy may be any tissue affected by electrical stimulation energy, which may be in the form of electrical stimulation pulses or waveforms. In some examples, the target tissue includes nerves, smooth muscle, and skeletal muscle. In the example illustrated by FIG. 1A, the target tissue is tissue proximate spinal cord 18, such as within an intrathecal space or epidural space of spinal cord 18, or, in some examples, adjacent nerves that branch off of spinal cord 18. Leads 16 may be introduced into spinal cord 18 in via any suitable region, such as the thoracic, cervical or lumbar regions. Stimulation of spinal cord 18 may, for example, prevent pain signals from traveling through the spinal cord and to the brain of the patient. Patient 12 may perceive the interruption of pain signals as a reduction in pain and, therefore, efficacious therapy results.

The deployment of electrodes via leads 16 is described for purposes of illustration, but arrays of electrodes may be deployed in different ways. For example, a housing associated with a leadless stimulator may carry arrays of electrodes, e.g., rows and/or columns (or other patterns). Such electrodes may be arranged as surface electrodes, ring electrodes, or protrusions. As a further alternative, electrode arrays may be formed by rows and/or columns of electrodes on one or more paddle leads. In some examples, electrode arrays may include electrode segments, which may be arranged at respective positions around a periphery of a lead, e.g., arranged in the form of one or more segmented rings around a circumference of a cylindrical lead.

In the example of FIG. 1A, stimulation energy is delivered by IMD 14 to the spinal cord 18 to reduce the amount of pain perceived by patient 12. As described above, IMD 14 may be used with a variety of different therapies, such as peripheral nerve stimulation (PNS), peripheral nerve field stimulation (PNFS), DBS, cortical stimulation (CS), pelvic floor stimulation, gastric stimulation, and the like. The electrical stimulation delivered by IMD 14 may take the form of electrical stimulation pulses or continuous stimulation waveforms, and may be characterized by controlled voltage levels or controlled current levels, as well as pulse width, pulse rate, and a desired combination of electrodes in the case of stimulation pulses. Stimulation may be delivered in a uni-polar, bi-polar, omni-polar, or multi-polar manner. In some cases, the electrodes that deliver the stimulation may be carried on the IMD case as well as on one or more leads, with some of the electrodes being passive electrodes.

In some examples, IMD 14 generates and delivers stimulation therapy according to one or more programs. A program defines values for one or more parameters that define an aspect of the therapy delivered by IMD 14 according to that program. For example, a program that controls delivery of stimulation by IMD 14 in the form of pulses may define a voltage or current pulse amplitude, a pulse width, a pulse rate, for stimulation pulses delivered by IMD 14 according to that program. Moreover, therapy may be delivered according to multiple programs, wherein multiple programs are contained within each of a plurality of groups.

Each program group may support an alternative therapy selectable by patient 12, and IMD 14 may deliver therapy according to the multiple programs. IMD 14 may rotate through the multiple programs of the group when delivering stimulation such that numerous conditions of patient 12 are treated. As an illustration, in some cases, stimulation pulses formulated according to parameters defined by different programs may be delivered on a time-interleaved basis. For example, a group may include a program directed to leg pain, a program directed to lower back pain, and a program directed to abdomen pain. In this manner, IMD 14 may treat different symptoms substantially simultaneously.

During use of IMD 14 to treat patient 12, movement of patient 12 among different posture states may affect the ability of IMD 14 to deliver consistent efficacious therapy. For example, posture state changes may present changes in symptoms or symptom levels, e.g., pain level. As another example, a patient posture state may affect the relative location between the electrodes of leads 16 and a target therapy site. For example, leads 16 may migrate toward IMD 14 when patient 12 bends at the waist, resulting in displacement of electrodes relative to the target stimulation site and possible disruption in delivery of effective therapy. Stimulation energy transferred to target tissue may be reduced due to electrode migration, which may reduce therapeutic efficacy in terms of relief of symptoms (e.g., pain) or an increase in undesirable side effects.

As another example of how posture state may affect the relative location between the electrodes of leads 16 and a target therapy site, leads 16 may be compressed towards spinal cord 18 when patient 12 lies down. Such compression may cause an increase in the amount of stimulation energy transferred to the target tissue. An increase in stimulation energy transferred to the target stimulation site may cause unusual sensations or an otherwise undesirable intensity of therapy, which may both be considered undesirable side effects that undermine overall efficacy. Thus, in some examples, the amplitude of stimulation therapy may need to be decreased when patient 12 is lying down to avoid causing patient 12 additional pain or unusual sensations resulting from the increased compression near electrodes of leads 16. The additional pain or unusual sensations may be considered undesirable side effects that undermine overall efficacy.

IMD 14 includes a posture state module that detects the patient posture state. The IMD automatically adjusts stimulation according to the detected posture state. The patient posture and activity level can, but need not include an activity component. Example posture states may include "Upright," "Upright and Active," "Lying Down," and so forth. IMD 14 includes a posture responsive therapy mode that, when activated, results in adjustment of one or more stimulation parameter values based on a detected posture state. The posture responsive therapy may help mitigate changes in the efficacy of therapy attributable to patient posture changes. For example, the posture state module may include one or more accelerometers (e.g., one or more single axis, two-axis or three-axis accelerometers) that detect when patient 12 occupies a posture state for which it is appropriate to decrease the stimulation amplitude, e.g., when patient 12 lies down. IMD 14 may automatically reduce stimulation amplitude upon detecting patient 12 is lying down, thereby eliminating the need for patient 12 to manually adjust the therapy, which may be cumbersome. In addition, automatic adjustment of stimulation parameters based on a detected patient posture may also provide more responsive therapy because IMD 14 may detect a change in patient posture and modify therapy parameters faster than patient 12 may be able to manually modify the therapy parameter values.

As will be described in greater detail below, in some examples, IMD 14 is configured to automatically suspend performing therapy adjustments based on a currently-detected posture state of the patient when the IMD detects that patient 12 has a movement velocity that is above a predetermined movement velocity threshold. The IMD may further temporarily suspend posture state detection altogether during this time. In other examples, the IMD may discontinue therapy adjustments but never-the-less continue to determine a patient's current posture state while the patient's movement velocity exceeds the threshold, as may be desirable for patient-monitoring purposes. In this latter scenario, the currently-determined posture states obtained during time of relatively high movement velocity are not used to control therapy delivery. In some examples, the IMD may determine a movement velocity based on a distance measurement that describes a distance between two posture states assumed by the patient. In other examples, the IMD may determine a movement velocity based on some metric that describes an angle between two vectors corresponding to two posture states.

Many other examples of reduced efficacy due to increase coupling or decreased coupling of stimulation energy to target tissue may occur due to changes in posture and/or activity level associated with patient posture state. To avoid or reduce possible disruptions in effective therapy due to posture state changes, IMD 14 includes a posture state module that detects the posture state of patient 12 and causes the IMD 14 to automatically adjust stimulation according to the detected posture state. For example, a posture state module may include a posture state sensor such as an accelerometer that detects when patient 12 lies down, stands up, or otherwise changes posture.

In response to a posture state indication by the posture state module, IMD 14 may change program group, program, stimulation amplitude, pulse width, pulse rate, electrode combination, stimulation mode (e.g., unipolar vs. bipolar), continuous waveform shape, and/or one or more other parameters, groups or programs to maintain therapeutic efficacy. When patient 12 lies down, for example, IMD 14 may automatically reduce stimulation amplitude so that patient 12 does not need to reduce stimulation amplitude manually. In some cases, IMD 14 may communicate with external programmer 20 to present a proposed change in stimulation in response to a posture state change, and receive approval or rejection of the change from a user, such as patient 12 or a clinician, before automatically applying the therapy change. In some examples, posture state detection may also be used to provide notifications, such as providing notification via a wireless link to a care giver that a patient has potentially experienced a fall.

Referring still to FIG. 1A, a user, such as a clinician or patient 12, may interact with a user interface of external programmer 20 to program IMD 14. Programming of IMD 14 may refer generally to the generation and transfer of commands, programs, or other information to control the operation of IMD 14. For example, external programmer 20 may transmit programs, parameter adjustments, program selections, group selections, or other information to control the operation of IMD 14, e.g., by wireless telemetry. As one example, external programmer 20 may transmit parameter adjustments to support therapy modifications relating to changes in the posture state of patient 12. As another example, a user may select programs or program groups. Again, a program may be characterized by an electrode combination, electrode polarities, voltage or current amplitude, pulse width, pulse rate, and/or duration. A group may be characterized by multiple programs that are delivered simultaneously or on an interleaved or rotating basis.

In some cases, external programmer 20 may be characterized as a physician or clinician programmer if it is primarily intended for use by a physician or clinician. In other cases, external programmer 20 may be characterized as a patient programmer if it is primarily intended for use by a patient. A patient programmer is generally accessible to patient 12 and, in many cases, may be a portable device that may accompany the patient throughout the patient's daily routine. In general, a physician or clinician programmer may support selection and generation of programs by a clinician for use by stimulator 14, whereas a patient programmer may support adjustment and selection of such programs by a patient during ordinary use.

IMD 14 may be constructed with a biocompatible housing, such as titanium or stainless steel, or a polymeric material such as silicone or polyurethane, and surgically implanted at a site in patient 12 near the pelvis. IMD 14 may also be implanted in patient 12 at a location minimally noticeable to patient 12. Alternatively, IMD 14 may be external with percutaneously implanted leads. For SCS, IMD 14 may be located in the lower abdomen, lower back, upper buttocks, or other location to secure IMD 14. Leads 16 may be tunneled from IMD 14 through tissue to reach the target tissue adjacent to spinal cord 18 for stimulation delivery.

Figure 1B:
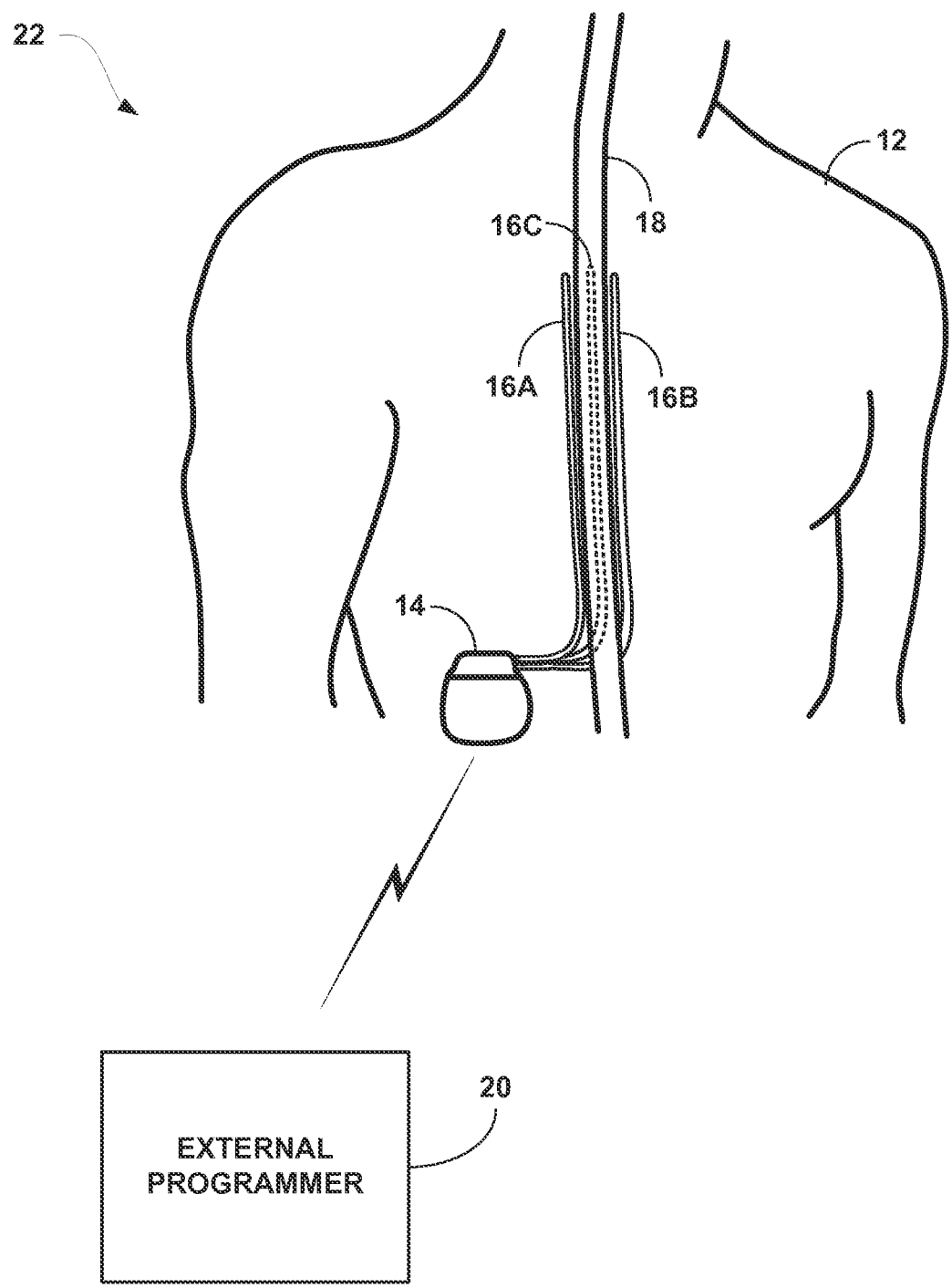
FIG. 1B is a conceptual diagram illustrating an example implantable stimulation system including three implantable stimulation leads.

FIG. 1B is a conceptual diagram illustrating an implantable stimulation system 22 including three implantable stimulation leads 16A, 16B, 16C (collectively leads 16). System 22 generally conforms to system 10 of FIG. 1A, but includes a third lead. Accordingly, IMD 14 may deliver stimulation via combinations of electrodes carried by all three leads 16, or a subset of the three leads. The third lead, e.g., lead 16C, may include a greater number of electrodes than leads 16A and 16B and be positioned between leads 16A and 16B or on one side of either lead 16A or 16B. The number and configuration of leads 16 may be stored within external programmer 20 to allow programmer 20 to appropriately program stimulation therapy or assist in the programming of stimulation therapy.

In some examples, leads 16A and 16B each include four electrodes, while lead 16C includes eight or sixteen electrodes, thereby forming a so-called 4-8-4 or 4-16-4 lead configuration. Other lead configurations, such as 8-16-8, 8-4-8, 16-8-16, 16-4-16, are possible, whereby the number in the configuration indication refers to the number of electrodes in a particular electrode column, which may be defined by a lead 16A-16C. In some cases, electrodes on lead 16C may be smaller in size and/or closer together than the electrodes of leads 16A or 16B. Movement of lead 16C due to changing activities or postures of patient 12 may, in some instances, more severely affect stimulation efficacy than movement of leads 16A or 16B. Patient 12 may further benefit from the ability of IMD 14 to detect posture states and associated changes and automatically adjust stimulation therapy to maintain therapy efficacy in a three lead system 22.

Figure 1C:
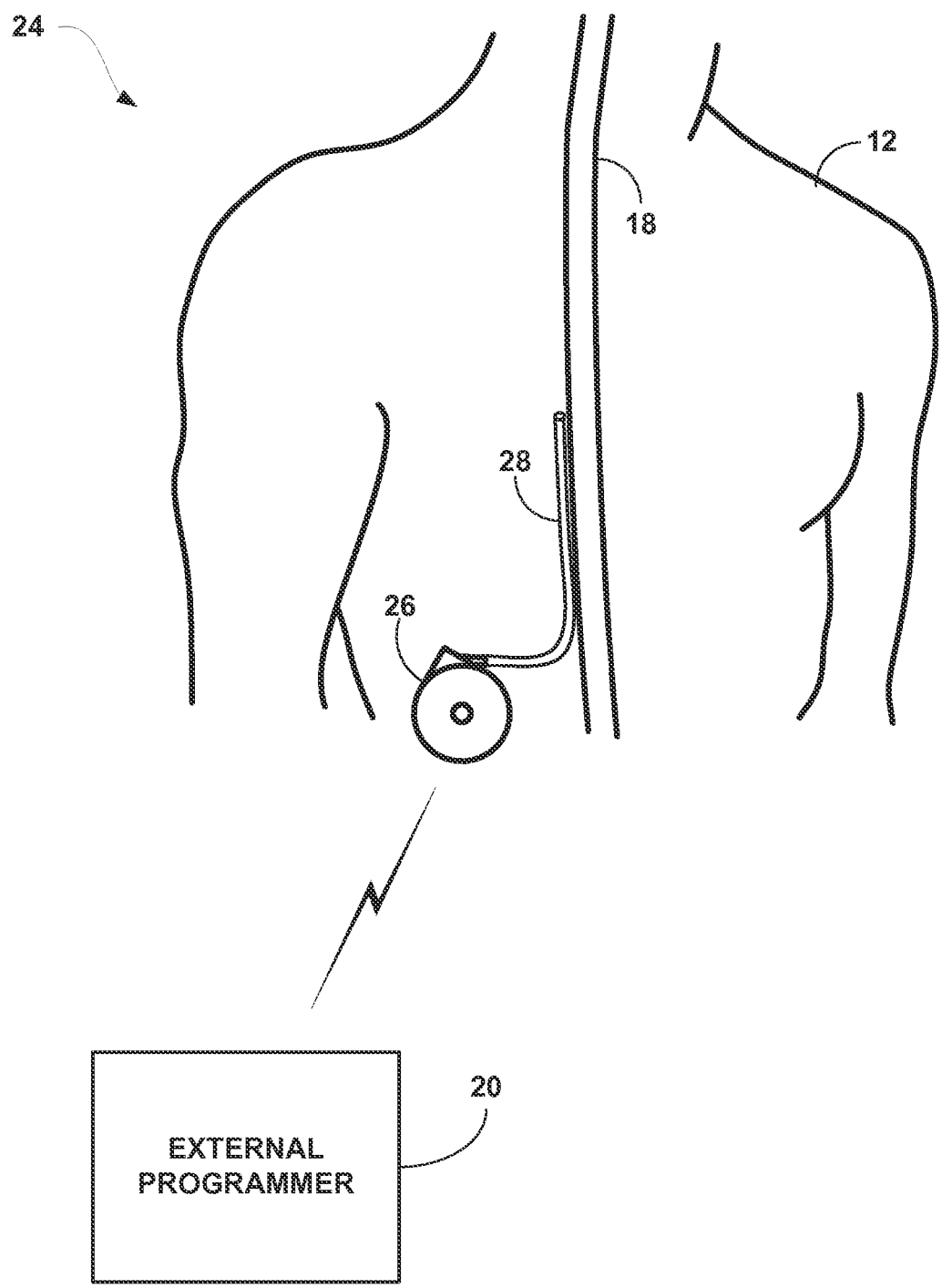
FIG. 1C is a conceptual diagram illustrating an example implantable drug delivery system including a delivery catheter.

FIG. 1C is a conceptual diagram illustrating an implantable drug delivery system 24 including one delivery catheter 28 coupled to IMD 26. As shown in the example of FIG. 1C, drug delivery system 24 is substantially similar to systems 10 and 22. However, drug delivery system 24 performs the similar therapy functions via delivery of one or more therapeutic agents instead of electrical stimulation therapy. IMD 26 functions as a drug pump in the example of FIG. 1C, and IMD 26 communicates with external programmer 20 to initialize therapy or modify therapy during operation. In addition, IMD 26 may be refillable to allow chronic drug delivery.

A fluid delivery port of catheter 28 may be positioned within an intrathecal space or epidural space of spinal cord 18, or, in some examples, adjacent nerves that branch off of spinal cord 18. Although IMD 26 is shown as coupled to only one catheter 28 positioned along spinal cord 18, additional catheters may also be coupled to IMD 26. Multiple catheters may deliver drugs or other therapeutic agents to the same anatomical location or the same tissue or organ. Alternatively, each catheter may deliver therapy to different tissues within patient 12 for the purpose of treating multiple symptoms or conditions. In some examples, IMD 26 may be an external device that includes a percutaneous catheter that to deliver a therapeutic agent to patient 12, e.g., in the same manner as catheter 28. Alternatively, the percutaneous catheter can be coupled to catheter 28, e.g., via a fluid coupler.

In other examples, IMD 26 may include both electrical stimulation capabilities as described in IMD 14 (FIG. 1A) and drug delivery therapy.

IMD 26 may also operate using parameters that define the method of drug delivery. IMD 26 may include programs, or groups of programs, that define different delivery methods for patient 12. For example, a program that controls delivery of a drug or other therapeutic agent may include a titration rate or information controlling the timing or size of bolus deliveries. Patient 14 may use external programmer 20 to adjust the programs or groups of programs to regulate the therapy delivery.

Similar to IMD 14, IMD 26 includes a posture state module that monitors the patient 12 posture state and adjusts therapy accordingly. For example, the posture state module may indicate that patient 12 transitions from lying down to standing up. IMD 26 may automatically increase the rate of drug delivered to patient 12 in the standing position if patient 12 has indicated that pain increased when standing. This automated adjustment to therapy based upon posture state may be activated for all or only a portion of the programs used by IMD 26 to deliver therapy.

Similar to the examples described above with respect to adjustment of one or more electrical stimulation parameters to modify electrical stimulation therapy, IMD 26 may make adjustments to drug delivery therapy. In particular, in some examples, IMD 26 is configured to automatically suspend performing therapy adjustments based on a currently-detected posture state of the patient when the IMD detects that patient 12 has a movement velocity that is above a predetermined movement velocity threshold. The IMD may further temporarily suspend posture state detection altogether during this time. In other examples, the IMD may continue to determine a patient's current posture state while the patient's movement velocity exceeds the threshold, as may be desirable for patient-monitoring purposes, but these currently-determined posture states obtained during time of relatively high movement velocity are not used during this time to control therapy delivery. In some examples, the IMD may determine a movement velocity based on a distance measurement that describes a distance between two posture states assumed by the patient. In other examples, the IMD may determine a movement velocity based on some metric that describes an angle between two vectors corresponding to two posture states assumed by the patient.

As an example, during times when the patient has a relatively stable posture state, the rate of drug delivery to patient 12 may be based on a patient's currently-detected posture state. However, when the patient's velocity climbs above a velocity threshold, the rate of drug delivery may continue to be set to a desirable rate based on a patient's most-recently-determined stable posture state. Once the patient again assumes a more stable posture state such that the patient's movement velocity drops below a velocity threshold, the drug delivery rate may again be based on the patient's current stable posture state. Such adjustments to the drug delivery rate parameter may be automatically made by IMD 26 to modify the drug delivery therapy provided to patient 12 based on the posture state detected by IMD 26.

The techniques described herein for modifying therapy delivery by IMD 14 (FIG. 1A), which provides electrical stimulation therapy, may also be implemented to modify therapy delivery by IMD 26 selected based on a type of detected patient posture transition.

Figure 2:
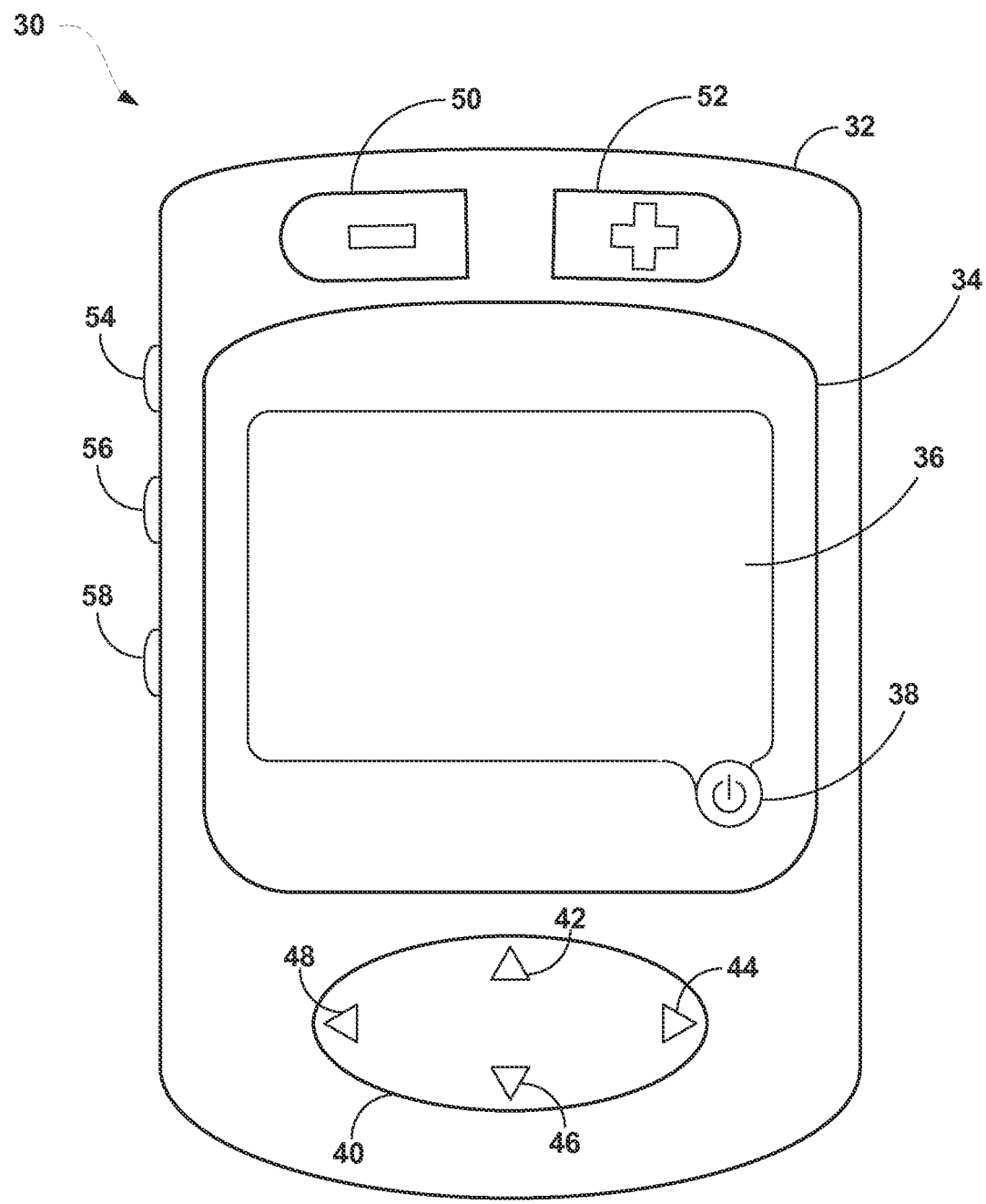
FIG. 2 is a conceptual diagram illustrating an example patient programmer for programming stimulation therapy delivered by an implantable medical device.

FIG. 2 is a conceptual diagram illustrating an example patient programmer 30 for programming stimulation therapy delivered by an IMD. Patient programmer 30 is an example of external programmer 20 illustrated in FIGS. 1A, 1B and 1C and may be used with either IMD 14 or IMD 26. In alternative examples, patient programmer 30 may be used with an external medical device. As shown in FIG. 2, patient programmer 30 provides a user interface (not shown) for a user, such as patient 12, to manage and program stimulation therapy. Patient programmer 30 is protected by housing 32, which encloses circuitry necessary for patient programmer 30 to operate.

Patient programmer 30 also includes display 36, power button 38, increase button 52, decrease button 50, sync button 58, stimulation ON button 54, and stimulation OFF button 56. Cover 34 protects display 36 from being damaged during use of patient programmer 30. Patient programmer 30 also includes control pad 40 which allows a user to navigate through items displayed on display 36 in the direction of arrows 42, 44, 46, and 48. In some examples, the buttons and pad 40 may take the form of soft keys (e.g., with functions and contexts indicated on display 36), with functionality that may change, for example, based on current programming operation or user preference. In alternative examples, display 36 is a touch screen with which patient 12 may directly interact without the use of control pad 40. A touch screen display may eliminate the use of buttons, such as increase button 52 and decrease button 50, although buttons may be used in addition to a touch screen display.

In the illustrated example, patient programmer 30 is a hand held device. Patient programmer 30 may accompany patient 12 throughout a daily routine. In some cases, patient programmer 30 may be used by a clinician when patient 12 visits the clinician in a hospital or clinic. In other examples, patient programmer 30 may be a clinician programmer that remains with the clinician or in the clinic and is used by the clinician and/or patient 12 when the patient is in the clinic. In the case of a clinician programmer, small size and portability may be less important. Accordingly, a clinician programmer may be sized larger than a patient programmer, and it may provide a larger screen for more full-featured programming.

Housing 32 may be constructed of a polymer, metal alloy, composite, or combination material suitable to protect and contain components of patient programmer 30. In addition, housing 32 may be partially or completely sealed such that fluids, gases, or other elements may not penetrate the housing and affect components therein. Power button 38 may turn patient programmer 30 ON or OFF as desired by patient 12. Patient 12 may control the illumination level, or backlight level, of display 36 by using control pad 40 to navigate through the user interface and increase or decrease the illumination level with decrease and increase buttons 50 and 52.

In some examples, illumination may be controlled by a knob that rotates clockwise and counter-clockwise to control patient programmer 30 operational status and display 36 illumination. Patient programmer 30 may be prevented from turning OFF during telemetry with IMD 14 or another device to prevent the loss of transmitted data or the stalling of normal operation. Alternatively, patient programmer 30 and IMD 14 may include instructions that handle possible unplanned telemetry interruption, such as battery failure or inadvertent device shutdown.

Display 36 may include any one or more of a liquid crystal display (LCD), dot matrix display, organic light-emitting diode (OLED) display, touch screen, or similar monochrome or color display capable of providing visible information to patient 12. Display 36 may provide a user interface regarding current stimulation therapy, posture state information, provide a user interface for receiving feedback or medication input from patient 12, display an active group of stimulation programs, and display operational status of patient programmer 30 or IMDs 14 or 26. For example, patient programmer 30 may provide a scrollable list of groups, and a scrollable list of programs within each group, via display 36. In addition, display may present a visible posture state indication.

Patient 12 or another user may interact with control pad 40 to navigate through items displayed on display 36. Patient 12 may press control pad 40 on any of arrows 42, 44, 46, and 48 in order to move between items presented on display 36 or move to another screen not currently shown on the display. In some examples, pressing the middle of control pad 40 selects any items highlighted in display 36. In other examples, scroll bars, a scroll wheel, individual buttons, or a joystick may perform the complete or partial functions of control pad 40. In alternative examples, control pad 40 may be a touch pad that allows patient 12 to move a cursor within the user interface displayed on display 36 to manage therapy.

Decrease button 50 and increase button 52 provide an input mechanism for patient 12. In general, activation of decrease button 50 (e.g., by pressing button 50) decreases the value of a highlighted stimulation parameter every time the decrease button is pressed. In contrast, activation of increase button 52 increases the value of a highlighted stimulation parameter one step every time the increase button is pressed. While buttons 50 and 52 may be used to control the value of any stimulation parameter, buttons 50 and 52 may also control patient feedback input. When either button 50 or 52 is selected, patient programmer 30 may initialize communication with IMD 14 or 26 to change therapy accordingly.

When depressed by patient 12, stimulation ON button 54 directs programmer 30 to generate a command for communication to IMD 14, where the command instructs IMD 14 to turn on stimulation therapy. Stimulation OFF button 56 turns off stimulation therapy when depressed by patient 12. Sync button 58 forces patient programmer 30 to communicate with IMD 14. When patient 12 enters an automatic posture response screen of the user interface, pressing sync button 58 turns on the automatic posture response to allow IMD 14 to automatically change therapy according to the posture state of patient 12. Pressing sync button 58 again, when the automatic posture response screen is displayed, turns off the automatic posture response. In the example of FIG. 2, patient 12 may use control pad 40 to adjust the volume, contrast, illumination, time, and measurement units of patient programmer 30.

In some examples, buttons 54 and 56 may be configured to perform operational functions related to stimulation therapy or the use of patient programmer 30. For example, buttons 54 and 56 may control the volume of audible sounds produced by programmer 20, wherein button 54 increases the volume and button 56 decreases the volume. Button 58 may be pressed to enter an operational menu that allows patient 12 to configure the user interface of patient programmer 30 to the desires of patient 12. For example, patient 12 may be able to select a language, backlight delay time, display brightness and contrast, or other similar options. In alternative examples, buttons 50 and 52 may control all operational and selection functions, such as those related to audio volume or stimulation therapy.

Patient programmer 30 may take other shapes or sizes not described herein. For example, patient programmer 30 may take the form of a clam-shell shape, similar to some cellular phone designs. When patient programmer 30 is closed, some or all elements of the user interface may be protected within the programmer. When patient programmer 30 is opened, one side of the programmer may contain a display while the other side may contain input mechanisms. In any shape, patient programmer 30 may be capable of performing the requirements described herein. Alternative examples of patient programmer 30 may include other input mechanisms such as a keypad, microphone, camera lens, or any other media input that allows the user to interact with the user interface provided by patient programmer 30.

In alternative examples, the buttons of patient programmer 30 may perform different functions than the functions provided in FIG. 2 and/or may have a different arrangement. In addition, other examples of patient programmer 30 may include different button layouts or different numbers of buttons. For example, patient programmer 30 may even include a single touch screen that incorporates all user interface functionality with a limited set of buttons or no other buttons.

Figure 3:
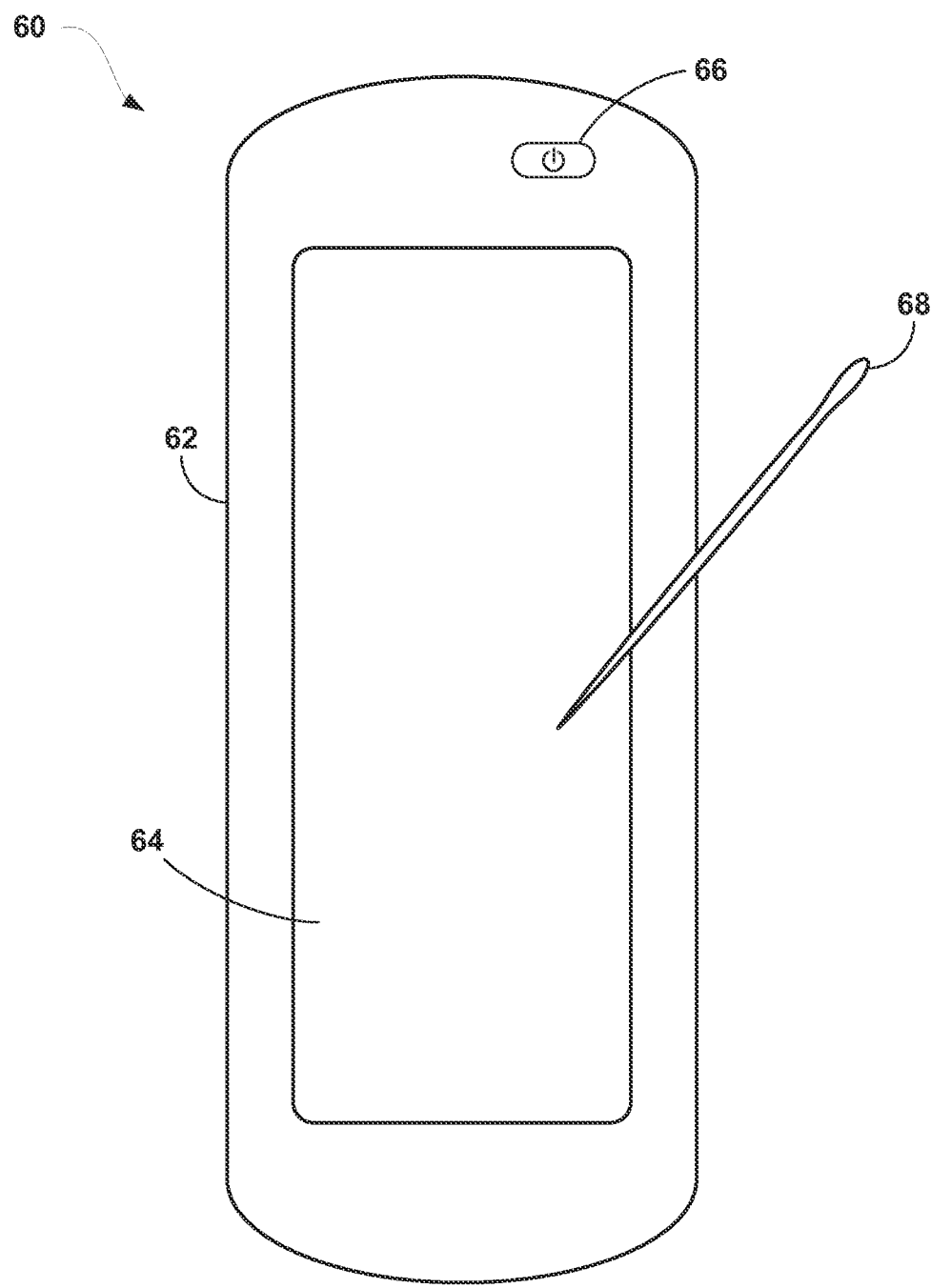
FIG. 3 is a conceptual diagram illustrating an example clinician programmer for programming stimulation therapy delivered by an implantable medical device.

FIG. 3 is a conceptual diagram illustrating an example clinician programmer 60 for programming stimulation therapy delivered by an IMD. Clinician programmer 60 is an example of external programmer 20 illustrated in FIGS. 1A, 1B and 1C and may be used with either IMD 14 or IMD 26. In alternative examples, clinician programmer 60 may be used with an external medical device. As shown in FIG. 3, clinician programmer 60 provides a user interface (not shown) for a user, such as a clinician, physician, technician, or nurse, to manage and program stimulation therapy. Clinician programmer 60 is protected by housing 62, which encloses circuitry necessary for clinician programmer 60 to operate.

Clinician programmer 60 includes display 64 and power button 66. In the example of FIG. 3, display 64 is a touch screen that accepts user input via touching certain areas within display 64. The user may use stylus 68 to touch display 64 and select virtual buttons, sliders, keypads, dials, or other such representations presented by the user interface shown by display 64. In some examples, the user may be able to touch display 64 with a finger, pen, or any other pointing device. In alternative examples, clinician programmer 60 may include one or more buttons, keypads, control pads, touch pads, or other devices that accept user input, similar to patient programmer 30.

In the illustrated example, clinician programmer 60 is a hand held device. Clinician programmer 60 may be used within the clinic or on in-house patient calls. Clinician programmer 60 may be used to communicate with multiple IMDs 14 and 26 within different patients. In this manner, clinician programmer 60 may be capable of communicating with many different devices and retain patient data separate from other patient data. In some examples, clinician programmer 60 may be a larger device that may be less portable, such as a notebook computer, workstation, or even a remote computer that communicates with IMD 14 or 26 via a remote telemetry device.

Most, if not all, of clinician programmer 60 functions may be completed via the touch screen of display 64. The user may program stimulation therapy (e.g., selecting stimulation parameter values), modify programs or groups, retrieve stored therapy data, retrieve posture state information from an IMD or another device, define posture states and other activity information, change the contrast and backlighting of display 64, or any other therapy related function. In addition, clinician programmer 60 may be capable of communicating with a networked server in order to send or receive an email or other message, retrieve programming instructions, access a help guide, send an error message, or perform any other function that may be beneficial to prompt therapy.

Housing 62 may be constructed of a polymer, metal alloy, composite, or combination material suitable to protect and contain components of clinician programmer 60. In addition, housing 62 may be partially or completely sealed such that fluids, gases, or other elements may not penetrate the housing and affect components therein. Power button 66 may turn clinician programmer 60 ON or OFF as desired by the user. Clinician programmer 60 may require a password, biometric input, or other security measure to be entered and accepted before the user can use clinician programmer 60.

Clinician programmer 60 may take other shapes or sizes not described herein. For example, clinician programmer 60 may take the form of a clam-shell shape, similar to some cellular phone designs. When clinician programmer 60 is closed, at least a portion of display 64 is protected within housing 62. When clinician programmer 60 is opened, one side of the programmer may contain a display while the other side may contain input mechanisms. In any shape, clinician programmer 60 may be capable of performing the requirements described herein.

Figure 4:
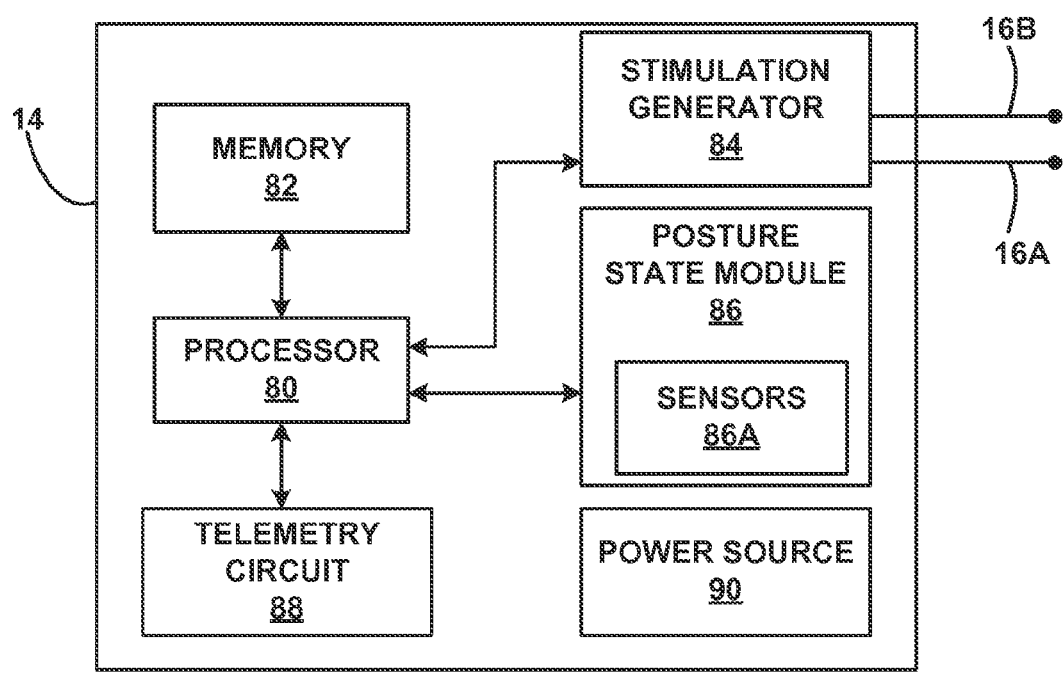
FIG. 4 is a functional block diagram illustrating various components of an example implantable electrical stimulator.

FIG. 4 is a functional block diagram illustrating various components of an IMD 14. In the example of FIG. 4, IMD 14 includes a processor 80, memory 82, posture state module 86, telemetry circuit 88, and power source 90. The stimulation generator 84 forms a therapy delivery module in this example, although in another example a drug delivery device may provide the therapy delivery module.

Memory 82 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media. Memory 82 may store instructions for execution by processor 80, stimulation therapy data, posture state information (e.g., posture state definitions, information associating posture states with therapy programs, and the like), posture state indications, and any other information regarding therapy or patient 12. Therapy information may be recorded for long-term storage and retrieval by a user, and the therapy information may include any data created by or stored in IMD 14. Memory 82 may include separate memories for storing instructions, posture state information, program histories, and any other data that may benefit from separate physical memory modules.

As one example, memory 82 may store instructions for execution by processor 80. Such instructions may cause the processor to operate in conjunction with posture state module 86 to control therapy based on posture state. Such instructions may allow for the modification of stimulation therapy delivered by IMD 14 based on a currently-detected posture state of the patient when the patient's velocity (e.g., movement velocity) is below a threshold. Such instructions may further allow for modification of stimulation therapy delivered by IMD 14 based on a most-recently-determined stable posture state of the patient when the patient's velocity is above the velocity threshold. In one example embodiment, memory 82 may further store instructions related to determining a patient's posture state and/or velocity. Techniques for determining a patient's velocity are described in detail below.

In another example memory may store one or more velocity thresholds for use according to techniques described herein. The thresholds may be programmable in some examples. Moreover, the threshold selected for use at a given time may be based on patient parameters and/or system parameters available within the system. Such parameters may include, for instance, posture state parameters sensed by sensors 86A, and/or system parameters such as time, day, etc. Other parameters may include physiological parameters sensed by sensors 86A that are used to select the threshold in use at a given time. This is described further below.

Processor 80 controls stimulation generator 84 to deliver electrical stimulation via electrode combinations formed by electrodes in one or more electrode arrays. For example, stimulation generator 84 may deliver electrical stimulation therapy via electrodes on one or more leads 16, e.g., as stimulation pulses or continuous waveforms. Components described as processors within IMD 14, external programmer 20 or any other device described in this disclosure may each comprise one or more processors, such as one or more microprocessors, digital signal processors (DSPs), application specific integrated circuits (ASICs), field programmable gate arrays (FPGAs), programmable logic circuitry, or the like, either alone or in any suitable combination. The functions attributed to processors described herein may be embodied as software, firmware, hardware, or any combination thereof.

Stimulation generator 84 may include stimulation generation circuitry to generate stimulation pulses or continuous waveforms and, in some examples, switching circuitry to switch the stimulation across different electrode combinations, e.g., in response to control by processor 80. In particular, processor 80 may control the switching circuitry on a selective basis to cause stimulation generator 84 to deliver electrical stimulation to selected electrode combinations and to shift the electrical stimulation to different electrode combinations in a first direction or a second direction when the therapy must be delivered to a different location within patient 12. In other examples, stimulation generator 84 may include multiple current sources to drive more than one electrode combination at one time. In this case, stimulation generator 84 may decrease current to the first electrode combination and simultaneously increase current to the second electrode combination to shift the stimulation therapy.

An electrode configuration, e.g., electrode combination and associated electrode polarities, may be represented by a data stored in a memory location, e.g., in memory 82, of IMD 14. Processor 80 may access the memory location to determine the electrode combination and control stimulation generator 84 to deliver electrical stimulation via the indicated electrode combination. To adjust electrode combinations, amplitudes, pulse rates, or pulse widths, processor 80 may command stimulation generator 84 to make the appropriate changes to therapy according to instructions within memory 82 and rewrite the memory location to indicate the changed therapy. In other examples, rather than rewriting a single memory location, processor 80 may make use of two or more memory locations.

As previously mentioned, in some example, the instructions stored in memory 82 may allow processor to control stimulation generator 84 to make parameter adjustments based on a patient's most-recent stable posture state when the patient has entered a period when the patient's velocity has exceeded a velocity threshold.

When activating stimulation, processor 80 may access not only the memory location specifying the electrode combination but also other memory locations specifying various stimulation parameters such as voltage or current amplitude, pulse width, pulse rate, waveform shape and/or other parameters. Stimulation generator 84, e.g., under control of processor 80, then makes use of the electrode combination and parameters in formulating and delivering the electrical stimulation to patient 12.

According to examples described herein, such stimulation parameters may be adjusted to modify stimulation therapy delivered by IMD 14 based on the detected posture state of patient 12. In some examples, processor 80 may detect a posture state of patient 12 via posture state module 86 that indicates that a modification of the stimulation therapy is appropriate, e.g., according to instructions stored in memory 82. In one example, posture state module may be configured to determine a posture state of the patient to be used in controlling an aspect of the system, which may include the control of therapy delivery. The posture state determined by posture state module may be based on one or more posture state parameters, such as parameters sensed by sensors 86A. Such parameters may describe the patient's position in three-dimensional space and/or an activity state that the patient is undergoing. The posture state determined by the posture state module for use in controlling the system may also be determined based on a relationship between a velocity of the patient and a velocity threshold. As previously described, for example, the posture state determined for use in controlling therapy adjustment may be a patient's most-recent stable posture state if the patient's velocity exceeds a threshold. On the other hand, the posture state determined for use in controlling therapy adjustment may be a patient's current posture state if the patient's velocity is at, or below, a threshold in one instance.

In one embodiment, each time a patient's stable posture state is determined by posture state module 86 based on data from sensors 86A, that stable posture state is recorded in a storage device of IMD 14 (e.g., in memory 82) or another storage device of the system (e.g., storage device of programmer 30, 60. That storage device need only store the most-recent stable posture state or could instead record a history of multiple stable posture states (e.g., all posture stable posture states assumed by the patient over the last 24 hours). Time and/or date information could also be stored along with such history data, if desired.

When the patient's velocity rises above a corresponding velocity threshold, posture state module 86 and/or processor 80 could, in one embodiment, retrieve the most-recent stable posture state for use by the system in controlling therapy or some other system function. Thus, while posture state module 86 could re-calculate a previous stable posture state based on previously-recorded raw sensor data that reflects a patient's previous posture state, in another embodiment, posture state module 86 may merely retrieve an indication of the most-recent posture state when the patient has entered a relatively high-velocity period.

Processor 80 may access instructions for modifying the stimulation therapy based on the patient 12 posture state, e.g., by changing from a stimulation program appropriate for the previous posture state to a stimulation program appropriate for patient's current posture state.

Depending on the parameter values defined by the respective program, an adjustment may be made to one or more or the parameter values as a result of a detected change in patient posture. In one example, processor 80 may control therapy to be modified based on a patient's current posture state if that current posture state is determined to be stable such that a velocity of the patient is at, or below, a velocity threshold. On the other hand, if the velocity of the patient rises above the velocity threshold, therapy may be controlled based on the most-recent stable posture state rather than a current posture state. In addition, other aspects of the system may be controlled based on a most-recent stable posture state when the patient's velocity exceeds a threshold in some embodiments. For instance, in some cases, monitoring of some physiological parameters (e.g., blood pressure or resting heart rate) may be temporarily ceased if the patient's velocity rises above a threshold.

As discussed above, electrical parameters may be varied based on either a current posture state or a most-recent stable posture state of the patient. An exemplary range of electrical stimulation parameters likely to be effective in treating chronic pain, e.g., when applied to spinal cord 18, are listed below. While stimulation pulses are described, stimulation signals may be of any of a variety of forms such as sine waves or the like.

Pulse Rate: between approximately 0.5 Hz and approximately 1200 Hz, more preferably between approximately 5 Hz and approximately 250 Hz, and still more preferably between approximately 30 Hz and approximately 130 Hz.

Amplitude: between approximately 0.1 volts and approximately 50 volts, more preferably between approximately 0.5 volts and approximately 20 volts, and still more preferably between approximately 1 volt and approximately 10 volts. In other examples, a current amplitude may be defined as the biological load in the voltage that is delivered. For example, the range of current amplitude may be between approximately 0.1 milliamps (mA) and approximately 50 mA.

Pulse Width: between approximately 10 microseconds and approximately 5000 microseconds, more preferably between approximately 100 microseconds and approximately 1000 microseconds, and still more preferably between approximately 180 microseconds and approximately 450 microseconds.

In other applications, different ranges of parameter values may be used. For DBS, as one example, alleviation or reduction of symptoms associated with Parkinson's disease, essential tremor, epilepsy, psychiatric disorders or other disorders may make use of stimulation having a pulse rate in the range of approximately 0.5 to approximately 1200 Hz, such as between approximately 5 to approximately 250 Hz, or between approximately 30 to approximately 185 Hz, and a pulse width in the range of approximately 10 microseconds and 5000 microseconds, such as between approximately 60 microseconds and approximately 1000 microseconds, or between approximately 60 microseconds and approximately 450 microseconds, or between approximately 60 microseconds and approximately 150 microseconds. Amplitude ranges such as those described above with reference to SCS, or other amplitude ranges, may be used for different DBS applications.

Processor 80 accesses stimulation parameters in memory 82, e.g., as programs and groups of programs. Upon selection of a particular program group, processor 80 may control stimulation generator 84 to generate and deliver stimulation according to the programs in the groups, e.g., simultaneously or on a time-interleaved basis. A group may include a single program or multiple programs. As mentioned previously, each program may specify a set of stimulation parameters, such as amplitude, pulse width and pulse rate. In addition, each program may specify a particular electrode combination for delivery of stimulation. Again, the electrode combination may specify particular electrodes in a single array or multiple arrays, e.g., on a single lead or among multiple leads. Processor 80 also may control telemetry circuit 88 to send and receive information to and from external programmer 20. For example, telemetry circuit 88 may send information to and receive information from patient programmer 30.

Posture state module 86 allows IMD 14 to sense the patient posture state, e.g., posture, activity or any other static position or motion of patient 12. In the example of FIG. 4, posture state module 86 includes one or more posture state sensors 86A to sense one or more posture state parameters indicative of a posture state of the patient. Such sensors may include, but are not limited to, one or more accelerometers, such as three-axis accelerometers, capable of detecting static orientation or vectors in three-dimensions. Example accelerometers include a micro-electro-mechanical accelerometer. In other examples, posture state module 86 may alternatively or additionally include one or more gyroscopes, piezoelectric crystals, pressure transducers or other sensors to sense posture state parameters indication of the posture state of patient 12. Posture state information generated by posture state module 86 and processor 80 may correspond to an activity and/or posture undertaken by patient 12 or a gross level of physical activity, e.g., activity counts based on footfalls or the like.

Posture state information from posture state module 86 may be stored in memory 82 for later review by a clinician, used to adjust therapy, present a posture state indication to patient 12 (e.g., via patient programmer 30), or some combination thereof. As an example, processor 80 may record the posture state parameter value, or output, of the three-axis accelerometer and assign the posture state parameter value to a certain predefined posture indicated by the posture state parameter value. In this manner, IMD 14 may be able to track how often patient 12 remains within a certain posture. IMD 14 may also store which group or program was being used to deliver therapy when patient 12 was in the sensed posture. As another example, processor 80 may record a patient's most-recent stable posture state for possible use later should the patient enter a period of high-velocity such that this stable posture state will be retrieved to control therapy delivery or some other aspect of the system.

Further, processor 80 may also adjust therapy for a new posture state when posture state module 86 indicates that patient 12 has in fact changed postures. Therefore, IMD 14 may be configured to provide posture responsive stimulation therapy to patient 12. Stimulation adjustments in response to posture state may be automatic or semi-automatic (subject to patient approval). In many cases, fully automatic adjustments may be desirable so that IMD 14 may react more quickly to posture state changes.

A posture state parameter value from posture state module 86 that indicates the posture state may constantly vary throughout the day of patient 12. However, a certain activity (e.g., walking, running, or biking) or a posture (e.g., standing, sitting, or lying down) may include multiple posture state parameter values from posture state module 86. Memory 82 may include definitions for each posture state of patient 12. In one example, the definition of each posture state may be illustrated as a cone in three-dimensional space. Whenever the posture state parameter value, e.g., a vector, from a sensor 86A (e.g., a three-axis accelerometer) of posture state module 86 resides within a predefined cone, processor 80 indicates that patient 12 is in the posture state associated with the cone. In other examples, posture state parameter value from the three-axis accelerometer may be compared to a look-up table or equation to determine the posture state in which patient 12 currently resides.

Posture responsive stimulation may allow IMD 14 to implement a certain level of automation in therapy adjustments. Automatically adjusting stimulation may free patient 12 from the constant task of manually adjusting therapy each time patient 12 changes posture or starts and stops a certain posture state. Such manual adjustment of stimulation parameters can be tedious, requiring patient 12 to, for example, depress one or more keys of patient programmer 30 multiple times during the patient posture state to maintain adequate symptom control. In some examples, patient 12 may eventually be able to enjoy posture state responsive stimulation therapy without the need to continue making changes for different postures via patient programmer 30. Instead, patient 12 may transition immediately or over time to fully automatic adjustments based on posture state.

Although posture state module 86 is described as containing one or more sensors 86A which may be a three-axis accelerometer, posture state module 86 may alternatively contain multiple single-axis accelerometers, dual-axis accelerometers, three-axis accelerometers, or some combination thereof. In some examples, an accelerometer or other sensor may be located within or on IMD 14 or on one or more of leads 16 (e.g., at the distal tip or at an intermediate position), an additional sensor lead positioned somewhere within patient 12, within an independent implantable sensor, or even worn on patient 12. For example, one or more microsensors may be implanted within patient 12 to communicate posture state information wirelessly to IMD 14. In this manner, the patient 12 posture state may be determined from multiple posture state sensors placed at various locations on or within the body of patient 12.

In other examples, posture state module 86 in conjunction with sensors 86A may additionally or alternatively be configured to sense one or more physiological parameters of patient 12. For example, physiological parameters may include heart rate, electromyography (EMG), an electroencephalogram (EEG), an electrocardiogram (ECG), temperature, respiration rate, or pH. These physiological parameters may be used by processor 80, in some examples, to confirm or reject changes in sensed posture state that may result from vibration, patient travel (e.g., in an aircraft, car or train), or some other false positive of posture state.

In one example, sensing of these physiological parameters can be controlled based on a posture state of the patient. For instance, it may be desirable to only collect some physiologic parameters when the patient is in a stable posture state. Thus, collection of these parameters may be suspended when the patient's velocity rises about a velocity threshold. Alternatively, some parameters may be most usefully-collected when the patient has entered a time of high velocity. In this situation, when the system determines the patient's velocity exceeds the threshold, collection of these parameters may be enabled.

In some examples, processor 80 processes the analog output of the posture state sensor in posture state module 86 to determine activity and/or posture data. For example, where the posture state sensor comprises an accelerometer, processor 80 or a processor of posture state module 86 may process the raw signals provided by the posture state sensor to determine activity counts. In some examples, processor 80 may process the signals provided by the posture state sensor to determine velocity of motion information along each axis.

In one example, each of the x, y, and z signals provided by the posture state sensor has both a DC component and an AC component. The DC component describes the gravitational force exerted upon the sensor and can thereby be used to determine orientation of the sensor within the gravitational field of the earth. Assuming the orientation of the sensor is relatively fixed with respect to the patient, the DC components of the x, y and z signals may be utilized to determine the patient's orientation within the gravitational field, and hence to determine the posture of the patient.

The AC component of the x, y and z signals yields information about patient motion. In particular, the AC component of a signal may be used to derive a value for an activity describing the patient's motion. This activity may involve a level, direction of motion, or acceleration of the patient.

One method for determining the patient activity is by determining an activity count. An activity count may be used to indicate the activity or activity level of patient 12. For example, a signal processor may sum the magnitudes of the AC portion of an accelerometer signal for N consecutive samples. For instance, assuming sampling occurs as 25 Hz, N may be set to 25, so that count logic provides the sum of the samples that are obtained in one second. This sum may be referred to as an "activity count". The number "N" of consecutive samples may be selected by the processor based on the current posture state, if desired. The activity count may be the activity portion of the activity parameter value that is added to the posture portion. The resulting activity parameter value may then incorporate both activity and posture to generate an accurate indication of the activity of patient 12.

As another example, the activity parameter value may be defined as describing direction of motion. This activity parameter value may be associated with a vector and an associated tolerance, which may be a distance from the vector. Another example of an activity parameter value relates to acceleration. The value quantifying a level of change of motion over time in a particular direction may be associated with this parameter referenced in the activity parameter value.

IMD 14 wirelessly communicates with external programmer 20, e.g., patient programmer 30 or clinician programmer 60, or another device by radio frequency (RF) communication or proximal inductive interaction of IMD 14 with external programmer 20. Telemetry circuit 88 may send information to and receive information from external programmer 20 on a continuous basis, at periodic intervals, at non-periodic intervals, or upon request from the stimulator or programmer. To support RF communication, telemetry circuit 88 may include appropriate electronic components, such as amplifiers, filters, mixers, encoders, decoders, and the like.

Power source 90 delivers operating power to the components of IMD 14. Power source 90 may include a small rechargeable or non-rechargeable battery and a power generation circuit to produce the operating power. Recharging may be accomplished through proximal inductive interaction between an external charger and an inductive charging coil within IMD 14. In some examples, power requirements may be small enough to allow IMD 14 to utilize patient motion and implement a kinetic energy-scavenging device to trickle charge a rechargeable battery. In other examples, traditional batteries may be used for a limited period of time. As a further alternative, an external inductive power supply could transcutaneously power IMD 14 when needed or desired.

Figure 5:
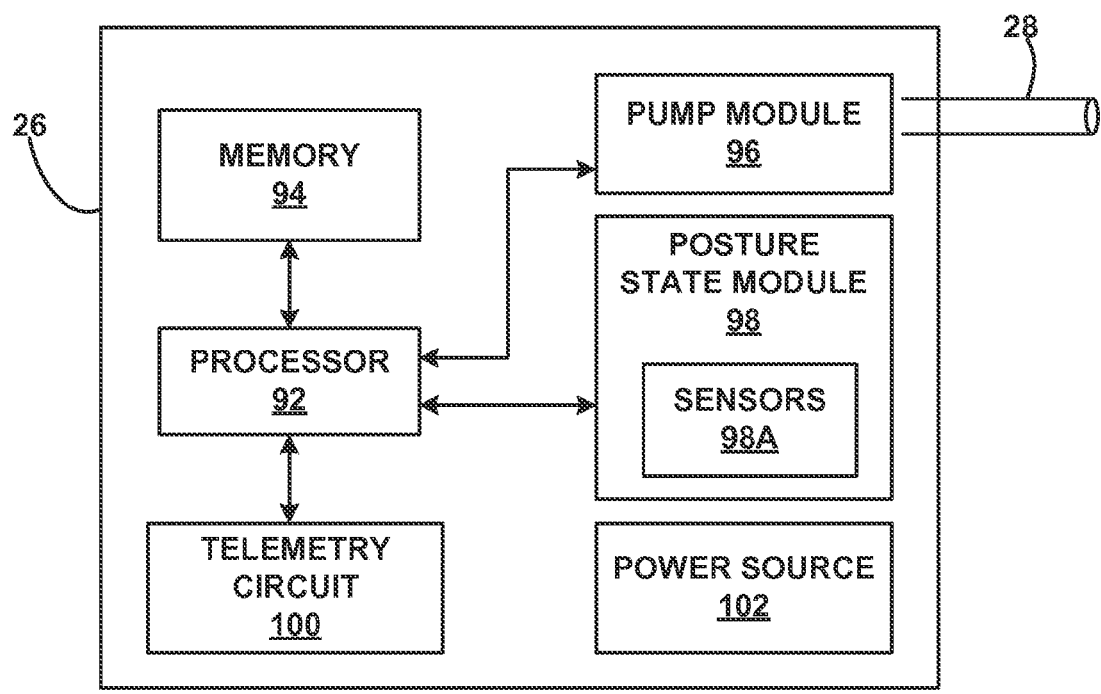
FIG. 5 is a functional block diagram illustrating various components of an example implantable drug pump.

FIG. 5 is a functional block diagram illustrating various components of an IMD 26, which delivers a therapeutic agent to patient 12. IMD 26 is a drug pump that operates substantially similar to IMD 14 of FIG. 4, but delivers a therapeutic agent instead of electrical stimulation. IMD 26 includes processor 92, memory 94, pump module 96, posture state module 98, telemetry circuit 100, and power source 102. Instead of stimulation generator 84 of IMD 14, IMD 26 includes pump module 96 for delivering drugs or some other therapeutic agent via catheter 28. Pump module 96, which may be characterized as a therapy module, may include a reservoir to hold the drug and a pump mechanism to force drug out of catheter 28 and into patient 12.

Processor 92 controls pump module 96 according to therapy instructions stored within memory 94. For example, memory 94 may contain the programs or groups of programs that define the drug delivery therapy for patient 12. A program may indicate the bolus size or flow rate of the drug, and processor 92 may accordingly deliver therapy. Processor 92 may also use posture state information from posture state 98 to adjust drug delivery therapy when patient 12 changes posture states, e.g., adjusts his or her posture.

Figure 6:
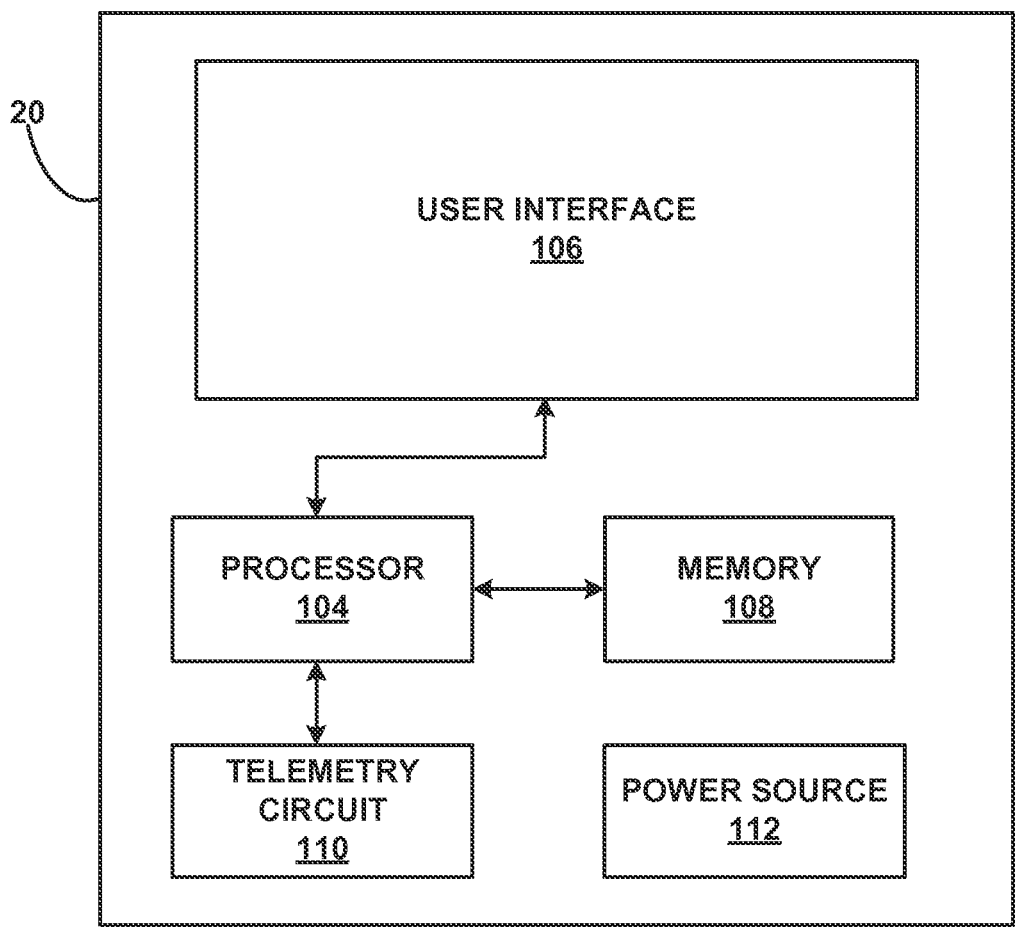
FIG. 6 is a functional block diagram illustrating various components of an example external programmer for an implantable medical device.

FIG. 6 is a functional block diagram illustrating various components of an external programmer 20 for IMDs 14 or 26. Programmer 20 may be a handheld computing device, a workstation or another dedicated or multifunction computing device. For example, programmer 20 may be a general purpose computing device (e.g., a personal computer, personal digital assistant (PDA), cell phone, and so forth) or may be a computing device dedicated to programming the IMD. As shown in FIG. 6, external programmer 20 includes processor 104, memory 108, telemetry circuit 110, user interface 106, and power source 112. External programmer 20 may be embodied as patient programmer 30 (FIG. 2) or clinician programmer 60 (FIG. 3).

Processor 104 processes instructions by memory 108 and may store user input received through user interface 106 into the memory when appropriate for the current therapy. In addition, processor 104 provides and supports any of the functionality described herein with respect to each example of user interface 106. Processor 104 may comprise any one or more of a microprocessor, DSP, ASIC, FPGA, or other digital logic circuitry, and the functions attributed to programmer 104 may be embodied as software, firmware, hardware or any combination thereof.

Memory 108 may include any one or more of a RAM, ROM, EEPROM, flash memory or the like. Memory 108 may include instructions for operating user interface 106, telemetry module 110 and managing power source 112. Memory 108 may store program instructions that, when executed by processor 104, cause processor 104 and programmer 20 to provide the functionality ascribed to them herein. Memory 108 also includes instructions for generating and delivering programming commands to IMD 14, such as a programming command that instructs IMD 14 to activate or deactivate a posture responsive therapy mode. Memory 108 may also include a removable memory portion that may be used to provide memory updates or increases in memory capacities. A removable memory may also allow patient data to be easily transferred to another computing device, or to be removed before programmer 20 is used to program therapy for another patient.

A clinician, patient 12 or another user (e.g., a patient caretaker) interacts with user interface 106 in order to manually change the stimulation parameter values of a program, change programs within a group, turn posture responsive stimulation ON or OFF, view therapy information, view posture state information, or otherwise communicate with IMDs 14 or 26.

User interface 106 may include a screen and one or more input mechanisms, such as buttons as in the example of patient programmer 30 that allow external programmer 20 to receive input from a user. Alternatively, user interface 106 may additionally or only utilize a touch screen display, as in the example of clinician programmer 60. The screen may be a liquid crystal display (LCD), dot matrix display, organic light-emitting diode (OLED) display, touch screen, or any other device capable of delivering and/or accepting information. For visible posture state indications, a display screen may suffice. For audible and/or tactile posture state indications, programmer 20 may further include one or more audio speakers, voice synthesizer chips, piezoelectric buzzers, or the like.

Telemetry circuit 110 allows the transfer of data to and from IMD 14, or IMD 26. Telemetry circuit 110 may communicate automatically with IMD 14 at a scheduled time or when the telemetry circuit detects the proximity of the stimulator. Alternatively, telemetry circuit 110 may communicate with IMD 14 when signaled by a user through user interface 106. To support RF communication, telemetry circuit 110 may include appropriate electronic components, such as amplifiers, filters, mixers, encoders, decoders, and the like. Power source 112 may be a rechargeable battery, such as a lithium ion or nickel metal hydride battery. Other rechargeable or conventional batteries may also be used. In some cases, external programmer 20 may be used when coupled to an alternating current (AC) outlet, i.e., AC line power, either directly or via an AC/DC adapter.

Although not shown in FIG. 6, in some examples, external programmer 20 may include a charger module capable of recharging a power source, such as a rechargeable battery that may be included in power source 90 of IMD 14. Hence, in some cases, the programmer may be integrated with recharging components to form a combined programmer/recharger unit.

Figure 7:
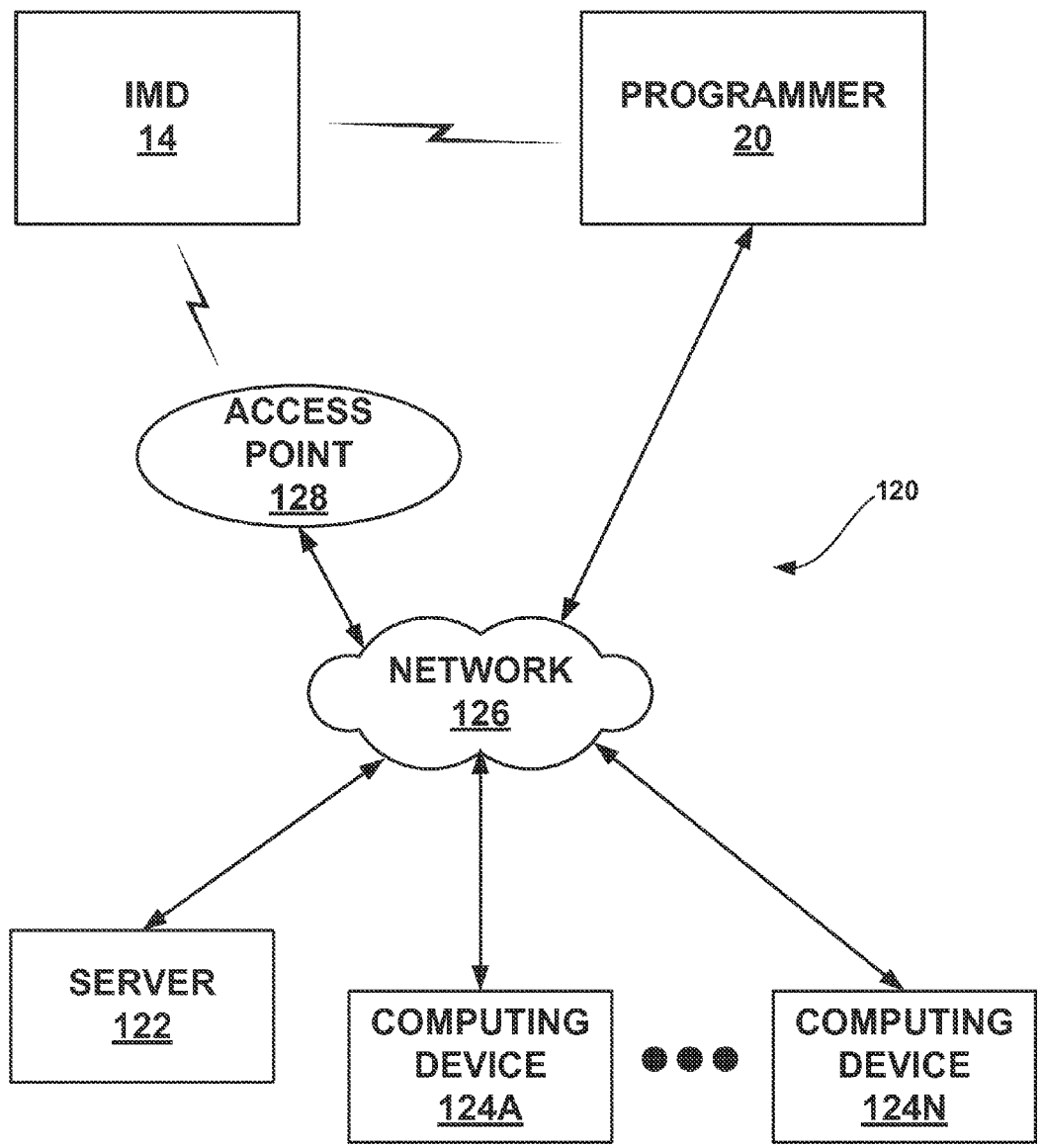
FIG. 7 is a block diagram illustrating an example system that includes an external device, such as a server, and one or more computing devices that are coupled to an implantable medical device and external programmer shown in FIGS. 1A-1C via a network.

FIG. 7 is a block diagram illustrating an example system 120 that includes an external device, such as a server 122, and one or more computing devices 124A-124N, that are coupled to IMD 14 and external programmer 20 shown in FIGS. 1A-1C via a network 126. In this example, IMD 14 may use its telemetry circuit 88 (FIG. 4) to communicate with external programmer 20 via a first wireless connection, and to communication with an access point 128 via a second wireless connection. In other examples, IMD 26 may also be used in place of IMD 14, and external programmer 20 may be either patient programmer 30 or clinician programmer 60.

In the example of FIG. 7, access point 128, external programmer 20, server 122, and computing devices 124A-124N are interconnected, and able to communicate with each other, through network 126. In some cases, one or more of access point 128, external programmer 20, server 122, and computing devices 124A-124N may be coupled to network 126 through one or more wireless connections. IMD 14, external programmer 20, server 122, and computing devices 124A-124N may each comprise one or more processors, such as one or more microprocessors, DSPs, ASICs, FPGAs, programmable logic circuitry, or the like, that may perform various functions and operations, such as those described in this disclosure.

Access point 128 may comprise a device, such as a home monitoring device, that connects to network 126 via any of a variety of connections, such as telephone dial-up, digital subscriber line (DSL), or cable modem connections. In other examples, access point 128 may be coupled to network 126 through different forms of connections, including wired or wireless connections.

During operation, IMD 14 may collect and store various forms of data. For example, IMD 14 may collect sensed posture state information during therapy that indicate how patient 12 moves throughout each day. In some cases, IMD 14 may directly analyze the collected data to evaluate the posture state of the patient and/or how the patient transitions between posture states. For instance, IMD 14 may collect data that indicates when the patient has a movement velocity that exceeds one or more thresholds. This data may be time and/or date stamped to allow a clinician to better understand the activity patterns of a patient, and may further provide insights into how the IMD 14 is changing therapy in response to the posture states. Other collected information may include percentages of time patient 12 was in each identified posture.

In other cases, however, IMD 14 may send stored data relating to posture state information to external programmer 20 and/or server 122, either wirelessly or via access point 128 and network 126, for remote processing and analysis. For example, IMD 14 may sense, process, trend and evaluate the sensed posture state information. This communication may occur in real time, and network 126 may allow a remote clinician to review the current patient posture state by receiving a presentation of a posture state indication on a remote display, e.g., computing device 124A. Alternatively, processing, trending and evaluation functions may be distributed to other devices such as external programmer 20 or server 122, which are coupled to network 126. In addition, posture state information may be archived by any of such devices, e.g., for later retrieval and analysis by a clinician.

In some cases, IMD 14, external programmer 20 or server 122 may process posture state information or raw data and/or therapy information into a displayable posture state report, which may be displayed via external programmer 20 or one of computing devices 124A-124N. The posture state report may contain trend data for evaluation by a clinician, e.g., by visual inspection of graphic data. In some cases, the posture state report may include the number of activities patient 12 conducted, a percentage of time patient 12 was in each posture state, the average time patient 12 was continuously within a posture state, what group or program was being used to deliver therapy during each activity, the number of adjustments to therapy during each respective posture state, or any other information relevant to patient 12 therapy, based on analysis and evaluation performed automatically by IMD 14, external programmer 20 or server 122. A clinician or other trained professional may review and/or annotate the posture state report, and possibly identify any problems or issues with the therapy that should be addressed.

In the manner of FIG. 7, a clinician, physician, technician, or even patient 12, may review objectivity data with respect to the posture states of patient 12. The objectivity data may be sleep quality information or proportional posture information that indicates how patient 12 has been moving during the symptom diagnosis or delivered therapy. Such data may indicate when the patient's velocity, which may be either movement or activity velocity, has exceeded a selected threshold. The user may remotely monitor the progress and trends of patient 12, limiting the number of times that patient 12 may need to physically visit the clinician. The remote monitoring supported by system 120 may also reduce the time needed to find efficacious therapy parameters by allowing the clinician to more frequently monitor sleep quality information and proportional posture information. Any of the user interfaces described herein with respect to patient programmer 30 or clinician programmer 60 may also be presented via any of computing devices 124A-124N.

In some cases, server 122 may be configured to provide a secure storage site for archival of posture state information that has been collected from IMD 14 and/or external programmer 20. Network 126 may comprise a local area network, wide area network, or global network, such as the Internet. In some cases, external programmer 20 or server 122 may assemble posture state information in web pages or other documents for viewing by trained professionals, such as clinicians, via viewing terminals associated with computing devices 124A-124N. System 120 may be implemented, in some aspects, with general network technology and functionality similar to that provided by the Medtronic CareLink® Network developed by Medtronic, Inc., of Minneapolis, Minn.

Although some examples of the disclosure may involve posture state information and data, system 120 may be employed to distribute any information relating to the treatment of patient 12 and the operation of any device associated therewith. For example, system 120 may allow therapy errors or device errors to be immediately reported to the clinician. In addition, system 120 may allow the clinician to remotely intervene in the therapy and reprogram IMD 14, patient programmer 30, or communicate with patient 12. In an additional example, the clinician may utilize system 120 to monitor multiple patients and share data with other clinicians in an effort to coordinate rapid evolution of effective treatment of patients.

Furthermore, although the disclosure is described with respect to SCS therapy, such techniques may be applicable to IMDs that convey other therapies in which posture state information is important, such as, e.g., DBS, pelvic floor stimulation, gastric stimulation, occipital stimulation, functional electrical stimulation, and the like. Also, in some aspects, techniques for evaluating posture state information, as described in this disclosure, may be applied to IMDs that are generally dedicated to sensing or monitoring and do not include stimulation or other therapy components. For example, an implantable monitoring device may be implanted in conjunction with an implantable stimulation device, and be configured to evaluate sensing integrity of leads or electrodes associated with the implantable monitoring device based on sensed signals evoked by delivery of stimulation by the implantable stimulation device.

Next, various example techniques for performing posture state detection will be discussed primarily in reference to IMD 14 of FIG. 4. It will be understood that these techniques apply to IMD 26 of FIG. 5, and the reference to FIG. 4 is for brevity only and should not be considered limiting.

Figure 8A:
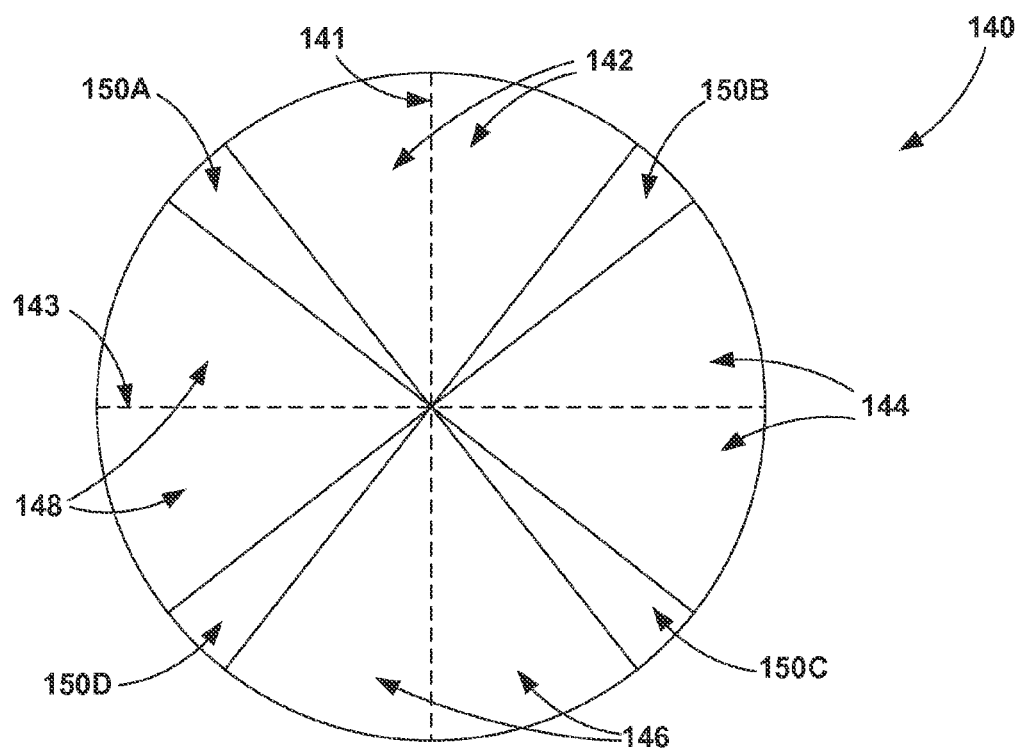
FIGS. 8A-8C are conceptual illustrations of example posture state spaces within which postures state reference data may define the posture state of a patient.
Figure 8B:
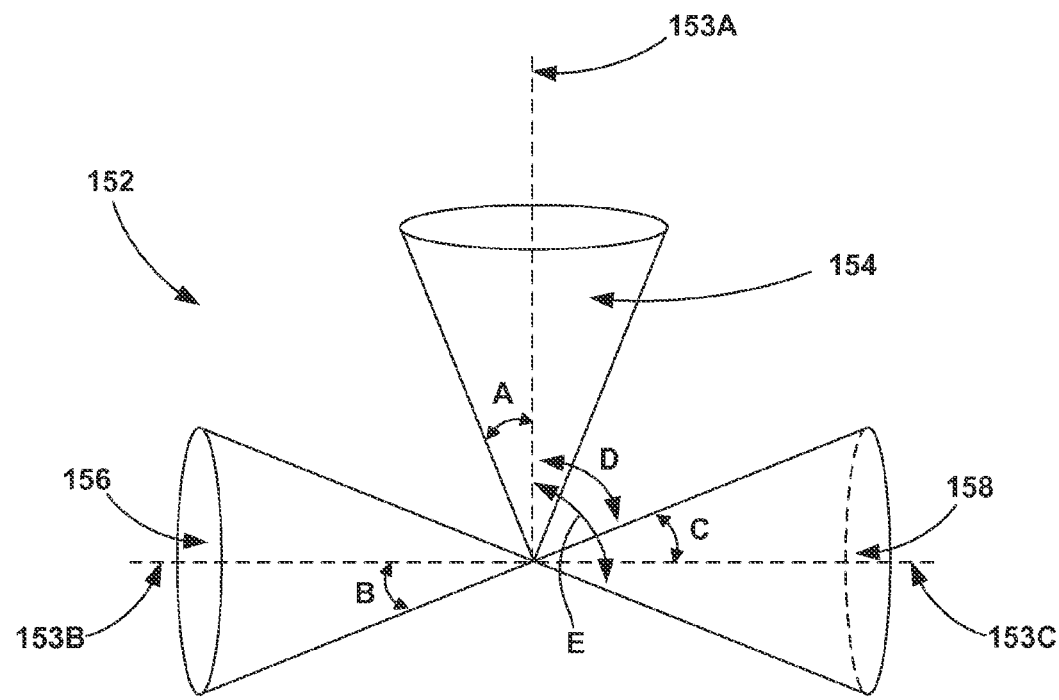
Figure 8C:
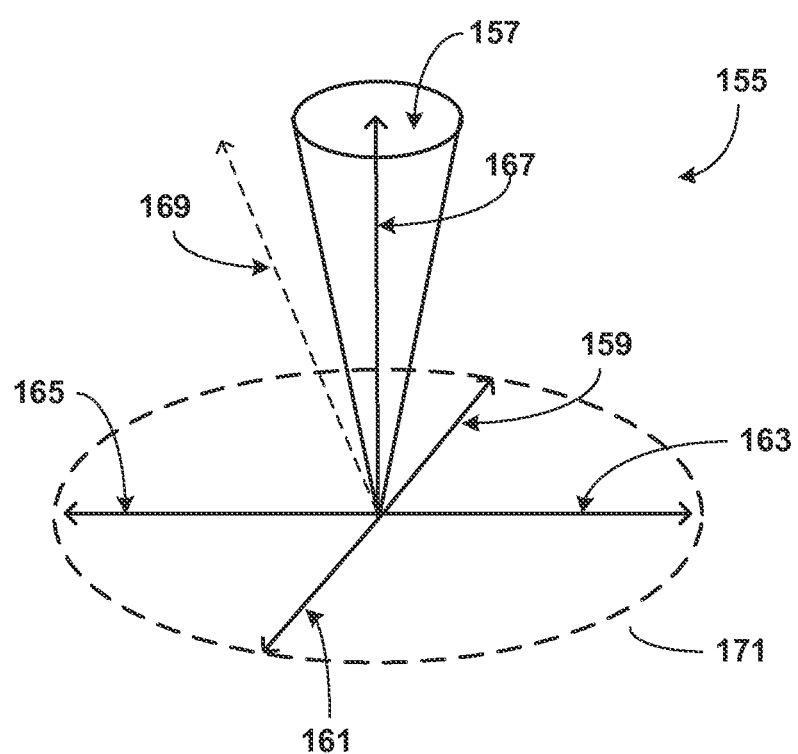

FIGS. 8A-8C are conceptual illustrations of posture state spaces 140, 152, 155 within which posture state reference data may define the posture state of patient 12. Posture state reference data may define certain regions associated with particular posture states of patient 12 within the respective posture state spaces 140, 152, 155. The output of one or more posture state sensors may be analyzed by posture state module 86 with respect to posture state spaces 140, 152, 155 to determine the posture state of patient 12. For example, if the output of one or more posture state sensors is within a particular posture region defined by posture state reference data, posture state module 86 may determine that patient 12 is within the posture state associated with the respective posture state region.

In some cases, one or more posture state regions may be defined as posture state cones. Posture state cones may be used to define a posture state of patient 12 based on the output from a posture state sensor of a posture state according to an example method for posture state detection. A posture state cone may be centered about a posture state reference coordinate vector that corresponds to a particular posture state. In the examples of FIGS. 8A and 8B, the posture state module 86 of IMD 14 may use a posture state sensor, e.g., a three-axis accelerometer that provides data indicating the posture state of patient 12, to sense posture vectors. While the sensed data may be indicative of any posture state, postures of patient 12 will generally be used below to illustrate the concept of posture cones. As shown in FIG. 8A, posture state space 140 represents a vertical plane dividing patient 12 from left and right sides, or the sagittal plane. A posture state parameter value from two axes of the posture state sensor may be used to determine the current posture state of patient 12 according to the posture state space 140. The posture state data may include x, y and z coordinate values.

In one example, a posture cone may be defined by a reference coordinate vector for a given posture state in combination with a distance or angle defining a range of coordinate vectors within a cone surrounding the posture reference coordinate vector. Alternatively, a posture cone may be defined by a reference coordinate vector and a range of cosine values computed using the reference coordinate vector as an adjacent vector and any of the outermost vectors of the cone as a hypotenuse vector. If a sensed posture state vector is within an applicable angle from the reference coordinate vector, or if the sensed posture state vector and the reference coordinate vector are within a predetermined distance of one another (e.g., as indicated by the produce a cosine value being in a specified cosine range), then posture state vector is determined to reside within the posture cone defined by the reference coordinate vector. In one example, the distance between the sensed posture state vector and the reference coordinate vector may alternatively be an absolute distance, a Euclidean distance, a city-block distance, some other trigonometric description besides cosine (e.g., sine), and so on.

Posture state space 140 is segmented into different posture cones that are indicative of a certain posture state of patient 12. In the example of FIG. 8A, upright cone 142 indicates that patient 12 is sitting or standing upright, lying back cone 148 indicates that patient 12 is lying back down, lying front cone 144 indicates that patient 12 is lying chest down, and inverted cone 146 indicates that patient 12 is in an inverted position. Other cones may be provided, e.g., to indicate that patient 12 is lying on the right side or left side. For example, a lying right posture cone and a lying left posture cone positioned outside of the sagittal plane illustrated in FIG. 8A. In particular, the lying right and lying left posture cones may be positioned in a coronal plane substantially perpendicular to the sagittal plane illustrated in FIG. 8A. For ease of illustration, lying right and lying left cones are not shown in FIG. 8A.

Vertical axis 141 and horizontal axis 143 are provided for orientation of posture state area 140, and are shown as orthogonal for purposes of illustration. However, posture cones may have respective posture reference coordinate vectors that are not orthogonal in some cases. For example, individual reference coordinate vectors for cones 142 and 146 may not share the same axis, and reference coordinate vectors for cones 144 and 148 may not share the same axis. Also, reference coordinate vectors for cones 144 and 148 may or may not be orthogonal to reference coordinates vectors for cones 142, 146. Therefore, although orthogonal axes are shown in FIG. 8A for purposes of illustration, respective posture cones may be defined by individualized reference coordinate vectors for the cones.

IMD 14 may monitor the posture state parameter value of the posture state sensor to produce a sensed coordinate vector (also referred herein as a "detected vector") and identify the current posture of patient 12 by identifying in which cone the sensed coordinated vector generated by the posture state sensor module 86 resides. For example, if the posture state parameter value corresponds to a sensed coordinate vector that falls within lying front cone 144, IMD 14 determines that patient 12 is lying down on his/her chest. IMD 14 may store this posture information as a determined posture state or as raw output from the posture state sensor, change therapy according to this determined posture state, and/or control some other aspect of the system based on the determined posture state (e.g., control physiological sensing.) Additionally, IMD 14 may communicate the posture information to patient programmer 30 so that the patient programmer can present a posture state indication to patient 12.

In addition to the posture cones, posture state area 140 may include hysteresis zones 150A, 150B, 150C, and 150D (collectively "hysteresis zones 150"). Hysteresis zones 150 are positions within posture state area 140 where no posture cones have been defined and as such are not associated with a defined posture state. Hysteresis zones 150 may be particularly useful when IMD 14 utilizes the posture state information and posture cones to adjust therapy automatically. If the posture state sensor indicates that patient 12 is in upright cone 142, IMD 14 would not detect that patient 12 has entered a new posture state until the posture state parameter value indicates a vector that lies within a different posture cone. For example, if IMD 14 determines that patient 12 moves to within hysteresis zone 150A from upright cone 142, IMD 14 may retain the patient's posture as upright. In this manner, IMD 14 does not change the corresponding therapy until patient 12 fully enters a different posture cone. Hysteresis zones 150 prevent IMD 14 from continually oscillating between different therapies when the patient's posture state resides near a posture cone boundary.

In another embodiment, hysteresis zones 150 could be associated with a "benign" parameter set. For instance, the zones could be associated with a low-amplitude stimulation that is known to be unlikely to cause any patient discomfort regardless of posture state. When the patient's posture state is indicated as falling within one of the hysteresis zones, therapy could be adjusted in accordance with the benign parameter set. Any other control parameters that control some other aspect of the system could likewise be set to a "benign" state when the patient enters a hysteresis zone, if desired.

Each posture cone 142, 144, 146, 148 may be defined by an angle in relation to a reference coordinate vector defined for the respective posture cone. Alternatively, some posture cones may be defined by an angle relative to a reference coordinate vector for another posture cone. For example, lying postures may be defined by an angle with respect to a reference coordinate vector for an upright posture cone. In each case, as described in further detail below, each posture cone may be defined by an angle in relation to a reference coordinate posture vector defined for a particular posture state.

A reference coordinate vector may be defined based on posture sensor data generated by a posture state sensor while patient 12 occupies a particular posture state desired to be defined using the reference coordinate vector. For example, a patient may be asked to occupy a posture such as standing so that a reference coordinate vector can be sensed for the respective (e.g., standing) posture. In this manner, the patient's standing posture need not align perfectly with vertical axis 141 but rather the posture state definition can be defined according to the patient's actual orientation. Then, a posture cone can be defined using the measured reference coordinate vector as the center of the cone that defines that posture state.

Vertical axis 141 in FIG. 8A may correspond to a reference coordinate vector sensed while the patient was occupying an upright posture state. Similarly, a horizontal axis 143 may correspond to a reference coordinate vector sensed while the patient is occupying a lying posture state. A posture cone may be defined with respect to the reference coordinate vector. Although a single axis is shown extending through the upright and inverted cones 142, 146, and another single axis is shown extending through the lying down and lying up cones 144, 148, individual reference coordinate vectors may be used for respective cones, and the reference coordinate vectors may not share the same axes, depending on differences between the reference coordinate vectors obtained for the posture cones.

Posture cones may be defined by the same angle or different angles, symmetrical to either axis, or asymmetrical to either axis. For example, upright cone 142 may have an angle of eighty degrees, +40 degrees to −40 degrees from the positive vertical axis 141. In some cases, lying cones may be defined relative to the reference coordinate vector of the upright cone 142. For example, a lying cone 148 may have an angle of eighty degrees, −50 degrees to −130 degrees, from the positive vertical axis 141. Inverted cone 146 may have an angle of eighty degrees, −140 degrees to +140 degrees from vertical axis 141. In addition, lying down cone 144 may have an angle of eighty degrees, +50 degrees to +130 degrees from the positive vertical axis 141. In other examples, each posture cone may have varying angle definitions, and the angles may change during therapy delivery to achieve the most effective therapy for patient 12.

As discussed above, instead of an angle, posture cones 144, 146, 148, 148 may be defined by a cosine value or range of cosine values in relation to vertical axis 141, horizontal axis 143, or some other axis, such as, e.g., individual reference coordinate vectors for the respective cones. For example, a posture cone may be defined by a cosine value that defines the minimum cosine value, calculated using a reference coordinate vector and a respective coordinate vector sensed by a posture state sensor at any point in time. In the cosine computation, the value (adjacent/hypotenuse) can be computed using the magnitude of the coordinate reference vector as the adjacent and a vector at the outermost extent of the cone as the hypotenuse to define a range of cosine values consistent with the outer bound of the cone.

For upright cone 142, the cosine range may extend from the maximum cosine value of 1.0, corresponding to a sensed vector that matches the reference coordinate vector of the upright cone, to a minimum cosine value that corresponds to a sensed vector at the outer limit of the upright cone. As another example, for lying cone 144, the cosine range may extend from the maximum cosine value of 1.0, corresponding to a sensed vector that matches the reference coordinate vector of the lying cone, to a minimum cosine value that corresponds to a sensed vector at the outer limit of the lying cone. Alternatively, the lying cone 144 may be defined with reference to the upright cone 142, such that the cosine range may extend between a maximum and minimum values determined relative to the reference coordinate vector for the upright cone.

The use of cosines, sines, or another distance measurement to determine whether a sensed coordinate vector lies within a posture space allows the patient's posture state to be determined without the need to derive angles, such as the angle between a sensed coordinate vector and a reference vector. Such derivation of angles is computationally-expensive, and therefore requires a relatively large amount of processing power. Eliminating such angle derivations can save energy, lengthening the time between recharge for IMDs having rechargeable power sources, and prolonging time between explant for IMDs having primary cell power sources.

In other examples, posture state area 140 may include additional posture cones than those shown in FIG. 8A. For example, a reclining cone may be located between upright cone 142 and lying back cone 148 to indicate when patient 12 is reclining back (e.g., in a dorsal direction). In this position, patient 12 may need a different therapy to effectively treat symptoms. Different therapy programs may provide efficacious therapy to patient 12 when patient 12 is in each of an upright posture (e.g., within upright cone 142), lying back posture (e.g., within lying back cone 148), and a reclining back posture. Thus, a posture cone that defines the reclining back posture may be useful for providing efficacious posture-responsive therapy to patient 12. In other examples, posture state area 140 may include fewer posture cones than cones 142, 144, 146, 148 shown in FIG. 8A. For example, inverted cone 146 may be replaced by a larger lying back cone 148 and lying front cone 144.

FIG. 8B illustrates an example posture state space 152 that is a three-dimensional space in which the posture state parameter value from the posture state sensor is placed in relation to the posture cones. Posture state space 152 is substantially similar to posture state area 140 of FIG. 8A. However, the posture state parameter value derived from all three axes of a three-axis accelerometer may be used to accurately determine the posture state of patient 12. In the example of FIG. 8B, posture state space 152 includes upright cone 154, lying back cone 156, and lying front cone 158. Posture state space 152 also includes hysteresis zones (not shown) similar to those of posture state area 140. In the example of FIG. 8B, the hysteresis zones are the spaces not occupied by a posture cone, e.g., upright cone 154, lying back cone 156, and lying front cone 158.

Posture cones 154, 156 and 158 also are defined by a respective center line 153A, 153B, or 153C, and associated cone angle A, B or C. For example, upright cone 154 is defined by center line 153A that runs through the center of upright cone 154. Center line 153A may correspond to an axis of the posture state sensor or some other calibrated vector. In some embodiments, each center line 153A, 153B, 153C may correspond to posture reference coordinate vectors defined for the respective postures, e.g., the upright posture. For instance, assuming that patient 12 is standing, the DC portion of the x, y, and z signals detected by the posture state sensor of posture state module 86 define a posture vector that corresponds to center line 153A. The x, y, and z signals may be measured while patient 12 is known to be in a specified position, e.g., standing, and the measured vector may be correlated with the upright posture state. Thereafter, when the DC portions of the posture state sensor signal are within some predetermined cone tolerance or proximity, e.g., as defined by an angle, distance or cosine value, of the posture reference coordinate vector (i.e., center line 153A), it may be determined that patient 12 is in the upright posture. In this manner, a sensed coordinate vector may be initially measured based on the output of one or more posture state sensors of posture state module 86, associated with a posture state, such as upright, as a reference coordinate vector, and then later used to detect a patient's posture state.

As previously indicated, a posture state is defined by a region in space which, in one embodiment, identified by a reference coordinate vector and some relationship to that reference vector, where that relationship may be described as a "tolerance". The tolerance may be virtually any type of relationship such as an angle, a trigonometric function (e.g., cosine or sine), some other equation or some other relationship. While the foregoing primarily describes these regions in space as being cones surrounding the corresponding reference vectors, it will be understood that the region in space can take on any shape and need not necessarily be a region in space that includes the reference vector used to define that region. For instance, the region could be a toroid ("donut") that encircles the reference vector, or a region in space extending away from the reference vector. Thus, a posture state can be associated with virtually any region in space that can be described by the tolerance.

Returning to the previous examples of posture cones, one way to specify a tolerance is by providing an angle, such as cone angle A, relative to coordinate reference vector 153A, which results in posture cone 154 as described herein. Cone angle A is the deflection angle, or radius, of upright cone 154. The total angle that each posture cone spans is double the cone angle. The cone angles A, B, and C may be generally between approximately 1 degree and approximately 70 degrees. In other examples, cone angles A, B, and C may be between approximately 10 degrees and 30 degrees. In the example of FIG. 8B, cone angles A, B, and C are approximately 20 degrees. Cone angles A, B, and C may be different, and center lines 153A, 153B, and 153C may not be orthogonal to each other.

In some examples, a tolerance may be specified by a cosine value or range of cosine values. The use of cosine values, in some cases, may provide substantial processing efficiencies. For example, the cosine values associated with the upright posture state represented by posture cone 154 in FIG. 8B will range between 1 and the cosine of angle A.

If a sensed coordinate vector, in conjunction with the reference coordinate vector for a posture cone, produces a cosine value that is less than the minimum cosine value for the posture cone, the sensed coordinate vector does not reside within the pertinent posture cone. In this manner, the minimum cosine value may define the outer bound of a range of cosine values within a particular posture cone defined in part by a reference coordinate vector.

While center lines 153A, 153B, 153C of each of the posture cones 154, 156, 158, respectively, are shown in FIG. 8B as being substantially orthogonal to each other, in other examples, center lines 153A, 153B, and 153C may not be orthogonal to each other. Again, the relative orientation of center lines 153A, 153B, 153C may depend on the actual reference coordinate vector output of the posture state sensor of posture state module 86 of IMD 14 when patient 12 occupies the respective postures.

In some cases, all of the posture cones may be individually defined based on actual reference coordinate vectors. Alternatively, in some cases, some posture cones may be defined with reference to one or more reference coordinate vectors for one or more other posture cones. For example, lying reference coordinate vectors could be assumed to be orthogonal to an upright reference coordinate vector. Alternatively, lying reference coordinate vectors could be individually determined (e.g., measured) by having a patient assume a respective lying posture state and then measuring the sensed coordinate vectors while the patient is in that posture state. Hence, the actual reference coordinate vectors for different postures may be orthogonal or non-orthogonal with respect to one another.

In addition to upright cone 154, lying back cone 156, and lying front cone 158, posture state space 152 may include additional posture cones. For example, a lying right cone may be provided to define a patient posture in which patient 12 is lying on his right side and a lying left cone may be provided to define a patient posture in which patient 12 is lying on his left side. In some cases, the lying right cone and lying left cone may be positioned approximately orthogonal to upright cones 154, in approximately the same plane as lying back cone 156 and lying front cone 158. Moreover, posture state space 152 may include an inverted cone positioned approximately opposite of upright cone 154. Such a cone indicates that the patient's posture is inverted from the upright posture, i.e., upside down.

In some examples, to detect the posture state of a patient, posture state module 86 of IMD 14 may determine a sensed coordinate vector based on the posture sensor data generated by one or more posture state sensors, and then analyze the sensed coordinate vector with respect to posture cones 154, 156, 158 of FIG. 8B. For example, in a case in which a posture cone is defined by a reference coordinate vector 153A and the angle A, posture state module 86 may determine whether the sensed coordinate vector is within upright posture cone 154 by calculating the angle between the sensed coordinate vector and reference coordinate vector, and then determining whether the angle is less than the angle A. If so, posture state module 86 determines that the sensed coordinate vector is within upright posture cone 154 and detects that patient 12 is in the upright posture. If posture state module 86 determines that sensed coordinate vector is not within upright posture cone 154, posture state module 86 detects that patient 12 is not in the upright posture.

In another example, posture state module 86 may instead measure a sensed coordinate vector associated with the patient's current posture state and calculate a cosine of the angle between this sensed vector and the reference coordinate vector. Posture state module may then determine whether that cosine value lies within the range of cosine values associated with that posture state. If so, the patient may be classified as being in this posture state. Posture state module 86 may, in this manner, compare a sensed coordinate vector representing the patient's current posture state with respect to each individual defined posture regions, such as posture cones 156 and 158 to determine in which region, if any, the sensed vector resides. Hence, a region-by-region (e.g., cone-by-cone) analysis is one option for posture detection.

Various alternative mechanisms for determining a posture state of a patient by comparing a reference coordinate vector associated with a defined posture state to a sensed coordinate vector associated with a patient's current posture state are described in commonly-assigned U.S. patent application Ser. No. 12/433,004 filed Apr. 30, 2009 entitled "Posture State Classification for a Medical Device", which is hereby incorporated herein by reference to the full extent that the application does not conflict with the current disclosure.

The above description contemplates comparing a sensed coordinate vector against posture regions (e.g., cones) on a region-by-region basis. A different phased approach may be applied where the sensed coordinate vector is first classified as either upright or not upright prior to performing an analysis in reference to other posture state. In particular, posture state module 86 may first analyze the sensed coordinate vector in posture state space 152 with respect to an axis 153A for the upright posture state. As was the case described above, it may be assumed for discussion that axis 153A corresponds to the upright reference coordinate vector measured when the patient assumes an upright posture state. Angle "A" may be used to define upright posture cone 154 for the upright posture state. Alternatively, a trigonometric or other function may be used to define this posture state region in three-dimensional space.

If it is determined that a sensed coordinate vector is not within the upright posture state region shown as cone 154, it may next be determined whether a sensed coordinated vector is generally in the lying posture space volume, which may be considered somewhat donut- or toroid-like, and may be defined relative to the upright reference coordinate vector 153A. As shown, angles "D" and "E" define the minimum and maximum angle values, respectively, that a sensed vector may form with respect to axis 153A of patient 12 for a determination to be made that the patient is generally in the lying posture state. Again, cosine, sine, or some other distance or other function may be used instead of angles to determine the positions of sensed coordinate vectors relative to the defined posture regions in space.

If a sensed vector is determined to be within the angular range of D to E relative to axis 153A (or to instead satisfy some other relationship defining the lying posture state space, such as a range of cosine values), then it can be determined by posture state module 86 that the patient is generally in a lying posture. This region generally defining the lying posture state may be referred to as a posture donut or posture toroid, rather than a posture cone. The posture donut may generally encompass a range of vectors that are considered to be representative of various lying down postures. In some cases, if lying postures are defined by cones, the lying volume could be defined as a logical OR of the donut- or toroid-like volume and the volumes of the lying posture cones. If the cones are larger such that some portions extend beyond the lying volume, then those portions can be added to the lying volume using the logical OR-like operation.

If the posture state module 86 determines that the sensed coordinate vector resides within the donut- or toroid-like lying volume, then the sensed coordinate vector may be tested against each of a plurality of lying posture cones in the lying volume to determine in which, if any, of the lying posture cones the sensed coordinate vector resides. Based on this region-by-region comparison, posture state module 86 may then classify the patient as being in the posture state associated with the cone in which the sensed coordinate vector lies.

As another approach, after it is determined that the sensed coordinate vector resides within the lying posture state region, a proximity test may be used to compare the sensed coordinate vector to each of the reference coordinate vectors for the respective lying postures. The proximity test may rely on angle, cosine value or distance to determine which of the lying posture reference coordinate vectors is closest to the sensed coordinate vector. For example, the reference coordinate vector that produces the largest cosine value with the sensed coordinate vector as hypotenuse and the reference coordinate vector as adjacent is the closest reference coordinate vector. The lying posture state associated with the reference coordinate vector producing the largest cosine value is the detected posture state. Hence, there are a variety of ways to detect posture, such as using posture regions (e.g., cones, toroids, or other regions), using an upright posture cone with a lying volume and lying posture cone test, or using an upright posture cone with lying volume and lying vector proximity test.

The foregoing discussion described the lying posture volume as being defined relative to axis 153A. However, in a different example, an angle C could be defined according to a generally horizontal axis 153C (which may correspond to one of the lying reference coordinate vectors). In this case, if a sensed vector is within angle C of axis 153C, it can be determined by posture state module 86 that the patient is in a lying posture. After the patient is determined to be in a lying posture state, one of the various approaches discussed above (e.g., region-by-region comparison, proximity test, etc.) could be used to identify in which of the lying posture states the patient resides.

In any of the foregoing approaches, it will be understood that posture state module 86 may rely on trigonometric functions (a range or sine or cosine values) or some other function such as a distance relationship that defines the posture state region, and which is used to determine whether a sensed coordinate vector resides within a particular posture state region. As yet another example of this, a first range of cosine values may be used to define the upright posture space (e.g., cone 154) and a second range of cosine values may be used to define a posture donut or toroid having axis 153A as its central axis. If the sensed vector and reference coordinate vector 153 produce a cosine value in a first range, the posture state of the patient is determined to be upright. If the cosine value is in a second range, the posture state is determined to be lying. If the cosine value is outside of the first and second ranges, the posture may be indeterminate. The first range may correspond to the range of cosine values that would be produced by vectors in posture cone 154 defined by angle A, and the second range may be correspond to cosine values that would be produced by vectors in the posture donut defined by angles D and E.

FIG. 8C illustrates use of the aforementioned proximity test to determine a patient's lying posture state. It will be recalled that such a proximity test may be used instead of a region-by-region comparison.

In this example, posture state space 155 is a three-dimensional space substantially similar to posture state space 152 of FIG. 8B. Posture state space 155 includes upright posture cone 157 defined by reference coordinate vector 167 and some tolerance that defines which region in space relative to the reference coordinate vector 167 is to be included in the upright posture space. The tolerance that defines upright posture cone 157 with respect to reference coordinate vector 167 may be described by an angle, a trigonometric range of values, or some other relationship describing a posture state region in space as discussed above.

As shown in FIG. 8C, posture state space 155 also includes four reference coordinate vectors 159, 161, 163, 165, which are associated with lying left, lying right, lying front, and lying back posture states, respectively. Posture state module 86 may have defined each of the four reference coordinated vector 159, 161, 163, 165 based on the output of one or more posture sensors while patient 12 occupied each of the corresponding posture states. For instance, this may have occurred at a time when these reference coordinate vectors were first being initialized, or at a time when these vectors were being re-initialized.

Unlike lying front and lying back posture cones 158, 156 in the example of FIG. 8B, the posture state reference data for the four defined posture states corresponding to reference vectors 159, 161, 163, 165 need not include a tolerance value that defines an actual region in space (e.g., a cone) Rather, as will be described below, a proximity test will be used to determine which of these vectors lies closest to a sensed coordinate vector describing the patient's current posture state.

In some examples, to determine the posture state of patient 12, posture state module 85 may determine whether a sensed coordinate vector is within upright posture cone 157 by analyzing the sensed coordinate vector in view of the tolerance describing the upright posture state (e.g., angle, range of cosine value(s), etc.) If the patient is not determined to be in the upright posture state, a similar is analysis is performed to determine whether the sensed vector is within a posture donut or toroid associated with the lying posture state, as may be defined by a range of angles (as in FIG. 8B), cosine values, or some other function.

If posture state module 86 determines that patient 12 is occupying the lying posture state, posture state module 86 may then calculate the cosine value of the sensed coordinate vector with respect to each lying reference coordinate vectors 159, 161, 163, 165. In such a case, posture state module 86 determines the particular lying posture state of patient 12, i.e., lying left, lying right, lying front, lying back, based on which cosine value is the greatest of the four cosine values. For example, if the cosine value calculated with the sensed vector as the hypotenuse and the lying front reference vector 163 as the adjacent vector is the largest value of the four cosine values, the sensed vector may be considered closest in proximity to lying front reference vector out of the four total reference vectors 159, 161, 163, 165. Accordingly, posture state module 85 may determine that patient 12 is occupying a lying front posture state.

Some of the examples above describe the lying posture region in space as a donut or toroid that surrounds, and is defined relative to, an upright reference vector, such as axis 153A of FIG. 8B or upright reference vector 167 of FIG. 8C. For example, such a donut may be defined using angles D and E as in FIG. 8B. Such a technique may be appropriate when lying posture reference vectors 159, 161, 163, 165 define a common plane substantially orthogonal to upright posture reference vector 167. However, the lying posture reference vectors 159, 161, 163, 165 may not, in fact, be orthogonal to the upright reference coordinate vector 167. Also, the lying posture reference vectors 159, 161, 163, 165 may not reside in the same plane.

To account for non-orthogonal lying reference vectors, in other examples, a lying posture donut or toroid may be defined with respect to a modified or virtual upright reference vector 169 rather than the actual upright posture reference vector 167. Again, such a technique may be used in situations in which the lying reference vectors 159, 161, 163, 165 are not in a common plane, or the common plane of reference vector 159, 161, 163, 165 is not substantially orthogonal to upright reference vector 167. However, use of the example technique is not limited to such situations.

To define virtual upright reference vector 169, posture state module 86 may compute the cross-products of various combinations of lying reference vectors 159, 161, 163, 165 and average the cross product values. In the example of FIG. 8C, posture state module 86 may compute four cross products and average the four cross product vectors to yield the virtual upright vector. The cross product operations that may be performed are: lying left vector 159×lying back vector 165, lying back vector 165×lying right vector 161, lying right vector 161×lying front vector 163, and lying front vector 163×lying left vector 159. Each cross product yields a vector that is orthogonal to the two lying reference vectors that were crossed. Averaging each of the cross product vectors yields a virtual upright reference vector that is orthogonal to lying plane 171 approximately formed by lying reference vectors 159, 161, 163, 165.

Using virtual upright reference vector 169, posture state module 86 may define a lying posture donut or toroid in a manner similar to that described with respect to upright reference vector 167, but instead with respect to virtual upright reference vector 169. In particular, after posture state module 86 determines that the patient is not in the upright posture associated with upright posture cone 157 surrounding reference coordinate vector 167, the posture state module may next determine whether the patient is in a lying posture state. This is determination is based on an angle, a range of sine or cosine values, or some other tolerance that is defined with respect to the virtual upright reference vector 169 rather than the reference coordinate vector 167 for the actual upright posture state.

If posture state module 86 determines that patient 12 is occupying a general lying posture state based on the analysis of the sensed coordinate vector with respect to virtual upright reference vector 169, posture state module 86 may then calculate the cosine value of the sensed coordinate vector (as hypotenuse) with respect to each lying reference coordinate vectors 159, 161, 163, 165 (as adjacent).

In such a case, posture state module 86 determines the particular lying posture state of patient 12, i.e., lying left, lying right, lying front, lying back, based on which cosine value is the greatest of the four cosine values. For example, if the cosine value calculated with the lying front reference vector 163 is the largest value of the four cosine values, the sensed vector may be considered closest in proximity to lying front reference vector as compared to all four reference vectors 159, 161, 163, 165. Accordingly, posture state module 86 may determine that patient 12 is occupying a lying front posture state.

While the foregoing describes posture state definitions as being related to either cones surrounding a vector or donuts surrounding a vector, this is an example only, and should not be considered limiting. For example, a definition of a posture state may involve a posture vector and a tolerance that describes a maximum distance from the posture vector. So long as a sensed coordinate vector is more than this maximum distance from the posture vector that is included in the definition of the posture state, patient 12 may be classified as being in that posture state. In this case, a region in space may be defined that does not include the reference vector that is used to define this region in space.

As yet another example, multiple vectors and multiple tolerances may be referenced to create a single posture definition. For instance, two reference coordinate vectors, each being associated with respective tolerances, may describe two cones in three dimensional space. These cones may both be used to define a posture region that corresponds to a posture state. That is, a posture definition may specify that the area within either one, or both, of the cones is included in the definition. This corresponds to an OR-type logic function (e.g., such as a Boolean Logic function). As another example, the definition may specify that only an area that resides in both of two overlapping cones in included in the definition. This corresponds to an AND-type logic function. Another illustration involves specifying that only the area in one, but not the other, of two overlapping cones is included in the definition. This type of operation utilizes both AND- and NOT-type logical functions.

According to another embodiment, a posture state definition may reference one or more toroids and/or one or more cones. These regions may, or may not, overlap. A posture state definition may be created that references multiple ones of these regions, and that may further utilize logic functions (e.g., OR, AND, NOT, etc.) to indicate which portions of these regions are to be associated with a particular posture definition. Thus, it will be understood multiple regions in space may be referenced by a single posture definition. When multiple regions are involved, any logic function (e.g., of a Boolean type, etc.) known in the art may be used to define relationships indicating which portions of which regions are included in the posture definitions. Techniques for creating posture definitions using multiple regions in three-dimensional space are described in commonly-assigned patent application entitled "Posture State Classification for a Medical Device" having Ser. No. 12/432,993 filed Apr. 30, 2009 and which is hereby incorporated herein by reference to the full extent that the application does not conflict with the current disclosure.

Each region in three-dimensional space that is associated with a respective posture state definition may be associated with respective therapy parameters. When posture state logic 86 determines that a patient is in a particular posture state using any of the example techniques described herein, a therapy delivery module such as stimulation generator 84 may deliver therapy in accordance with the therapy parameters associated with that determined posture state. In this manner, therapy is automatically tailored to a patient's posture and/or activity level.

In some examples, individual posture states may be linked together, thereby tying posture states to a common set of posture reference data and a common set of therapy parameter values. This may, in effect, merge multiple posture cones for purposes of posture state-based selection of therapy parameter values. For example, all lying posture state cones (back, front, left, right) could be treated as one cone or a donut/toroid, e.g., using a technique the same as or similar to that described with respect to FIGS. 8B and 8C to define a donut, toroid or other volume. One program group or common set of therapy parameter values may apply to all posture states in the same merged cone, according to the linking status of the posture states, as directed via external programmer 20.

Merging posture cones or otherwise linking a plurality of posture states together may be useful for examples in which a common set of therapy parameter values provides efficacious therapy to patient 12 for the plurality of posture states. In such an example, linking a plurality of posture states together may help decrease the power consumption required to provide posture-responsive therapy to patient 12 because the computation required to track patient posture states and provide responsive therapy adjustments may be minimized when a plurality of posture states are linked together.

Linking of posture states also may permit a therapy parameter value adjustment in one posture state to be associated with multiple posture states at the same time. For example, the same amplitude level for one or more programs may be applied to all of the posture states in a linked set of posture states. Alternatively, the lying down posture states may all reside within a "donut" or toroid that would be used instead of separate comes 156 and 158, for example. The toroid may be divided into sectional segments that each correspond to different posture states, such as lying (back), lying (front), lying (right), lying (left) instead of individual cones. In this case, different posture reference data and therapy parameter values may be assigned to the different sectional segments of the toroid.

According to some embodiments of the disclosed posture detection mechanism, posture states may be defined in the coordinate system of the sensors 86A rather than in the patient's body coordinate system. Because the coordinate system of the sensors 86A is used to define posture states, there is no need to derive a correction for, or apply a correction factor to, the output of sensors 86A before posture state detection can occur. This is in contrast to some posture state detection mechanisms that position a sensor with respect to a patient's body, and then determine an offset between the sensor axes and respective axes of the patient's body. As an example, an offset may be determined between a first axis of the sensor and the Superior-Inferior (S-I) axis of the patient's body. Another offset may be determined between a second axis of the sensor and the Anterior-Posterior (A-P) axis of the patient's body. Still another offset may be derived to describe an offset between a third axis of the sensor and the Lateral-Medial (L-M) axis of the body. When a sensor reading is obtained, these offsets may be used to correct the sensor reading, and the corrected sensor reading is then used to determine a patient's posture. Such mechanisms may involve determining the offsets, and then using those offsets to perform a transformation or correction on the output from sensors 86A. The resulting corrected sensor reading may then be used to determine the patient's posture state. This type of posture state detection is processor-intensive, utilizes power, and is time-consuming and therefore may not be ideal for implantable device scenarios.

According to examples disclosed herein, no correction need be applied to the posture state parameters sensed by sensors 86A prior to their use in performing posture state detection. Rather, the sensor readings are used directly without any transformation or correction process, streamlining posture state detection. This dramatically simplifies the process of performing posture detection, and thereby saves a significant amount of power and processing time. This is particularly important for devices such as IMDs that have a limited power supply (e.g., rechargeable or non-rechargeable batteries).

To provide the ability to utilize the output of sensors 86A directly without the need to perform transformations or correction, the posture state definitions must be defined in the coordinate system of sensors 86A rather than in the coordinate system of the patient 12. To accomplish this, sensors 86A are positioned on, or in, patient 12 in any orientation in a substantially fixed manner. For instance, the sensors 86A may have been implanted in the patient during a surgical procedure, may have been located on the patient using a transcutaneous procedure, may be temporarily or permanently affixed to an external surface of the patient, or may be carried on the patient's clothing or other articles donned by the patient. The orientation of the sensors relative to the patient is substantially unchanging, at least over some period of time during which posture state detection will occur.

Once sensors 86A are disposed in relation to the patient's body, the patient is asked to temporarily assume a posture state. Outputs from sensors 86A are obtained while the patient is in the assumed posture state. In the case of a three-axis accelerometer, these outputs define a reference coordinate vector in three-dimensional space of the type described above in regards to FIGS. 8A-8C. The reference coordinate vector may, in one embodiment, be expressed in terms of the coordinate system of sensors 86A without regard to the coordinate system of the patient's body. This vector that is defined by the output of sensors 86A may be any vector in three-dimensional space.

Next, the reference coordinate vector may be associated with the posture state that the patient has been asked to assume. This association may occur by storing the reference coordinate vector or some representation thereof with a designation that identifies the posture state. Such an association may be stored within a table or some other aggregation of data such as may be stored within memory 82 of IMD 14, memory 94 of IMD 26, memory 108 of programmer 20 and/or some memory available in the system 120.

The patient may be asked to assume any number of postures in the foregoing manner. As each posture is assumed, signals are obtained from sensors 86A that are indicative of a reference coordinate vector that are, in one embodiment, expressed in the coordinate system of sensors 86A without regard to the coordinate system of the patient. The reference coordinate vector or a representation thereof is associated with the posture state under definition.

After a reference coordinate vector is associated with a posture state, a tolerance may be selected. As discussed above, this tolerance defines a relationship to the reference coordinate vector. This relationship may describe a cone, a toroid, or some other region that surrounds or is otherwise disposed in relation to the reference coordinate vector, as was disclosed above in reference to FIGS. 8A-8C. Like the reference coordinate vector, this selected tolerance is associated with the posture. Together, the reference coordinate vector and the tolerance can be used to define a posture state definition. This definition, as well as other defined posture state definitions, may then be compared to a sensed coordinate vector representing the patient's current posture state so that the patient's current posture state can be determined.

It may be appreciated that using the aforementioned technique, posture states may be defined that are specific to a particular patient's activities and/or profession. For instance, a bank teller may spend a significant portion of his working day leaning forward at a particular angle. A patient-specific posture state definition associated with this leaning posture may be defined by having the patient assume this position and recording the reference coordinate vector. A cone angle or other tolerance value selected for this posture state may be selected that is specific to the particular posture state definition for this patient. In this manner, the defined posture states may be tailored to a specific user, and need not be "hard-coded" in the IMD.

A patient may use a programming device such as external programmer 20 to record reference coordinate vectors in the manner described above. For instance, a user may issue a command via external programmer 20 to IMD 14 when a patient has assumed a desired position. This command causes IMD 14 to obtain signal values from sensors 86A, which are optionally processed by posture state module 86 of IMD (e.g., filtered to extract a DC component of the signals) and stored in memory 82, as one example. These sensor signals may also be uplinked via telemetry circuitry 88 to an external device such as external programmer 20 to undergo some of the processing steps. The captured sensor signals may be associated with an indication (e.g., an alpha-numeric tag, a binary tag, etc.) identifying a posture state as specified by a user employing external programmer 20. Such an indication may be provided using display 36, keypad 40, a touch screen, a peripheral pointing device 68 (as shown in FIG. 3), and/or other types of user interface mechanisms, as described above. A user interface such as a graphical user interface may be employed during this process. A tolerance may likewise be specified by the user for association with this posture definition. The associations may be stored in memory of external programmer 20, in memory 82 of IMD 14, or in some other storage facility. Additional techniques for defining a posture vector and creating the above-described associations are described in commonly-assigned patent application Ser. No. 12/432,993 filed Apr. 30, 2009 and referenced above As discussed above, examples of this disclosure utilize posture state definitions defined in the coordinate system of sensors (e.g., sensors 86A, 98A). This provides various processing efficiencies, such as eliminating the need to derive and apply correction values to be applied to the raw sensor outputs. However, aspects of the current disclosure may alternatively be practiced with other types of posture state detection mechanisms that do utilize correction techniques such as applying transformations or correction values to raw sensor outputs. Thus, using posture state definitions that are defined in the coordinate system of the sensor is one optional aspect of the disclosure, and should not be considered limiting.

The foregoing primarily focuses on determining a posture component of a posture state. For instance, FIGS. 8A-8C described using reference coordinate vectors for various postures such as "Upright", "Lying Back", "Lying Forward", and so onto determine the patient's posture state. Recall, however, that a posture state may likewise be associated with an activity state. Whereas the posture may be derived from a DC component of the output of sensors 86A describing the gravitational force exerted upon the sensor (and on the patient generally), the activity state may be determined from an AC component of the sensor signal which relates to patient activity.

As a specific example, a posture state of "Upright and Active" may be associated with an upright posture (e.g., a posture located within cone 154 of FIG. 8B) and an activity state that is associated with an activity level above some predetermined threshold level, for instance (e.g., more than 15 activity counts per second based on the AC component of an accelerometer signal.)

An activity state may be defined using patient participation in a manner similar to that described above in reference to posture definition. A patient carrying a sensor may be directed to begin performing an activity (which may involve motion or lack thereof). One or more raw or processed signals may be obtained from the sensor. These one or more signals are indicative of the patient's activity. In one embodiment, these signals may be obtained from AC components of the sensor signals. These one or more signals may be stored along with the definition of the activity state. In some instances, a user such as clinician may provide additional information to include with the activity state definition. As an example, if the signals provide a vector indicative of velocity or acceleration, the user may supply a tolerance to be used with these signals in much the same way a tolerance is selected for use with a posture vector.

In an alternative embodiment, patient participation need not be employed in the definition of the activity state. In this case, the user (e.g., a clinician) may supply all information that is required for the activity state definition. For instance, a clinician may provide both a vector and a tolerance for use in defining the activity.

After definition of the activity state, the definition may be used to classify movement of a patient. In this case, one or more signals are received from the sensor while the patient is going about a daily routine. These signals may be processed (e.g., filtered to extract AC signal components, etc.) and compared against the defined activity states to determine whether the patient is to be classified as being in this activity state.

As previously noted, one or more of the activity state definitions may include respective vectors. To determine whether a patient is in this type of an activity state, a sensed coordinate vector (e.g., velocity or acceleration vector) may be obtained from the AC component of the sensor signals and compared to one or more of the reference activity vectors. This comparison may utilize any of the techniques described herein in regards to posture classification. That is, this comparison may be performed by determining whether the sensed coordinate vector has a distance relationship to a reference activity vector as determined by an associated tolerance. Any of the mechanisms described above regarding comparing sensed coordinate vectors to reference vectors to determine posture may be applied to comparing sensed activity vectors to reference vectors to determine activity state. An activity state definition may likewise employ virtual vectors of logical functions, as was described above with respect to posture definitions.

In the foregoing manner, a posture state definition may comprise information identifying just a posture, information identifying just an activity state, or both. Such definitions may be created using patient participation. In an alternative embodiment, a clinician may merely specify the data needed for the definition (e.g., by specifying a vector and a tolerance for a posture definition, an activity count for an activity state definition, etc.)

Figure 9:
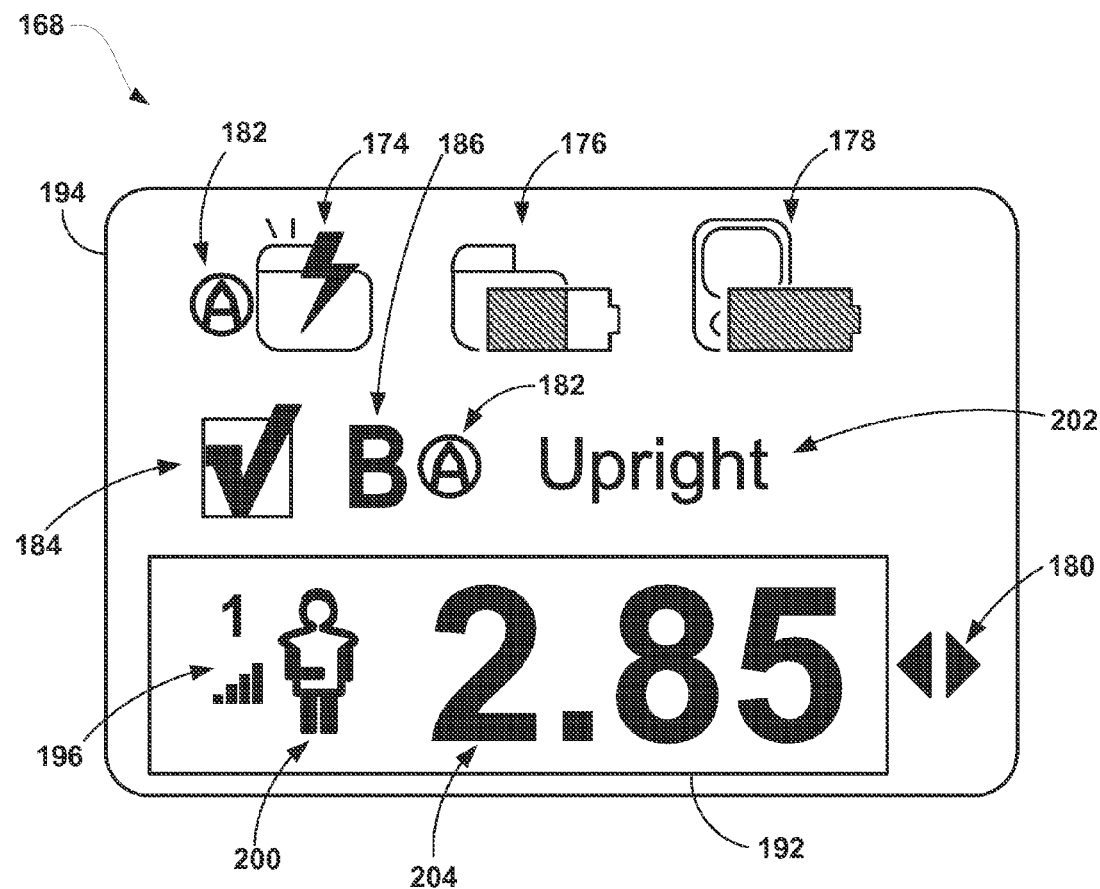
FIG. 9 is a conceptual diagram illustrating an example user interface of a patient programmer for delivering therapy information that includes posture information to the patient.

FIG. 9 is a conceptual diagram illustrating an example user interface 168 of a patient programmer 30 for delivering therapy information that includes posture information to the patient. In other examples, user interface 168 may also be shown on clinician programmer 60. In the example of FIG. 9, display 36 of patient programmer 30 provides user interface 168 to the user, such as patient 12, via screen 194. Screen 194 includes stimulation icon 174 associated with stimulation therapy, IMD battery icon 176, programmer battery icon 178, and automatic posture response icon 182.

In addition, screen 194 includes group selection icon 184 and group identifier 186. Group identifier 186 indicates one of possibly several groups of programs that can be selected for delivery to patient 12. Group selection icon 184 indicates whether the displayed group, e.g., group B in FIG. 9, is actually selected for delivery to patient 12. If a presently displayed group is selected, group selection icon 184 includes a box with a checkmark. If a presently displayed group is not selected, group selection icon 184 includes a box without a checkmark. To navigate through the stored program groups, a user may use control pad 40 to move selection box 192 to select the group identifier 186 and then use control pad 40 (FIG. 2) to scroll through the various groups, e.g., A, B, C, and so forth. IMD 14 may be programmed to support a small number of groups or a large number of groups, where each group contains a small number of programs or a large number of programs that are delivered simultaneously, in sequence, or on a time-interleaved basis.

User interface 168 further includes a program identifier 196. This indicates that information regarding program "1" of program group "B" is displayed on screen 194. Amplitude value 204 indicates that the current voltage amplitude of program "1" is 2.85 Volts. Patient 12 may scroll through different programs of the group by using navigation arrows 180 via arrows 44 and 48 of control pad 40 (FIG. 2).

In the example of FIG. 9, Group identifier 186 is associated with automatic posture response icon 182. The presence of this icon indicates that IMD 14 is automatically adjusting therapy according to patient posture state detection according to program group "B". That is, IMD 14 is utilizing associations between therapy adjustments and posture states as referenced by program group B to deliver therapy to a patient according to the patient's detected posture states.

User interface 168 also indicates the posture state determined by IMD 14 for the patient at a given instant in time via posture state indication 200, which illustrates an "Upright" person via indication 200, and supplementary posture state indication 202, which describes the posture state determination using a character string. Posture state indication 200 and supplementary posture state indication 202 presented via user interface 168 change according to the sensed, or detected, posture state detected by IMD 14. The posture state may be communicated to the external programmer immediately after IMD 14 detects a posture change, or communicated periodically or non-periodically by IMD 14 unilaterally or upon receiving a request from the programmer. Accordingly, the posture state indication 200 and/or supplementary posture state indication 202 may represent a current, up-to-the minute status, or a status as of the most recent communication of posture state from IMD 14. Posture state indication 200 is shown as a graphical representation, but the posture state indication may alternatively be presented as any one of a symbolic icon, a word, a letter, a number, an arrow, or any other representation of the posture state. In some cases, posture state indication 200 may be presented without supplementary posture state indication 202.

In addition to graphical, textual or other visible indications of posture state, the external programmer may present audible and/or tactile indications of posture state via any of a variety of audible or tactile output media. An audible indication may be spoken words stating a posture state, or different audible tones, different numbers of tones, or other audible information generated by the programmer to indicate posture state. A tactile indication may be, for example, a somatosensory indication, such as a different numbers of vibratory pulses delivered in sequence or vibratory pulses of different lengths, amplitudes, or frequencies. The user interface of FIG. 9 is merely illustrative in nature. More or less information may be provided to patient 12, as desired by the clinician or the patient.

Figure 10:
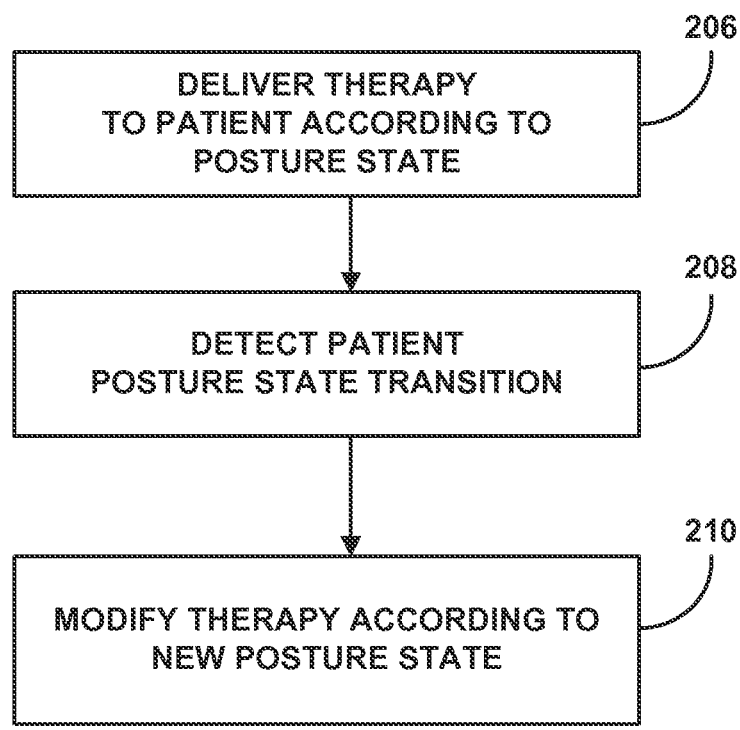
FIG. 10 is a flowchart illustrating an example technique for modifying stimulation therapy based on patient posture states.

FIG. 10 is a flowchart illustrating an example technique for modifying stimulation therapy based on patient posture states. For purposes of illustration, the example techniques will be described with respect to implantable stimulation system 14 described herein. However, such a technique may be implemented by any suitably configured system utilized to provide electrical stimulation therapy to a patient, such as, e.g., a stimulation system that is carried at least partially external to the body. Further, utilization of such an example technique is not limited to electrical stimulation therapy. Rather, in some examples, such a technique may be implemented in other patient therapy systems, including those configured to provide drug delivery therapy, e.g., implantable drug delivery system 26 described herein.

Referring to FIG. 10, processor 80 of IMD 14 controls stimulation generator 84 (FIG. 4) to generate and deliver therapy to a patient, e.g., in the form of electrical stimulation pulses delivered to patient 12 via stimulation leads 16A and 16B (206). As previously described, the electrical stimulation therapy may be provided to patient 12 according to one or more stimulation programs. Accordingly, stimulation generator 84, under the control of processor 80, may generate stimulation pulses having parameters values for stimulation parameters defined by one or more stimulation programs.

The specific parameter values defined by the stimulation programs may be appropriate for a posture state of patient 12 detected via posture state module 86. Thus, upon detection of the posture state by posture state module 86 (FIG. 4), processor 80 may control stimulation generator 84 to generate and deliver therapy to patient 12 according to the one or more therapy programs associated with the detected posture state. In some examples, the associations between therapy programs and patient posture states are stored by memory 82 of IMD 14. In one example of posture responsive therapy delivery, if processor 80 of IMD 14 detects that patient 12 is lying down via posture state module 86, processor 80 controls stimulation generator 84 according to the corresponding stimulation program to generate and deliver stimulation signals in accordance with the therapy program associated with the lying down state. In this way, IMD 14 delivers a stimulation signal having a stimulation amplitude and/or other parameters that are appropriate for patient 12 when lying down.

While providing therapy to patient 12, IMD 14 may detect a patient posture state transition (208). IMD 14 may modify stimulation to correspond with the patient posture state into which the patient transitioned, as detected by the posture state module (210). For example, if the posture state transition is from an upright posture state to a lying down posture state, for example, IMD 14 may change the amplitude of the stimulation from an existing level associated with the upright posture state to a desired level associated with the lying down posture state. A plurality of posture state definitions and associated therapy delivery regimes may be stored in memory 82 of IMD 14.

In some examples, the transition from controlling therapy based on one set of therapy parameter values (e.g., those associated with the upright posture state) to controlling therapy based on a second set of therapy parameter values may occur over time. For instance, rather than changing therapy abruptly upon the detection of a new posture state, IMD 14 may gradually change therapy so that the patient has an opportunity to slowly adjust to the new therapy levels. As a specific example, if the patient transitions from a lying posture state to an upright posture state that is associated with an increased amplitude, IMD 14 may gradually ramp the amplitude upward from that associated with the lying posture state to the amplitude associated with the upright posture state. This may eliminate any discomfort associated with an abrupt increase in amplitude.

As mentioned above, outputs of sensors 86A may be periodically sampled. The sampled signals may then be used to determine a posture state of the patient. In one embodiment, signals from sensors 86A are sampled 25 times a second, although this number is arbitrary. The sampling rate could be higher or lower in other examples. Assuming the system can operate fast enough, each sample can be used to determine a current posture state for the patient.

In systems such as those described herein that utilize a patient's posture state to control various aspects of the system, it may be advantageous to suspend controlling certain system aspects based on a patient's current posture state. For instance, when it is known that the patient's posture is changing at a rate that is above a predetermined threshold, it may be advantageous to temporarily stop making therapy adjustments based on a current posture state. During this time, the patient may be in flux between one or more posture states. Attempting to change therapy parameters values based on detection of what may be a very transient posture state could lead to discomfort for the patient or could change therapy levels to those which may make it difficult for the patient to complete the posture state transition. Moreover, making multiple therapy adjustments based on posture states that are maintained for a very short period of time may waste processing (and hence battery) power.

According to aspects of the disclosure, a patient's movement velocity may be used to determine when the patient is changing posture states. When the movement velocity rises above one or more predetermined thresholds, it may be advantageous to stop changing therapy parameter values based on a patient's current posture state. Moreover, in such scenarios, it may also be advantageous to temporarily stop determining the patient's posture state altogether since continuing to determine the patient's posture state throughout the period of high movement velocity will require processing power and may cause the system to expend energy unnecessarily.

Figure 11:
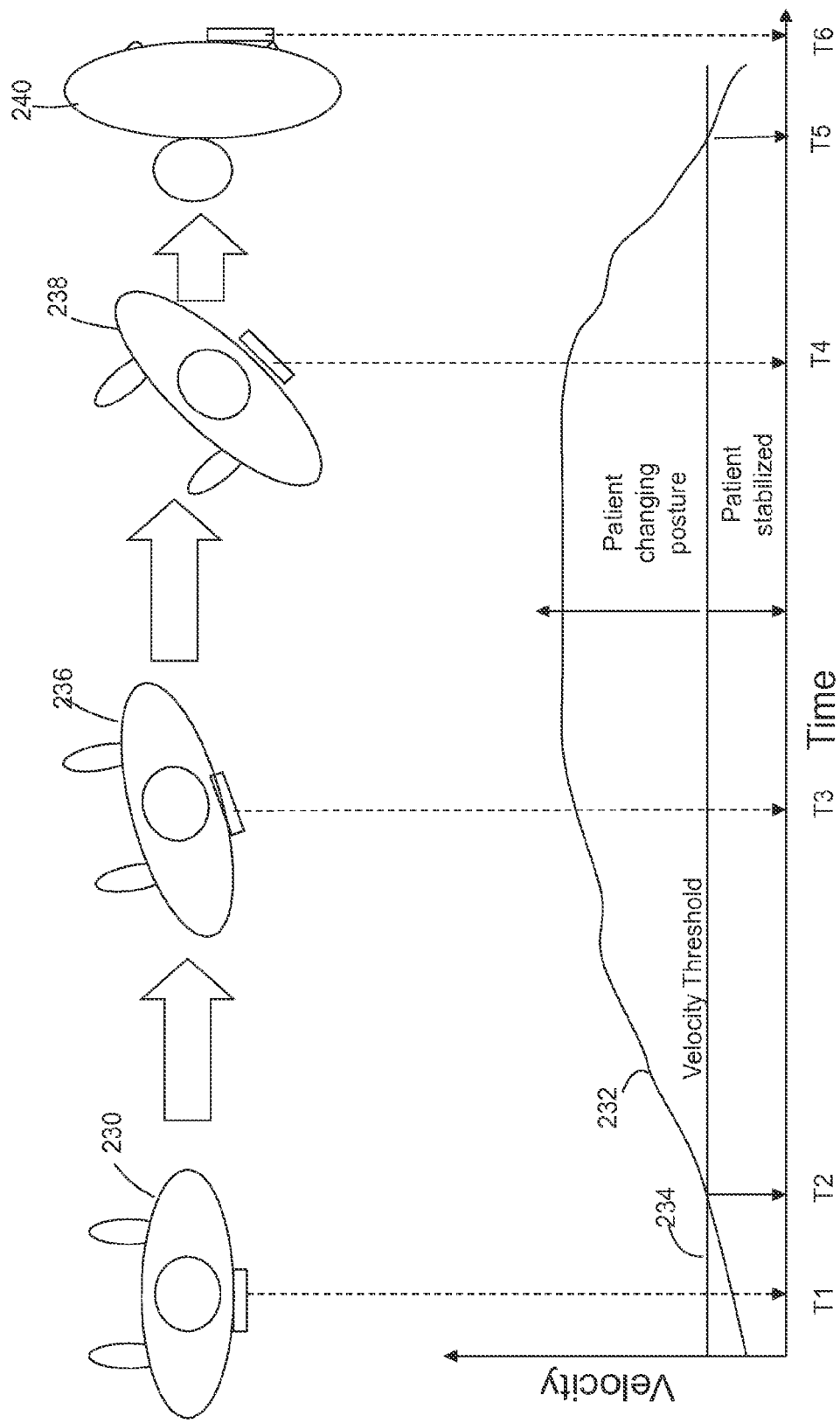
FIG. 11 is a conceptual diagram illustrating a movement velocity of a patient.

FIG. 11 is a conceptual diagram illustrating a patient 12 who is moving over time. The level of movement is determined by the patient's movement velocity represented along the Y axis. Time is represented by the X axis.

The movement velocity may be determined in one example based on a DC component of one or more signals from sensors 86A, such as signals from a three-axis accelerometer. In one scenario, the DC signals of an accelerometer may be used to determine a patient's position relative to gravity. This is in contrast to an AC component of the accelerometer signal which may provide an activity level of the patient. By determining changes over time of the DC signals, the patient's movement velocity can be determined. Various techniques for determining movement velocity are described in detail below.

Returning to the scenario depicted in FIG. 11, assume that at time T1, the patient is in an upright position 230 that is relatively stationary. This is indicated by the fact that the patient's movement velocity represented by waveform 232 is below the movement velocity threshold represented by line 234.

The patient then begins to change position resulting in a movement velocity that begins to increase. At time T2, the patient's movement velocity increases beyond the velocity threshold. During the time between T2 and T5, the patient's movement velocity remains above the threshold and the patient transitions between multiple positions, including position 236 at time T3 and position 238 at time T4. At time T5, the patient's movement velocity drops below the velocity threshold as the patient's position stabilizes. At time T6, the patient is in a forward leaning posture 240.

Between times T2 and T5, it may be advantageous for IMD 14 to suspend use of the patient's current posture state for controlling some aspect of the system. For instance, IMD 14 may stop using the patient's current posture state for adjusting therapy delivery. In particular, assume that at time T2, the patient is determined to be in the upright posture state 230, which is the last stable posture state the patient occupied prior to entering the relatively high-velocity period between times T2 and T5. As such, therapy may continue to be delivered based on the upright posture state 230 between times T2 and T5 without regard to the various posture states 236 and 238 assumed while the patient's velocity exceeded the velocity threshold 234. Therapy delivery continues based on this upright posture state until the patient's movement velocity drops below the velocity threshold at time T5. At time T5, the system may resume determining the patient's current posture state and delivering therapy according to this posture state. For instance, at time T5, the posture state module 86 may determine the patient is now in a leaning forward posture state 240 which is held until time T6. Therefore, at time T5, the system may transition from delivering therapy based on the upright posture state 230 to delivering therapy based on the leaning forward posture state assuming the patient is in this posture state at time T5. If at a time after time T6, the patient changes to another posture state while movement velocity remains below the velocity threshold, the system will detect this new posture state and transition to delivering therapy according to this new posture state, and so on.

The foregoing contemplates temporarily suspending patient therapy adjustments based on a current patient posture state if the patient's movement velocity exceeds a threshold. It may be appreciated that other aspects of control may be started and/or stopped based on the patient's velocity exceeding the velocity threshold. For instance, some physiological parameters may only be usefully collected when the patient is below, or above, a velocity threshold. For example, it may be desirable to track a resting heart rate only when the patient's velocity is below the threshold. Conversely, it may be desirable to track a moving heart rate only when the patient's velocity is above the threshold. As yet another example, it may be advantageous to trigger a notification when the patient's velocity exceeds the velocity threshold. For example, if the patient is in a care facility, it may be advantageous to provide an alert to a caregiver who may be remotely-monitoring the patient to indicate the patient is in an upright posture state and is further undergoing a relatively high-velocity so that the caregiver can provide extra attention to ensure the patient does not suffer a fall. Thus, while use of posture state in conjunction with patient velocity is described herein primarily in relation to automatic therapy adjustment, other embodiments may utilize patient velocity in conjunction with posture state to provide other functions and/or control other aspects of the system.

In an embodiment wherein a patient's posture state is used in conjunction with patient velocity to control multiple aspects of the system (e.g., suspension of therapy adjustment as well as suspension of monitoring of a physiological parameter), different thresholds may be used for different purposes. For instance, a different velocity threshold may be used to temporarily suspend therapy adjustments based on a current posture state than is used to determine that physiological measurements for a resting heart rate should be temporarily suspended, and so on. Any one or more of these thresholds may be programmable by a user such as a clinician or patient in some examples.

During such times as the period between time T2 and time T5 when the patient's velocity exceeds a velocity threshold, it may be advantageous to continue determining the patient's current posture state even though that posture state may not be used to control therapy adjustments. Even during times of higher patient velocity, determining the patient's current posture state may be useful for other purposes. For instance, the patient's current posture state may continue to be recorded during this time for use in analyzing the patient's movements over time, as may be required to determine how the patient is responding to therapy. As an example, periods of higher activity may be of particular interest to a clinician in determining how well a patient is responding to therapy. As such, the system may continue to determine the patient's current posture state for use in performing patient diagnostics and analysis even after the patient's velocity exceeds a threshold. Moreover, the patient's posture states during these higher-velocity time periods may be used to control other things besides therapy adjustments, such as the generation of notifications when it is determined the patient may have suffered a fall. For these, and other reasons, it may be beneficial for posture state module 86 to continue to determine a patient's current posture state during times of higher velocity when the patient's velocity exceeds a threshold, such as between times T2 and T5 in FIG. 11.

On the other hand, it may be advantageous in some embodiments to suspend determination of a patient's current posture altogether during times of higher patient velocity. This may allow the system to save more processing resources. Thus, at time T2, posture state module may discontinue determining the patient's current posture state. Instead, posture state module 86, in conjunction with processor 80, may determine the posture state that is to be utilized to control therapy and/or other system functions is the last-recorded stable posture state. As previously described, this last-recorded stable posture state may be stored within a storage device of the system for retrieval by posture state module 86 during high-velocity periods. At time T5, posture state module 86 may resume determining the patient's current posture state for recording purposes (e.g., patient analysis) and/or for use in controlling various system aspects. Thus, posture state module may, but need not, continue to determine a patient's current posture state after the patient's velocity exceeds a threshold.

Next, various approaches for determining the patient's movement velocity are considered. As discussed above, there are a number of ways to determine movement velocity, which may be based on a DC component of one or more sensor signals, such as accelerometer signals. According to one technique, a patient's movement velocity may be based on distance velocity. The distance velocity may be calculated as a distance between two vectors, each representing a patient's posture at successive moments in time. This is discussed further in reference to FIG. 11.

Figure 12:
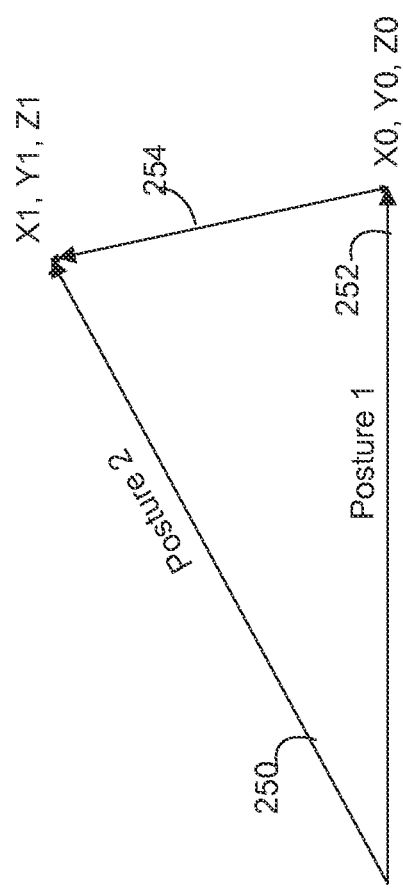
FIG. 12 is a conceptual diagram illustrating determining movement velocity based on a distance velocity determination.

FIG. 12 is a conceptual diagram illustrating determining a patient's movement velocity based on a distance velocity determination. Assume in this example vector 252 is a sensed coordinate vector corresponding to the patient's position 230 at time T1 (FIG. 11). Such a vector may be expressed as [x0, y0, z0]. As described above in reference to determination of a patient's posture state, a sensed coordinate vector [x0, y0, z0] is a vector in three-dimensional space. This vector is provided by, or derived from, the outputs of a three-axis accelerometer or some other sensor(s) 286A that provide positional and/or activity information, for instance.

For this example, assume that sensed coordinate vector 250 represents the patient's position 236 at time T3. Again, this position may be expressed as a vector [x1, y1, z1] in three-dimensional space provided by, or derived from, sensor(s) 286A. A third vector 254 represents the distance between these two vectors. The length of vector 254 may be expressed as $\|V\| = \sqrt{(x1-x0)^2+(y1-y0)^2+(z1-z0)^2}$.

Movement velocity may be determined as the distance moved (e.g., the length of vector 254) divided by the time over which this distance was moved, which in this case is T3−T1. In other words, the movement velocity of the patient between posture states 230 and 236 may be expressed as $\|V\|/(T3-T1)$. If this movement velocity is above a predetermined velocity threshold such as velocity threshold 234, posture state module 86 may temporarily suspend determining a patient's posture state until the movement velocity drops below this threshold. Alternatively or additionally, IMD 14 may suspend delivering therapy according to a patient's current posture state and instead deliver therapy according to the posture state that was most-recently detected prior to the movement velocity increasing beyond the threshold.

The previous example provides a very course illustration of determining patient velocity based on two posture states. The example is "course" because a relatively large change in the patient's position occurs between posture states 230 and 236. This posture state change likely occurs over a relatively large amount of time (e.g., one or more seconds). In general, it may be desirable to determine movement velocity over a smaller period of time. The time period over which movement velocity may be determined is relatively arbitrary, and may depend upon the rate at which signals from sensors 86A are sampled, the expected rate of change in the velocity, a processing rate of processor 80, an amount of power available to be consumed on posture state processing, and so on. In one example, successive vectors are obtained at a rate of four hertz such that the time period between two vectors will be 0.25 seconds. Successive posture vectors may be obtained more or less frequently however. For instance, successive posture vectors may be obtained at a rate of between 1 Hz and 64 Hz in one embodiment.

In some cases, it may be desirable to perform filtering to prevent one outlying sample from skewing a movement velocity determination. For instance, a rolling (or box-car) average of multiple velocity determinations may be used as the current velocity determination. More specifically, a rolling average may rely on an average of the current movement velocity determination and N other most-recent movement velocity determinations (as may be stored within a rolling buffer, for instance.) Any number of past velocity determinations may be considered when deriving this rolling average. Other filtering techniques may be utilized, such as discarding velocity determinations that represent too great of a change between the current velocity and the velocity determination most recently derived. Filtering techniques may be implemented in hardware, software, or some combination thereof.

In one specific example, sampling of sensor signals occurs at a rate that is faster than the rate at which successive poster vectors are determined. For example, sampling of the sensor signals may occur at 32 Hz. These signals are filtered (e.g., by using a software or hardware filter) and are then used to obtain successive posture vectors at a rate of 4 Hz.

It may be noted that the sensed posture vectors used to determine a patient's movement velocity may, but need not, correspond to a defined posture state. For instance, two consecutive sensed coordinate vectors used to determine a patient's velocity may each map to a region in three-dimensional space that corresponds to a predetermined posture state such as Upright or Leaning Forward. This mapping may be carried out in any of the ways described above, for example. Two consecutive vectors may both map to a same region in posture state (e.g., they may both map to the Upright posture state), or they may each map to regions in posture state associated with respectively different posture states (e.g., one vector maps to the Upright posture cone and the other vector maps to a Leaning Forward posture cone.)

In another example of the foregoing, one or both of two consecutive sensed coordinate vectors using to determine patient velocity may map to a region in three-dimensional posture space that is not associated with a previously-defined posture state. That is, one or both of the consecutively-measured vectors may reside within hysteresis space. In this latter case, a vector mapping to hysteresis space may never-the-less be described as corresponding to a patient's posture state (albeit an undefined posture state) because the vector represent a positions of the patient. Thus it will be understood that when a patient's velocity is described herein in reference to two posture states, these posture states are not necessarily both previously-defined posture states (e.g., "Upright" or "Lying") but rather one or more of these posture states may be positions that map to hysteresis space.

Returning to a discussion of specific velocity-determination methods, the above-described approach derives a Euclidean distance for calculating $\|V\|$, other types of distance measurements may be used in the alternative. As another example, a city-block distance $|x1-x0|+|y1-y0|+|z1-z0|$ may be derived between a first vector $[x0, y0, z0]$ and a second vector $[x1, y1, z1]$. Yet another technique utilizes a maximum absolute difference which selects as the distance between the vectors the maximum of $|x1-x0|$, $|y1-y0|$ and $|z1-z0|$. As another example, a Manhattan distance may be used. Any other technique that derives a distance measurement between the two vectors may be used in the alternative.

Figure 13:
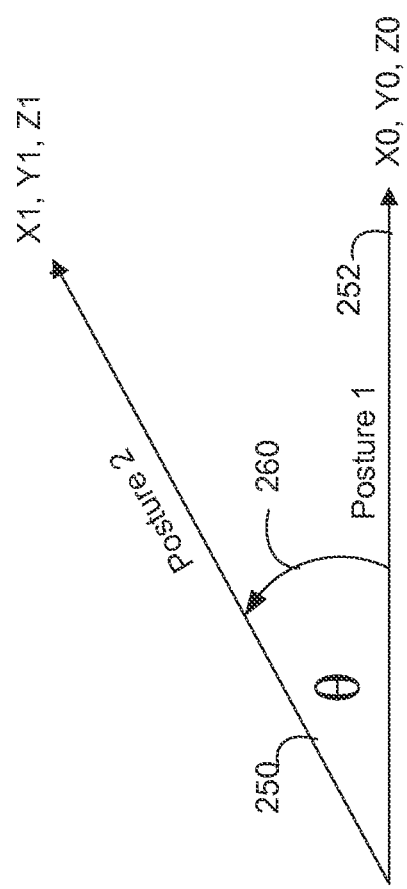
FIG. 13 is a conceptual diagram illustrating determining movement velocity based on an angular velocity determination.

While a distance velocity measurement may be utilized, another approach may use an angular velocity to determine whether the patient's movement velocity exceeds a threshold. FIG. 13 is a conceptual diagram illustrating a patient who is moving between posture 1 and posture 2 over a time period T. Posture 1 252 may be represented by a sensed coordinate vector $[x0, y0, z0]$ and posture 2 250 may be represented by sensed coordinate vector $[x1, y1, z1]$. The angle $\theta$ between these two sensed coordinate vectors can be determined as follows:

$$\theta = \arccos \frac{x0 \cdot x1 + y0 \cdot y1 + z0 \cdot z1}{\sqrt{x0^2 + y0^2 + z0^2} \cdot \sqrt{x1^2 + y1^2 + z1^2}}$$

wherein the numerator is the sum of the dot products between (x0, x1), (y0, y1), and (z0, z1), and the denominator is the product of the length of the two vectors.

The angular velocity may be determined by dividing the angle between the two vectors by the time between the sensing of the first and second sensed coordinate vectors, as described above. As previously discussed, this time period may be based on a sampling rate of the signals of sensors 86A, a speed of processor 80, and/or other system considerations. In some cases, it may be desirable to increase the time between the vectors used to determine patient movement velocity since the processing performed to calculate velocity will drain power, depleting the power source, and possibly leading to increased heating of a device.

It may be noted that the arccosine function is relatively processing-intensive, and therefore requires processing time and power to complete. Therefore, in some embodiments, it may be desirable to use a surrogate of the angle to determine the angular velocity. As one example, a velocity may be determined by dividing the sine or the cosine of the angle between two vectors by the time between measuring these vectors. This is similar to the technique described above of using the cosine of the angle rather than the angle itself when comparing a sensed coordinate vector to a reference coordinate vector used by a posture state definition. The cosine may be determined as $$\cos\theta = \frac{x0 \cdot x1 + y0 \cdot y1 + z0 \cdot z1}{\sqrt{x0^2 + y0^2 + z0^2} \cdot \sqrt{x1^2 + y1^2 + z1^2}}$$

As discussed above, the cosine of the angle may be divided by time rather than dividing the actual angle by time to obtain a metric indicative of patient movement velocity. Unlike many of the other movement velocity metrics described herein, this metric will be inversely proportional to movement velocity since the cosine gets smaller as the angle increases so long as the angle between the two vectors is within a certain angular range, as discussed further below. Thus, as the patient's movement velocity increases, the value for this metric will decrease. When the metric drops below a corresponding threshold, therapy adjustment and/or posture state determination may be suspended until the patient's movement again drops below an acceptable level, as indicated by an increased value in this metric. This use of a cosine metric can save processing steps and therefore also conserve power and processing time, since no angle derivation is required.

In the foregoing manner, the cosine will have an inverse relationship to the angle between two vectors so long as the angle is ranging between 0 and 180 degrees, or between 0 and −180 degrees. If the angle is greater than 180 degrees or less than −180 degrees, this relationship will not be consistent. Thus, if the cosine is to be used as a surrogate for the size of the angle between two vectors, it may be desirable to limit the time period between obtaining two successive sensed coordinate vectors such that patient movement during this time period is associated with an angle that is not greater than 180 degrees or less than −180 degrees.

A similar metric could use the absolute value of the sine of the angle between two vectors rather than the cosine of an angle to derive a movement velocity metric. The sine of an angle between two vectors can be calculated by replacing the numerator of the cosine equation set forth above (which is the dot product between the two vectors) with the cross-product between the two vectors. The absolute value of the sine of the angle may then be divided by the time over which the two sensed coordinate vectors were measured in a manner similar to that described above. In this case, the absolute value of the sine will increase between 0 and 1 so long as the angle between the two sensed coordinate vectors is between 0 and 90 degrees or between 0 and −90 degrees. The time period over which the two vectors are obtained may be adjusted to ensure that two successive vectors will lie within one of these two ranges if this alternative metric is to be used. For instance, this adjustment may be performed by increasing the sampling rate of the sensor signals that are used to obtain the successive sensed coordinate vectors so that patient movement during the time period between the two vectors will likely not result in angular movement that exceeds the required range.

In all of the foregoing examples of a velocity metric, some indicator of distance or angular movement is divided by a period of time to obtain the velocity indicator. It may be appreciated that if the time period by which the division occurs is always the same, the step of dividing by time is not necessary. Thus, another embodiment may simplify the process by merely utilizing the distance or angular movement itself as an indication of velocity. In this type of embodiment, the measure of distance or angular movement will be compared to a corresponding distance or angular threshold. For instance, a derived angular distance may be compared against a corresponding threshold such as a cosine of an angle that is less than or equal to 0.5, a sine of an angle that is greater than or equal to 0.4, or an angle that is greater than 50 degrees. A derived Euclidean or some other distance measurement may be compared to an example distance threshold. Any distance or angular indication such as the example metrics set forth herein may be used to indicate velocity without a need to divide by a time period so long as the time between successive distance or angular indications is always constant.

In one example, it may be desirable to determine the velocity metric based on some combination of the distance and angular velocity metrics. For example, the two metrics could be weighted in some predetermined manner to obtain a blended parameter that is then compared against a threshold that has been selected accordingly.

In accordance with the foregoing description, it may be advantageous to temporarily suspend making therapy adjustments based on the patient's current posture state when the patient's movement velocity increases beyond a threshold, as indicated by the metric in use to describe the movement velocity. In other examples, it may be advantageous to temporarily suspend posture state determination altogether during periods of high patient velocity. If the movement velocity metric being used to measure patient velocity is directly proportional to velocity, posture state detection may be suspended when the metric is greater than or equal to a corresponding threshold in one example. If the movement velocity metric is inversely proportional to movement velocity (e.g., as when cosine/time is used as the metric to describe a patient's movement velocity), posture state detection may be suspended when the movement velocity is equal to, or less than, the corresponding threshold in one scenario.

Threshold values may be selected in a number of ways. In some scenarios, it may be desirable to derive a single threshold value to be used in all circumstances. This single threshold value may be hardcoded into the system (e.g., by the manufacturer). Alternatively, such a threshold may be programmable and may be selected by a clinician or another user such as a patient. In one example, this threshold could be customized for the patient. As another scenario, thresholds may be selected based on previously-collected objectification data that provides insights into the patient's posture state changes and/or adjustments made to therapy parameters while the patient was moving.

As a particular example of customizing a threshold based on patient preference, some patients may want more therapy differentiation as they go about their activities. For these patients, thresholds may be set so that the movement velocity must be higher before posture state determination is temporarily suspended. This will allow posture-responsive therapy delivery to continue even while a patient's movement velocity reaches some moderate level. On the other hand, for patients that are more sensitive to changes in therapy levels and who want to make sure that a stable posture state is attained prior to a change being made to therapy levels, the thresholds may be tailored to select a lower movement velocity threshold level. This will cause posture state determination (and the associated therapy adjustments) to be suspended based on a lower activity level.

In some cases, it may be desirable to allow a patient to select a threshold level. For instance, the patient could provide user input (e.g., via a button push on a patient programmer) when the patient is moving at a velocity that corresponds to the desired movement velocity threshold level. This may allow the patient to determine at which velocity level therapy adjustment and/or posture state determination should be suspended.

According to some examples, multiple thresholds may be available for use within the system, with the threshold that is in use at a particular time being selected based on some other system or patient parameter. For instance, the threshold may be selected based on a time of day or day of week. This would allow the threshold to vary, for example, between daytime, nighttime, week days, weekends, work hours, etc. Thus, the use of thresholds could be tailored for a patient's job activities versus leisure activities, daytime activities versus sleep, and so on.

As another example, thresholds may be posture-state-specific. For instance, a threshold may be selected based on a patient's most-recently determined stable posture state. Thus, for instance, a lower movement velocity may be selected in association with lying posture states than is selected for more upright posture states, and so on. If desired, each defined posture state may be associated with a different respective movement velocity threshold as shown in Table 1.

TABLE 1

| POSTURE STATE | THRESHOLD |
|---|---|
| Upright | Threshold 1 |
| Lying (Front) | Threshold 2 |
| Lying (Back) | Threshold 3 |
| Lying (Right) | Threshold 4 |
| Lying (Left) | Threshold 5 |
| Leaning Forward | Threshold 6 |

If the patient's movement velocity exceeds the movement velocity threshold associated with the respective stable posture state while the patient occupies that posture state, some action may be taken in accordance with the foregoing description. For instance, the system may temporarily discontinue using the patient's currently-detected posture state to control an aspect of the system, such as therapy delivery. Alternatively or additionally, posture state detection may itself be temporarily suspended.

Other patient and/or system parameters can be used alone or in some combination to select the threshold in use at a given time within the system. For instance, heart rate, temperature, blood pressure, or some other parameter (e.g., posture state, time/day, etc.) may be employed to select a threshold for use at that time.

In some instances, it may be desirable to utilize one threshold to prompt the system to discontinue using a patient's current posture state to control one aspect of the system (e.g., therapy delivery), while using a different threshold to cause the system to discontinue using a patient's current posture state to control a different aspect of the system (e.g., sensing a particular physiologic parameter). Yet another threshold may be used to prompt the system to discontinue posture state determination. Thus, many alternative examples are available.

Figure 14:
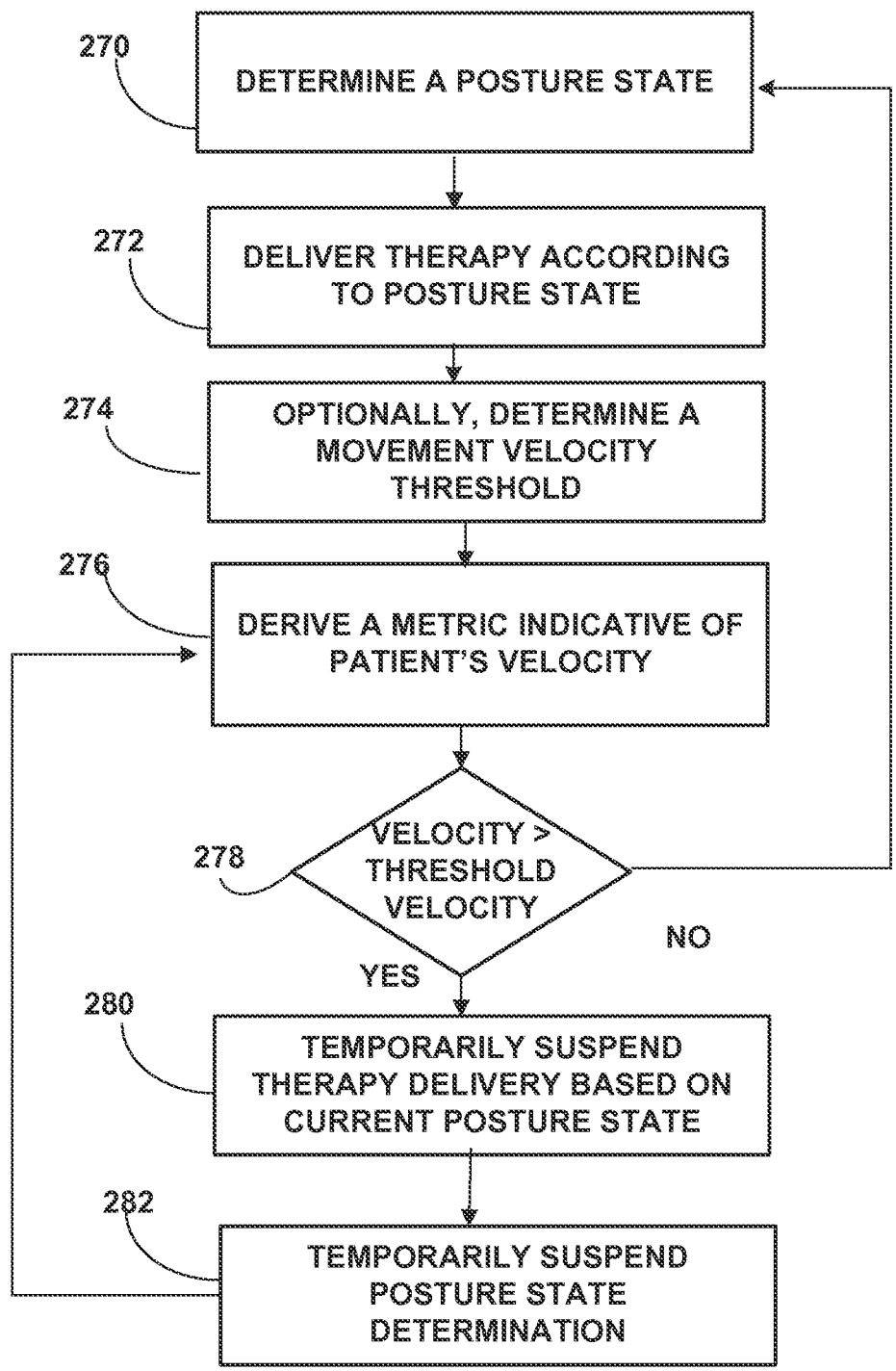
FIG. 14 is a flow diagram of one example method according to the current disclosure.

FIG. 14 is a flow diagram of one example method according to the current disclosure. A patient's posture state may be determined (270). The determination may be made, for instance, according to any of the example methods described herein. The determination may be made via logic within IMD 14, via logic within an external device such as programmer 30 or 60, or via a combination of logic within the IMD 14 and logic within an external device.

If desired, a therapy may be delivered in accordance with the determined posture state (272). For example, a stimulation and/or drug-delivery therapy may be controlled in accordance with the posture state determination. In other examples, other actions may be taken in addition to, or instead of, the therapy delivery. For instance, in one example, a notification may be issued or an alarm may be sounded based on the posture state determination, as may be desirable if it is likely the patient has taken a fall.

As another example, the posture state detection may prompt the system to obtain one or more physiological measurements. As a particular example, it may be desirable to take some measurements such as blood pressure or heart rate only when it is known the patient is occupying some predetermined posture state so that measurements can be more accurately compared. Thus, the determination that the patient is in that posture state may prompt the taking of the measurements. Thus, the posture state determination may be usefully employed to prompt various system responses in addition to, or instead of, being used to control therapy delivery.

Based on the posture state determination or some other system and/or patient parameter, a movement velocity threshold may be determined for use by the system (274). Such a determination may be made based on the most-recently-determined posture state, a measured patient parameter, or some other system parameter (e.g., time, day, etc.) The threshold determination could be made via one or more lookup tables stored in memory 82, 94 of an IMD or of an external device such as memory 108 of programmer 20. Alternatively, some equation or other function may be used to allow the threshold to be calculated rather than obtained from a storage device.

In a simple example, only a single threshold value need be stored or calculated for use in all scenarios. In this type of example, the threshold may only need to be obtained once (e.g., prior to the start of posture state determination step 270). In other cases wherein the threshold is more specific to a particular scenario, a movement velocity threshold may be obtained more often, such as during every iteration of the processing steps in the manner shown in FIG. 14.

In steps 276, a metric may be derived to describe the patient's movement velocity. As previously discussed, the movement velocity may be based on a distance or angular velocity. In some cases, as when sensed coordinate vectors are always obtained at uniform time increments, the metrics may be an angle or distance metric itself without any reference to (e.g., division by) time. In some examples, a distance or angular metric may be combined in some manner (e.g., using weighting factors) to obtain a single metric. Various metrics are available for each of the distance and angular velocities as previously described. The metric chosen for use may depend on the processing power and/or capacity of the power source available within the system.

If the patient's movement velocity is greater than the threshold velocity as indicated by the velocity metric, the system may suspend control of therapy delivery and/or one or more other aspects of control of the system (e.g., parameter measurement) based on the patient's current posture state (280). Alternatively or additionally, the posture state determination itself may be temporarily suspended in one example (282).

During periods of high velocity, operation may continue as though the patient has remained in the most-recently-determined posture state as determined in step 272. For instance, therapy may continue to be controlled according to the therapy parameters associated with that most-recently-determined stable posture state of the patient. In another example, during these high-velocity periods, therapy could be delivered according to a set of "benign" parameters (e.g., a set of stimulation parameters that contains a relatively low stimulation amplitude, etc.) Therapy may be delivered according to this benign therapy parameter set until the patient's movement velocity drops below the threshold movement velocity and the patient's posture state is again determined. According to still another example, therapy delivery may be ceased entirely when the patient's velocity increases beyond the velocity threshold.

If the movement velocity of the patient indicated by the velocity metric is less the velocity threshold, processing returns to step 276 to derive another metric indicative of the patient's movement velocity. If the patient's movement velocity is not greater than the threshold velocity, processing may return to step 270 to determine the patient's current posture state, which may be the same as, or different from, the posture state most-recently determined for the patient. Therapy may be delivered in accordance with this determination, which may involve a change to therapy parameters if the patient's posture state is determined to have changed from the last time the determination was made.

In the above discussion, the patient's velocity is determined based on changes over time of the patient's position in three-dimensional space as may be determined by a DC component of one or more accelerometer signals. These signals may be used to periodically determine the patient's position in 3-dimensional space, and further to determine how the patient's position is changing over time. This type of velocity is referred to herein as "movement velocity".

In one embodiment, an AC component of the signals of sensor(s) 86A may be sensed by posture state modules 86, 98 to derive a signal indicative of a patient's activity level. These activity signals may yield an activity count (e.g., footfalls or some other count based on activity) which may be tracked over a predetermined period of time to yield an "activity velocity" metric. An example activity metric may be "N counts/second", wherein N is derived from the AC signal component measured over one second.

This activity metric may be used instead of, or in addition to, a movement velocity metric to determine when to suspend use of the patient's current posture state in controlling therapy or some other aspect of the system. For example, while this activity velocity metric has some predetermined relationship to a corresponding activity velocity threshold (e.g., an activity count of greater than 10 counts/second), control of therapy adjustments based on the patient's current posture state may be temporarily suspended in a manner similar to that shown in FIG. 14. In this case, therapy delivery and other responses may be controlled according to any of the various mechanisms above. For instance, therapy delivery may continue in accordance with the patient's posture state most-recently determined prior to the time the activity velocity metric exceeded the threshold. Alternatively, therapy delivery could be suspended or could be controlled according to some "benign parameter set". If desired, some other aspect of system control in addition to, or instead of, therapy adjustment may be controlled based on this activity metric. This activity metric may alternatively or additionally be used to suspend posture state determination itself during time periods wherein the activity metric has a predetermined relationship to a threshold (e.g., greater than 10 counts per second, etc.) This may conserve power as described above.

Embodiments described above contemplate temporarily discontinuing control of some aspect of the system based on a current posture state determination during time periods wherein the patient's velocity exceeds a velocity threshold. This may involve periodically (e.g., at a frequency of 4 Hz) re-determining posture state so that it is known when the patient's velocity drops below the threshold so that control based on a current posture state may be resumed. In another embodiment, when the patient's velocity has been determined to exceed a velocity threshold, some aspect of system control based on a current posture state may be suspended for a predetermined period of time (e.g., some number of seconds.) At the expiration of this time period, the velocity may again be determined to determine whether the patient's velocity remains above the threshold such that control based on current posture state should remain suspended for another predetermined period of time, or whether operation based on current posture state should be resumed. This type of technique slows the frequency at which velocity and may therefore save some processing resources within the system. If desired, posture state determination itself may likewise be suspended during the predetermined time period following an indication that the patient's velocity has exceeded a threshold.

The techniques described in this disclosure may be implemented, at least in part, in hardware, software, firmware or any combination thereof. For example, various aspects of the techniques may be implemented within one or more microprocessors, DSPs, ASICs, FPGAs, or any other equivalent integrated or discrete logic circuitry, as well as any combinations of such components, embodied in programmers, such as physician or patient programmers, stimulators, or other devices. The term "processor" or "processing circuitry" may generally refer to any of the foregoing logic circuitry, alone or in combination with other logic circuitry, or any other equivalent circuitry.

When implemented in software, firmware, or a sequencer code, the functionality ascribed to the systems and devices described in this disclosure may be embodied as instructions on a non-transitory storage medium such as RAM, ROM, NVRAM, EEPROM, FLASH memory, magnetic media, optical media, or the like. The instructions may be executed by a processor (e.g., processors 80, 92, 104) and/or other control circuitry (e.g., posture state modules 86, 98) which may include processing logic, sequencers, micro-sequencers, or some other logic capable or executing instructions. This support one or more aspects of the functionality described in this disclosure.

In addition, it should be noted that the systems described herein may not be limited to treatment of a human patient. In alternative examples, these systems may be implemented in non-human patients, e.g., primates, canines, equines, pigs, and felines. These animals may undergo clinical or research therapies that my benefit from the subject matter of this disclosure.

Many examples have been described. Various modifications may be made without departing from the scope of the claims. These and other examples are within the scope of the following claims.

What is claimed is:

1. A system comprising:
a sensor configured to sense one or more posture state parameters of a patient; and
a posture state module comprising circuitry configured to determine a posture state of the patient to be used in controlling an aspect of the system, the posture state being determined based on the one or more posture state parameters and a relationship between a velocity of the patient and a velocity threshold,
wherein the posture state module comprises circuitry configured to determine the velocity of the patient based on a distance between two sensed coordinate vectors, wherein each of the two sensed coordinate vectors is indicative of a respective posture state of the patient.

2. The system of claim 1, wherein the posture state module comprises circuitry configured to determine the posture state of the patient based on a previously-determined posture state of the patient during time periods wherein the velocity of the patient exceeds the velocity threshold.

3. The system of claim 1, wherein the posture state module comprises circuitry configured to determine the velocity of the patient based on a DC component of the posture state parameters.

4. The system of claim 1, further comprising a therapy delivery module comprising circuitry configured to deliver therapy to the patient based on the posture state of the patient.

5. The system of claim 4, wherein the therapy delivery module comprises circuitry configured to deliver therapy to the patient based on a current posture state of the patient and to temporarily suspend delivering therapy based on the current posture state of the patient if the velocity of the patient exceeds a predetermined velocity threshold.

6. The system of claim 4, wherein the therapy delivery module comprises circuitry configured to deliver the therapy to the patient based on a previously-determined posture state of the patient during time periods wherein the velocity of the patient is above the velocity threshold.

7. The system of claim 1, further comprising an implantable medical device comprising the sensor.

8. The system of claim 1, further comprising a device external to the patient comprising at least a portion of the posture state module.

9. The system of claim 1, further comprising a programmer configured to receive input to control the medical system.

10. The system of claim 1, wherein the posture state module comprises circuitry configured to determine the velocity of the patient based on an AC component of the posture state parameters.

11. The system of claim 1, wherein the velocity threshold is selectable.

12. The system of claim 1, wherein the posture state module comprises circuitry configured to suspend determining a current posture state of the patient during time periods wherein the velocity of the patient exceeds the velocity threshold.

13. A system comprising:
a sensor configured to sense one or more posture state parameters of a patient; and
a posture state module comprising circuitry configured to determine a posture state of the patient to be used in controlling an aspect of the system, the posture state being determined based on the one or more posture state parameters and a relationship between a velocity of the patient and a velocity threshold,
wherein the posture state module comprises circuitry configured to determine the velocity of the patient based on an angle between two sensed coordinate vectors, wherein each of the two sensed coordinate vectors is indicative of a respective posture state of the patient.

14. A method comprising:
sensing, by a sensor, one or more posture state parameters of a patient; and
determining, via a posture state module comprising circuitry, a posture state of the patient for use in controlling an aspect of the system, the determined posture state being determined based on the one or more posture state parameters and a relationship between a velocity of the patient and a velocity threshold, wherein the velocity of the patient is a movement velocity that is based on a distance.

15. The method of claim 14, further comprising delivering therapy to the patient based on the posture state of the patient.

16. The method of claim 15, further comprising delivering therapy to the patient based on a previously-determined posture state of the patient during time periods wherein the velocity of the patient exceeds the velocity threshold and delivering therapy to the patient based on a current posture state of the patient during time periods wherein the velocity of the patient does not exceed the velocity threshold.

17. The method of claim 16, further comprising suspending determining, via the posture state module circuitry, the current posture state of the patient during time periods wherein the velocity of the patient exceeds the velocity threshold.

18. The method of claim 14, wherein sensing one or more posture state parameters comprises sensing one or more posture state parameters via an accelerometer.

19. The method of claim 14, wherein sensing one or more posture state parameters comprises sensing one or more posture state parameters via a sensor carried by an implantable medical device.

20. The method of claim 14, further comprising determining the velocity of the patient based on the one or more posture state parameters.

21. The method of claim 20, wherein the velocity of the patient is based on an AC component of the one or more posture state parameters.

22. The method of claim 14, wherein the threshold is programmable.

23. The method of claim 14, wherein determining the posture state of the patient based on the one or more posture state parameters and the relationship between the velocity of the patient and the velocity threshold comprises determining the posture state of the patient based on a current posture state of the patient and determining that the velocity of the patient is below the velocity threshold.

24. The method of claim 14, wherein the distance is based on a distance between two sensed coordinate vectors, wherein each of the two sensed coordinate vectors is indicative of a respective posture state of the patient.

25. A method comprising:
sensing, by a sensor, one or more posture state parameters of a patient; and
determining, via a posture state module comprising circuitry, a posture state of the patient for use in controlling an aspect of the system, the determined posture state being determined based on the one or more posture state parameters and a relationship between a velocity of the patient and a velocity threshold,
wherein the velocity of the patient is a movement velocity that is based on an angle.

26. The method of claim 25, wherein the angle is based on an angle between two sensed coordinate vectors, wherein each of the two sensed coordinate vectors is indicative of a respective posture state of the patient.

27. A system comprising:
means for sensing one or more posture state parameters of a patient; and
means for determining, via a posture state module, a posture state of the patient based on the one or more posture state parameters and a relationship between a velocity of the patient and a velocity threshold,
wherein the velocity of the patient is based on a distance or is based on an angle.

28. A non-transitory storage medium storing instructions executable by a control circuit to cause the control circuit to
sense one or more posture state parameters of a patient; and
determine a posture state of the patient based on the one or more posture state parameters and a relationship between a velocity of the patient and a velocity threshold,
wherein the velocity of the patient is based on a distance or is based on an angle.

29. The storage medium of claim 28, wherein instructions executable by a control circuit further comprise instructions executable by the control circuit to cause the control circuit to control delivery of therapy to the patient based on a previously-determined posture state of the patient during time periods wherein the velocity of the patient exceeds the velocity threshold and to control delivery of therapy to the patient based on a current posture state of the patient during time periods wherein the velocity of the patient does not exceed the velocity threshold.

30. The storage medium of claim 28, wherein the instructions executable by a control circuit comprise instructions executable by the control circuit to cause the control circuit to control delivery of therapy according to a current posture state of the patient and to temporarily suspend delivery of the therapy according to the current posture state of the patient during time periods when the velocity of the patient exceeds a predetermined velocity threshold.

* * * * *